United States Patent [19]
Wittwer et al.

[11] Patent Number: 4,738,817
[45] Date of Patent: Apr. 19, 1988

[54] METHOD FOR FORMING PHARMACEUTICAL CAPSULES FROM HYDROPHILIC POLYMERS

[75] Inventors: Fritz Wittwer, Lupsingen; Ivan Tomka, Lenzburg; Hans-Ulrich Bodenmann, Münchenstein; Thomas Raible, Jona, all of Switzerland; Louis S. Gillow, Rockaway, N.J.

[73] Assignee: Warner-Lambert Company, Morris Plains, N.J.

[21] Appl. No.: 910,106

[22] Filed: Sep. 19, 1986

Related U.S. Application Data

[63] Continuation-in-part of Ser. No. 698,264, Feb. 5, 1985, Pat. No. 4,665,840, and a continuation-in-part of Ser. No. 641,550, Aug. 17, 1984, and a continuation-in-part of Ser. No. 641,663, Aug. 17, 1984, and a continuation-in-part of Ser. No. 641,664, Aug. 17, 1984, and a continuation-in-part of Ser. No. 798,344, Nov. 8, 1985, said Ser. No. 641,550, is a continuation-in-part of Ser. No. 543,694, Oct. 20, 1983, abandoned, said Ser. No. 641,663, is a continuation-in-part of Ser. No. 557,306, Dec. 2, 1983, Pat. No. 4,576,284, and a continuation-in-part of Ser. No. 557,502, Dec. 2, 1983, abandoned, and a continuation-in-part of Ser. No. 557,500, Dec. 2, 1983, and a continuation-in-part of Ser. No. 543,692, Oct. 20, 1983, and a continuation-in-part of Ser. No. 543,698, Oct. 20, 1983, abandoned, and a continuation-in-part of Ser. No. 543,699, Oct. 20, 1983, abandoned, said Ser. No. 641,664, is a continuation-in-part of Ser. No. 548,794, Nov. 4, 1983, abandoned, said Ser. No. 798,344, is a continuation of Ser. No. 451,577, Dec. 20, 1982, abandoned.

[51] Int. Cl.$^4$ ............................................. B29B 7/00
[52] U.S. Cl. ................................. 264/328.14; 106/135; 106/136
[58] Field of Search .................... 264/328.1, 328.14; 206/530, 531, 532

[56] References Cited

U.S. PATENT DOCUMENTS

| | | | |
|---|---|---|---|
| 2,831,852 | 4/1958 | Savage | 536/91 |
| 3,664,495 | 5/1972 | Graham | 206/530 |
| 4,076,846 | 2/1978 | Nakatsuka et al. | 426/89 |
| 4,482,386 | 11/1984 | Wittwer | 106/213 |
| 4,576,284 | 3/1986 | Wittwer | 206/530 |

Primary Examiner—Theodore Morris
Attorney, Agent, or Firm—Howard Olevsky; Stephen Raines

[57] ABSTRACT

Novel injection molded pharmaceutical capsules of gelatin having a cap member, a body member, means to form a plurality of compartments therein, and means for locking the cap and body members together to form a tamper-resistant connection.

3 Claims, 38 Drawing Sheets

FIG. 3
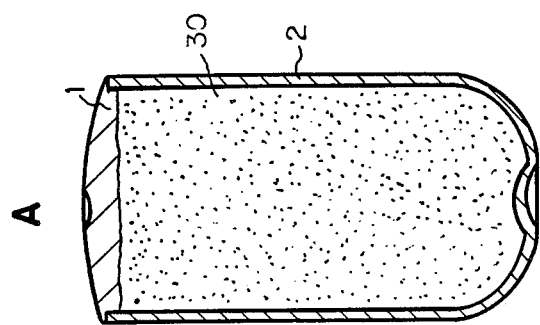
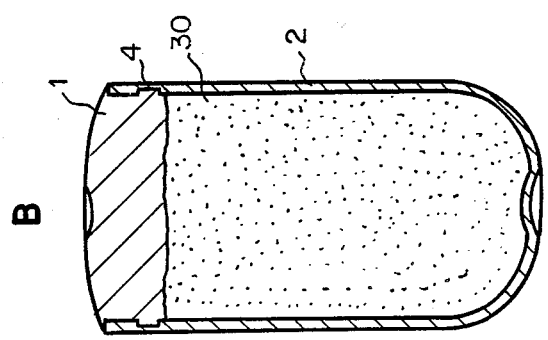
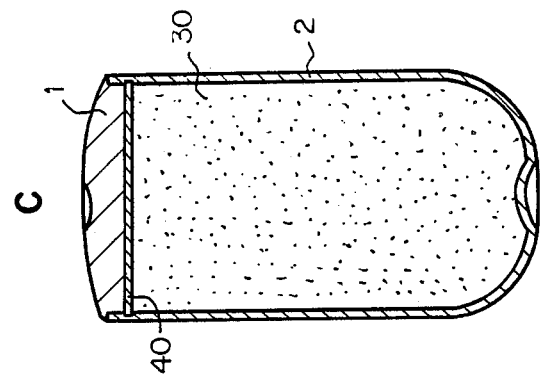

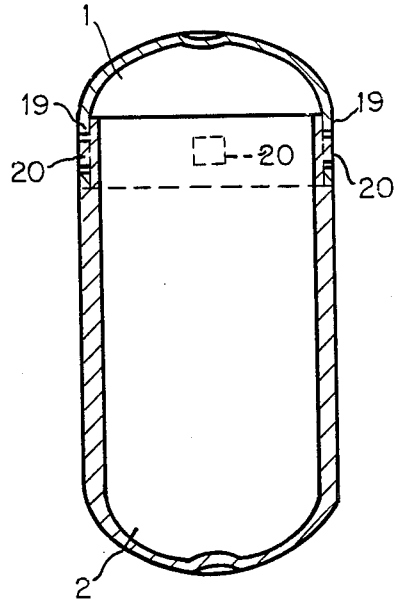
FIG. 15
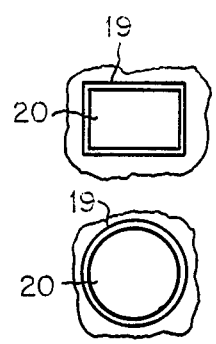
FIG. 16
FIG. 17
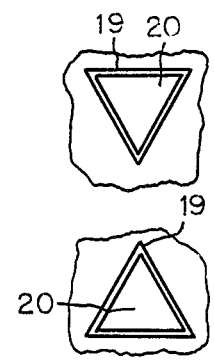
FIG. 18
FIG. 19
FIG. 20
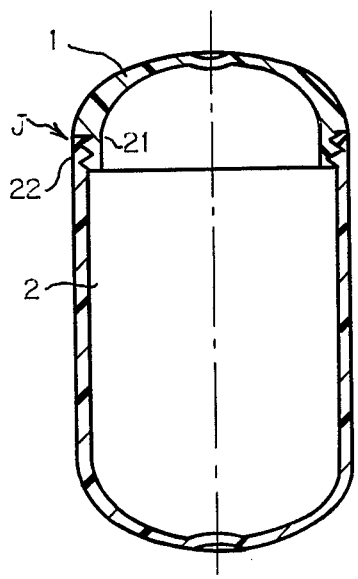
FIG. 21
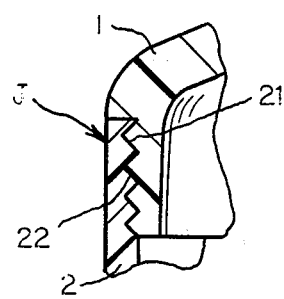
FIG. 22

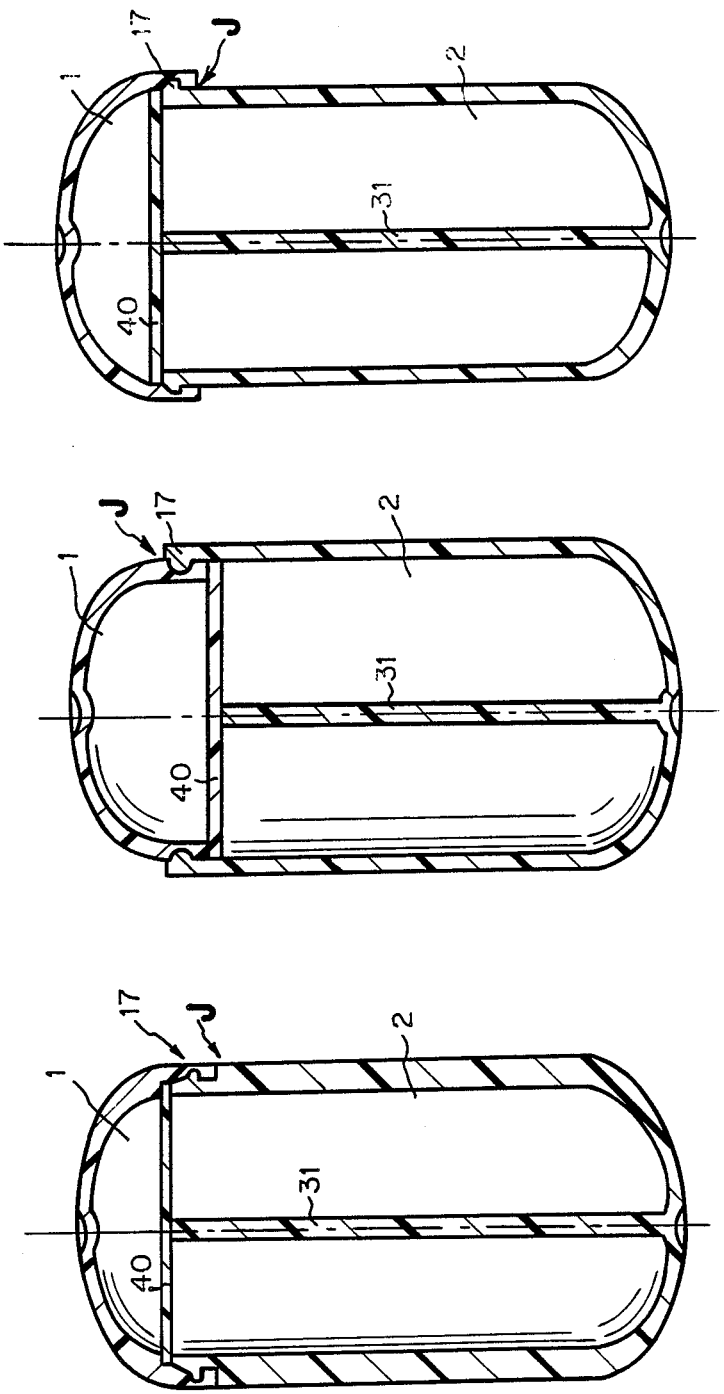

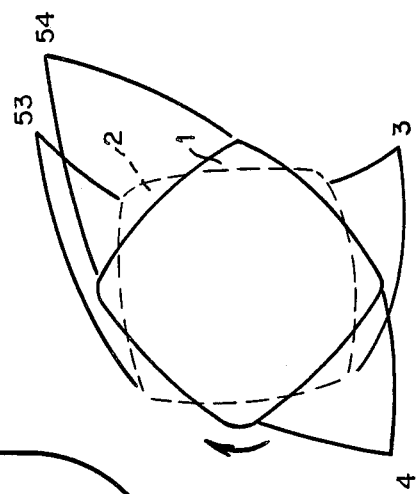
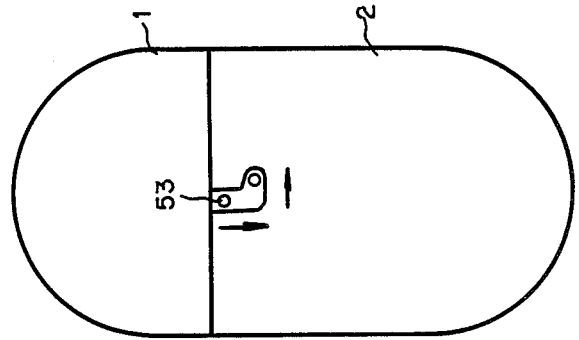
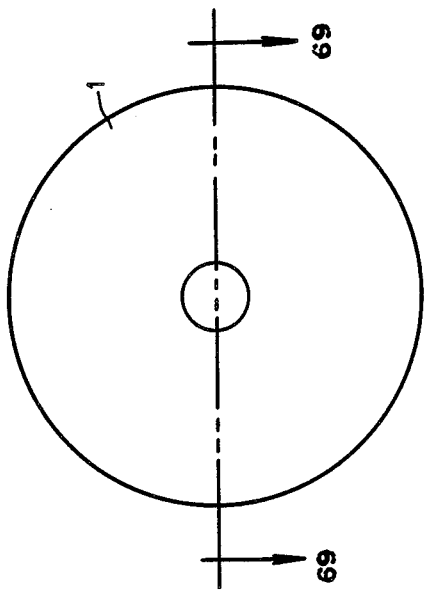
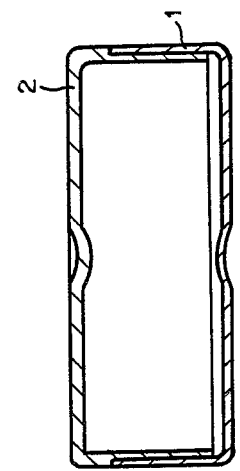
FIG. 71
FIG. 70
FIG. 68
FIG. 69

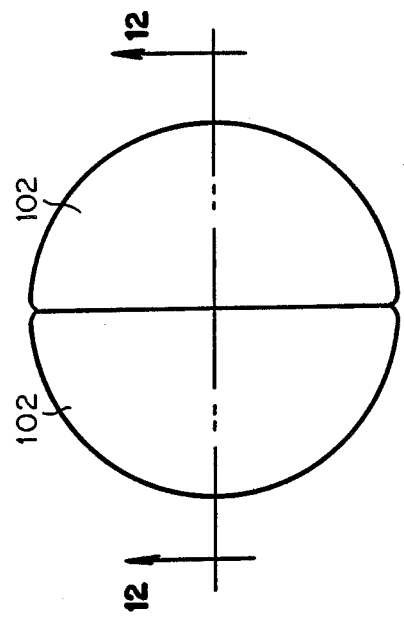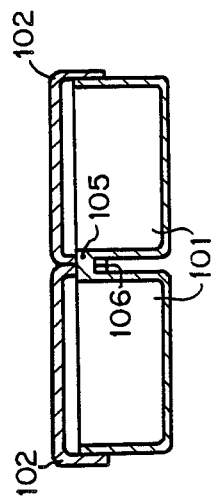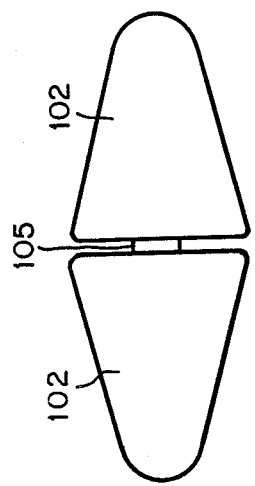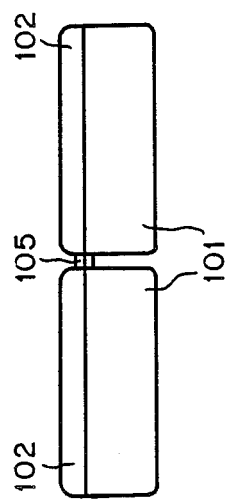

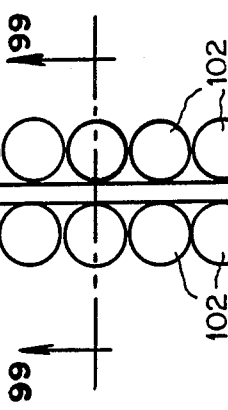
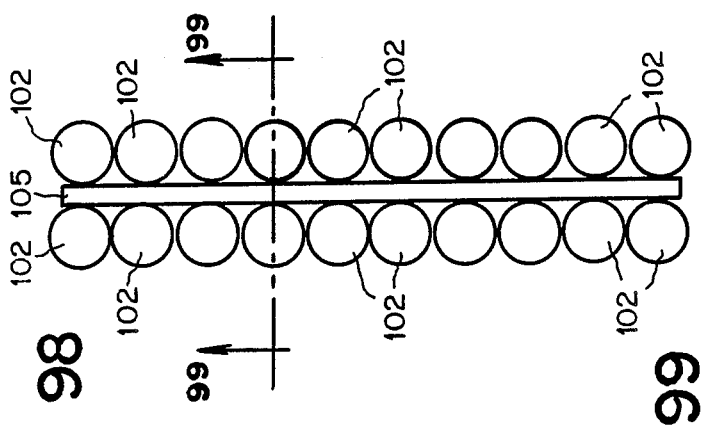
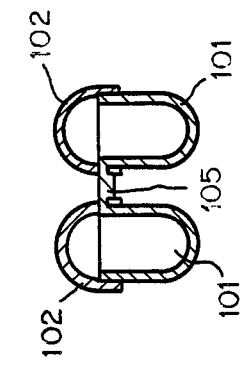
FIG. 98
FIG. 99
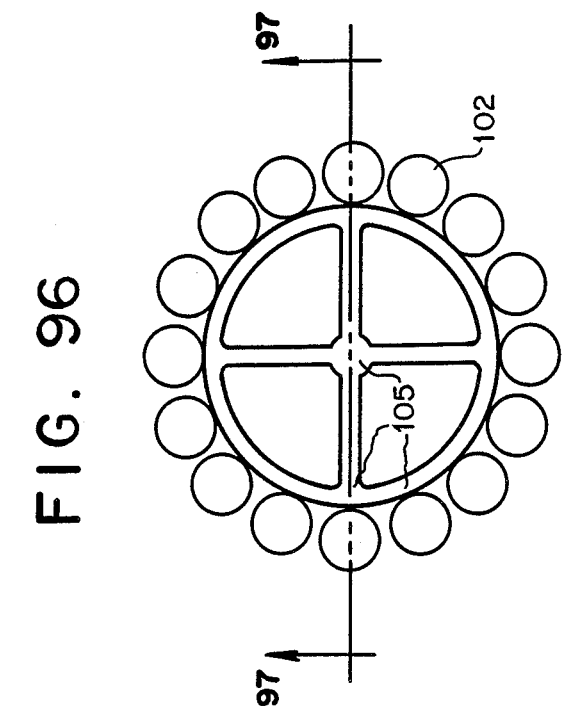
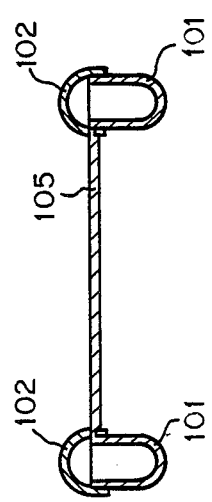
FIG. 96
FIG. 97

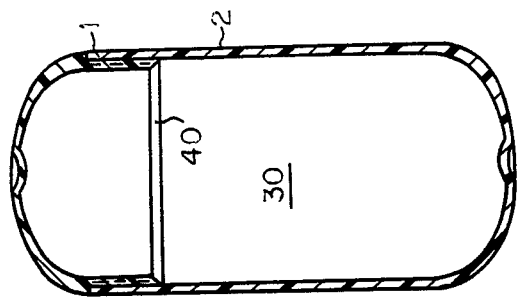
FIG. 113
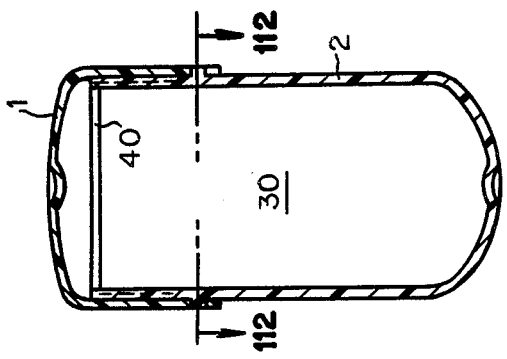
FIG. 111
FIG. 112
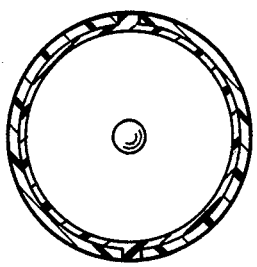
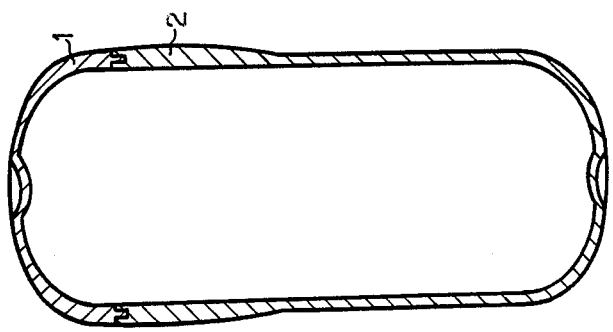
FIG. 110
FIG. 109

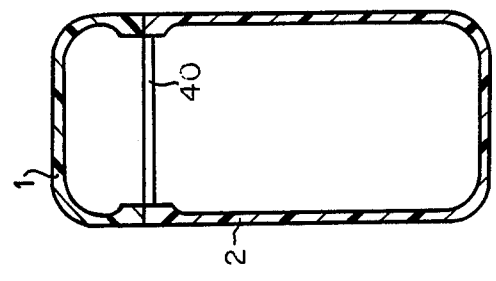
FIG. 116B  FIG. 116A
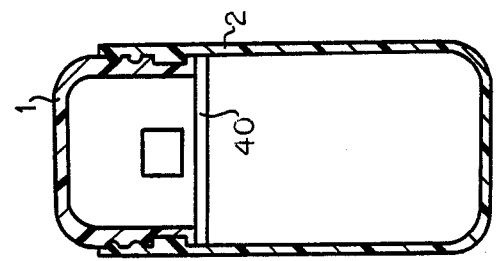
FIG. 115
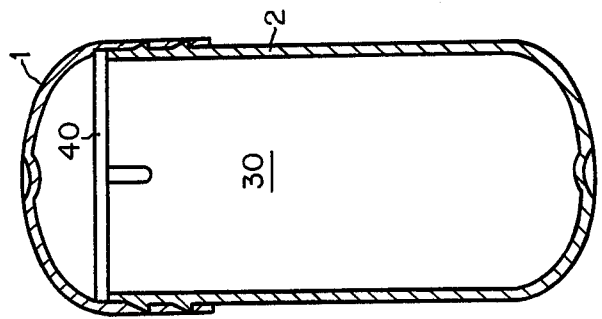
FIG. 114
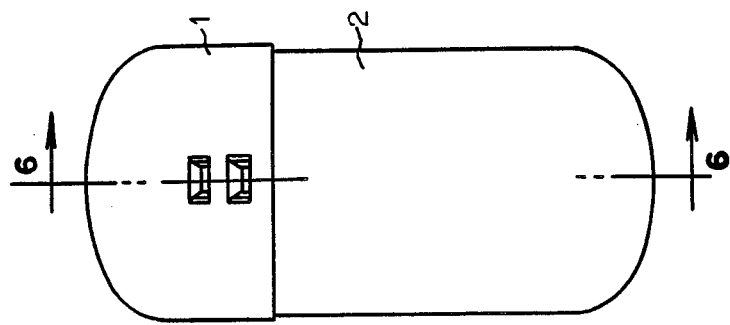

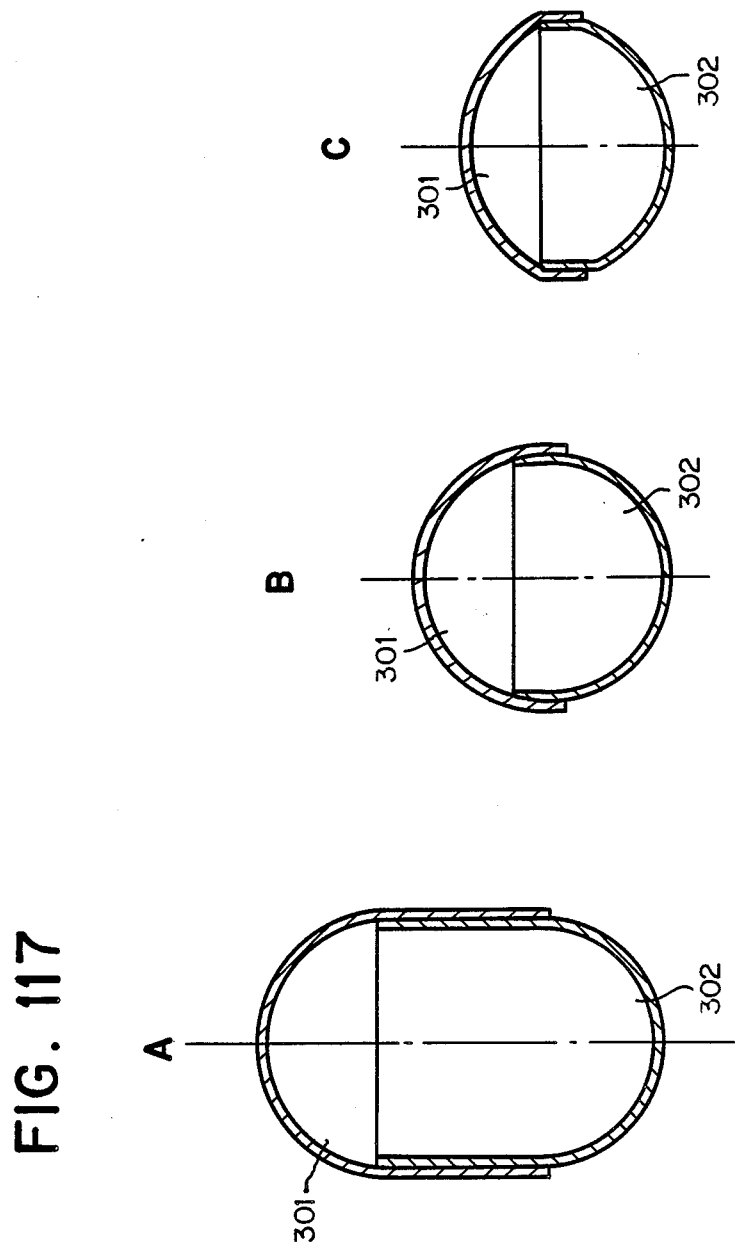

METHOD FOR FORMING PHARMACEUTICAL CAPSULES FROM HYDROPHILIC POLYMERS

CROSS REFERENCE TO RELATED APPLICATIONS

This application is a continuation-in-part of the following applications:

Ser. No. 698,264, filed Feb. 5, 1985, now U.S. Pat. No. 4,665,840;

Ser. No. 641,550, filed Aug. 17, 1984, which is a continuation-in-part of Ser. No. 543,694, filed Oct. 20, 1983 abandoned;

Ser. No. 641,663 filed Aug. 17, 1984, which is a continuation-in-part of Ser. No. 557,306, filed Dec. 2, 1983, now U.S. Pat. No. 4,576,284, Ser. No. 557,502, filed Dec. 2, 1983, abandoned, Ser. No. 557,500, filed Dec. 2, 1983, Ser. No. 543,692, filed Oct. 20, 1983, Ser. No. 543,698, filed Oct. 20, 1983, abandoned, and Ser. No. 543,699, filed Oct. 20, 1983, abandoned;

Ser. No. 641,664, filed Aug. 17, 1984, which is a continuation-in-part of Ser. No. 548,794, filed Nov. 4, 1983, abandoned; and U.S. design application Ser. No. 798,344, filed Nov. 8, 1985, which is a continuation of Ser. No. 451,577, filed Dec. 20, 1982, abandoned.

FIELD OF THE INVENTION

The present invention relates to useful molded products, especially pharmaceutical capsules, prepared by the injection molding of various hydrophilic compositions (i.e., gelatine). The invention particularly concerns injection molded capsules containing one or a plurality of compartments for different dosage forms and having locking means to provide a tamper resistant seal between the cap and body members of the capsule.

BACKGROUND OF THE INVENTION

Capsule-making machines have been developed to utilize dip-molding technology. Such technology involves the dipping of capsule-shaped pins into a gelatin solution, removing the pins from the solution, drying the gelatin on the pins, stripping off the gelatin capsule parts from the pins, adjusting for length, cutting, joining and ejecting the capsules. Prior art capsule-making machines have utilized a combination of mechanical and pneumatic elements to perform these functions in a dip-molding technique. While these apparatus are, in general, suitable for the intended purpose, it is desirable to produce capsules by injection molding them while at the same time precisely controlling the properties of the gelatin in order to produce the capsules hygienically and with minimum dimensional deviations so that the capsules can be filled on the high speed equipment.

A prerequisite for any material to be moldable by an injection process is its ability to pass a glass transition point at a temperature compatible with the thermal stability of the material and the technical possibilities of an injection molding device. A further prerequisite to the use of any material for delivering shaped products of high dimensional stability in an injection molding process is a high minimum elastic recovery after the mold is opened. This parameter can be adjusted by manipulating the dispersity of the material at the molecular level during the injection process.

The following patents describe suitable compounds or mixtures which may be injection molded into various articles.

Shirai et al. in U.S. Pat. No. 4,216,240, describes an injection molding process which produces an oriented fibrous protein product. To obtain a flowable mass for the molding process, the protein mixtures used by Shirai et al. have to be denatured and thus lose their capacity to undergo dissolution.

Nakatsuka et al., in U.S. Pat. No. 4,076,846 uses binary mixtures of starch with salts of protein materials to obtain an edible, shaped article by an injection molding process.

Heusdens et al., in U.S. Pat. No. 3,911,159, discloses the formation of filamentous protein structures which produce edible products.

In addition, the method for determination of the molecular mass distribution of the various types of gelatin used in the present invention is described in the following references:

I. Tomka, *Chimia.* 30, 534–540 (1976)

I. Tomka, et al., *Phot. Sci.* 23, 97 (1975)

The use of an injection molding device for producing capsules of gelatin and other moldable hydrophilic polymers with similar properties, however, is new and has not been suggested in the technical literature.

SUMMARY OF THE INVENTION

The invention relates to useful molded products, especially pharmaceutical capsules, prepared by the injection molding of various gelatin compositions. The invention additionally concerns capsules containing a plurality of compartments for different dosage forms and having various locking means to provide a tamper resistant seal between the cap and body portions of the capsule.

One embodiment of the present invention is an injection molded pharmaceutical capsule for the dosage of solid, creamy or liquid medicaments, exibiting an essentially amorphous polymer structure comprising a cap member and a body member, each having at least one open end, and sidewall means; means located in each sidewall means for connecting the cap and body members together, wherein the connecting means are configured and arranged to face each other in order to achieve, after connection of the cap and body members, a separation resistant connection.

The capsule may be molded from a hydrophilic polymer having a water content of between about 5 and 25 weight percent. The hydrophilic polymer may have a water content of between about 10 and 20 weight percent, preferably ranging between about 14 to 19 weight percent. The finished capsule exhibits a self-sustaining shape as well as negligible reversible elastic deformation of the hydrophilic polymer. An alternate embodiment of the invention may include means such as internal partitions, for forming two or more compartments in the interior spaces defined by the body and cap members.

In a further embodiment of the capsules of the invention, the ratio of the outside diameter of the cap member may be equal to or greater than the overall length of the capsule. Also, the outer surface of the capsule, in the area where the cap and body members are joined together, may be substantially smooth. In capsules having such a configuration, each sidewall is cylindrical and axially joined to the other. In addition, the open end of the cap or body member includes a recessed annular shoulder for receiving the compartment forming means. The depth of this recessed annular shoulder is substantially equal to the thickness of the sidewall means of the cap or body member which does not include this shoulder. Preferably, the open end of each of the cap and body members includes a recessed annular shoulder for receiving compartment forming means.

In another embodiment of the invention, the connecting means is at least one locking means comprising at least one continuous or discontinuous annular ridge located on the sidewall means of either the cap or body member and an annular groove located on the other member. The dimensions of the ridge and groove are preferably substantially equal. Further, each of the sidewall means is structurally and dimensionally adapted so that the ridge cooperates with the groove to form, as noted above, an interlocked capsule when the cap and body members are brought together.

In an alternate embodiment, the sidewall means of the cap and body members each have an open and a closed end. Further, the inner surface of the cap member is located at or below the level of a plane perpendicular to the open end of the sidewall means of the body member such that, after filling the body member with medicaments and closing the capsule, substantially no air is entrapped between the inner surface of the cap member and the medicaments.

In a further embodiment of such a capsule, the cap member is a circular disc which is coaxially joined with the open end of the body member by placing the plane surface of the circular disc in circumferential engagement with the annular periphery of the open end of the body member. Additionally, the cap member may possess an annular recess located at its circumferential edge facing the open end of the body member wherein the sidewall means of the body member mates with and protrudes into this recess.

The cap member may be die-molded directly on to the open end of the body member to serve as stopper means after the body member is filled with medicaments, to seal the medrcaments within the capsu7le. Further, the cap and body members may be di-molded so as to be joinable in a destinctive shape to facilitate the visual and palpable identification of the capsule.

In various alternate embodiments of the invention, some combination of letters and/or numbers may be embossed or debossed upon the surface of the capsule in order to aid in the identification thereof. Further, the seal between the cap member and body member of such capsules may be rendered liquid-proof by wetting the joining surfaces of each member prior to the joining of said members.

Advantageously, the invention provides means for forming two or more compartments in the interior spaces defined by the body and cap members wherein the ratio of the outside diameter of the cap member is equal to or greater than the overall length of the capsule. Preferably, the cap and body members each have an open end and a closed end. The cap member is configured and dimensioned as a closure for the open end of the body member and is directly connected to the body member after the body member has been filled with medicaments so as to retain these medicaments within the capsule. Cover means, such as a circular disc, may be inserted into the open end of the body member after the body member has been filled and before the cap member is connected to it.

By utilizing an alternate construction for these capsules, one may prepare a divisible pharmaceutical capsule dosage form comprising a plurality of connected molded capsules as described above. In this construction, the means for forming two or more compartments comprises a connection which is integrally molded with the body or cap member, or both. This connection is breakable so as to separate the capsule into subunits for administration of the appropriate pharmaceutical dosage.

For capsules of the type described above, one of the cap and body members may be a blister sheet while the other member is a blister sheet cover attached to the blister sheet. In this configuration, the means for connection may comprise lamella means for connecting two individual body or cap member combinations. Further, the compartment forming means may comprise one or a plurality of internal partitions which are integrally molded with the cap or body members.

In an embodiment of the pharmaceutical capsule described herein, one or both of the body and cap members include at least one integrally molded internal partition oriented parallel to the open end and perpendicular to the sidewall of the member. In an alternate arrangement, at least one integrally molded internal partition is oriented perpendicularly to the open end and parallel to the sidewall of the member. Additionally, the open end of the body or cap members, or both, may include closure means which form a closed compartment for retaining different medicaments therein.

The capsules of the present invention are made of a moldable hydrophilic polymer having a water content of between about 5 and 25 weight percent. Preferably, the hydrophilic polymer is a gelatin having a molecular mass between about 10,000 and 2,000,000 Dalton or between about 10,000,000 and 20,000,000 Dalton, with a water content of between about 10 and 20 weight percent. The hydrophilic polymer may also be hydroxypropyl methylcellulose phthalate; polyvinyl acetate phthalate; cellulose acetyl phthalate; an acrylate polymer; a methacrylate polymer; a phthalated gelatin; a succinated gelatin; or a crotonic acid polymer. Further polymers include a vegetable protein; blood protein; an egg protein or an acetylated derivative thereof; a water soluble derivative of cellulose; a water soluble carbohydrate; agar-agar; a water soluble acrylic acid polymer; polyvinyl pyrrolidone; or a vinyl acetate polymer. The gelatin composition may optionally comprise one or more of an extender; a crosslinking agent; a lubricating agent; a dyestuff; or a coloring agent.

The present invention also discloses a method for making these molded pharmaceutical capsules. This method comprises forming an aqueous solution of the hydrophilic polymer or gelatin having a water content of between about 5 and 25 weight percent which optionally contains a predetermined amount of at least one additive selected from an extender, and/or a crosslinking agent, and/or a plasticizing agent, and/or a lubricating agent and/or a coloring agent; maintaining the solution at a predetermined elevated temperature and pressure; injecting a portion of the solution into mold means from the extruder means at an elevated temperature and pressure to shape the capsule members; cooling the capsule members below their glass transition temperature; and ejecting the capsule members from the mold means. By molding in this manner, the capsule members exhibit negligible reversible elastic deformation.

The method for making these capsules may further comprise heating the hydrophilic polymer/water mixture to a temperature between about 50° C. and 190° C. so as to form a melt; maintaining a predetermined water content during the heating; further heating the hydrophilic polymer melt and water to a temperature between about 110° C. and 180° C. in order to dissolve the melt in the water and achieve a homogenous dispersion on a molecular level while maintaining the predetermined water content, injecting the dissolved hydrophilic polymer melt into a mold cavity while maintaining the predetermined water content; cooling the hydrophilic product having an essentially amorphous polymer structure at a temperature below the glass transition range of the hydrophilic polymer while maintaining the predetermined water content and ejecting the molded product of the hydrophilic polymer from the mold whereby the injection molded capsule exhibits a self-sustaining shape and negligible reversible elastic deformation of the hydrophilic polymer.

Advantageously, the hydrophilic polymer is maintained at a temperature of between about 110° C. and 180° C. and at a pressure of between about $6 \times 10^7$ and $3 \times 10^8$ N/m². Also, the crosslinking agent should be added to the solution just prior to the injecting step.

Those skilled in the art will be able to form gelatin capsules by die-molding, i.e., profile extrusion, compression molding, vacuum forming, thermal forming, extrusion molding or polymer casting in combination with vacuum forming. The most preferred method, however, is injection-molding.

BRIEF DESCRIPTION OF THE DRAWINGS

Further benefits and advantages of the invention will become apparent from a consideration of the following description given with reference to the accompanying drawing figures which specify and show preferred embodiments of the present invention.

FIGS. 3(A-C) are three sectional views of alternate locking arrangements for the capsule of FIG. 1(D);

FIG. 15 is a cross-sectional view of a capsule provided with a locking window;

FIGS. 16 to 20 are partial cross-sectional views showing further embodiments of the locking window of FIG. 15;

FIG. 22 is a partial cross-sectional enlargement of FIG. 21;

FIGS. 25 to 38 are cross-sectional views of various capsules according to the invention;

FIGS. 66 and 68 are side views of capsules which provide for a varying volume of contents;

FIGS. 67 and 69 are cross-sectional views taken along line 67—67 of FIG. 66 and 69—69 of FIG. 68, respectively;

FIG. 70 is a side view of a capsule having a shape which enables precise positioning on a joining machine;

FIG. 71 is a top plan view of the capsule of FIG. 70;

FIGS. 80–85 depict alternate embodiments of a divisible capsule wherein the body and cap parts are joined by a connecting lamella;

FIG. 96 depicts a top plan view of another capsule package configuration;

FIG. 97 is a sectional view of the capsule package of FIG. 96 taken along line 97—97;

FIG. 98 depicts a top plan view of an alternate capsule package configuration;

FIG. 99 is a sectional view of the capsule package of FIG. 98 taken along line 99—99;

FIGS. 106-109 are cross-sectional views showing four alternate embodiments of locking means for the capsules of the present invention;

FIG. 110 is a top plan view of another capsule having locking means;

FIG. 111 is a cross-sectional view of the capsule of FIG. 110 taken along line 111—111;

FIG. 112 is a cross-sectional view of the capsule of FIG. 111 taken along line 112—112;

FIG. 113 is a cross-sectional view of the locking means of another capsule;

FIG. 114 is a top plan view of a capsule embodiment having two locking windows located in the cap portion;

FIG. 115 is a cross-sectional view of the capsule of FIG. 114 taken along lines 115—115;

FIGS. 116(A) and (B) are cross-sectional views of alternate locking arrangements for various capsules;

FIGS. 117(A), (B) and (C) are cross sectional views of capsules configured so that their diameters are less than their length;

FIG. 118A is a schematic showing a combined injection molding device-microprocessor apparatus for making capsule parts;

DETAILED DESCRIPTION OF THE PREFERRED EMBODIMENTS

Figure 1:
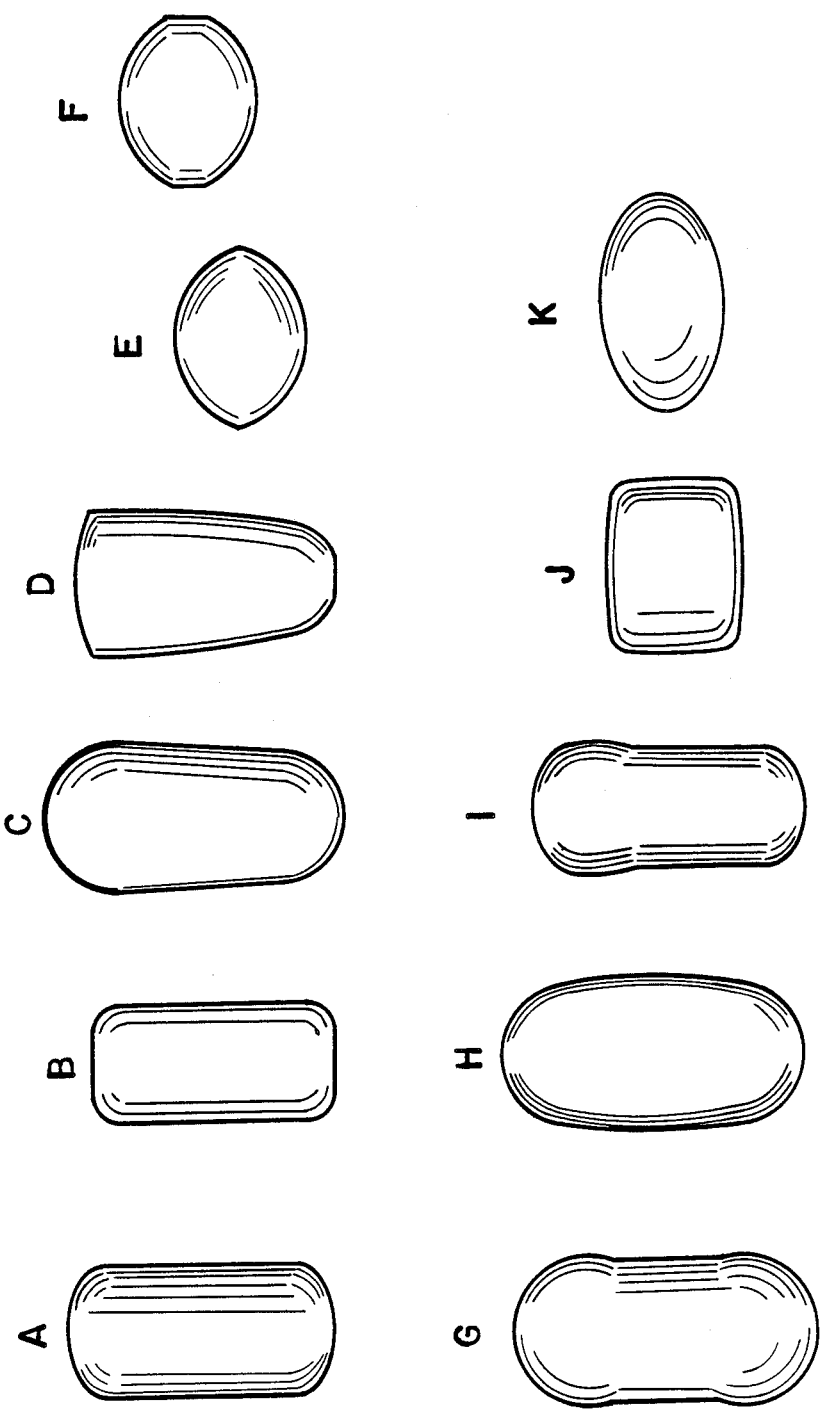
FIGS. 1(A-K) are top plan views showing eleven embodiments for the outward appearance of capsules constructed according to the present invention.

The present invention concerns die-molded articles, especially injection molded capsules, which have a body part and a cap part, each having a side wall, and open and closed ends, the two parts being joinable, characterized in that the capsule is made:

(i) from a hydrophilic polymer composition or a mixture of such polymers having a water content of 5-25% by weight (calculated to the hydrophilic polymer composition) and preferably from a gelatin composition having a water content of 10-20% by weight (calculated to the gelatin composition): and/or (ii) by high speed die pressure molding; and (iii) that each of said cap and body parts has in the side wall area, adjacent to its open end, at least one locking means being arranged to face each other and to achieve, after joining of said parts, a separation-resistant connection; the capsule having a plurality of compartments, with the cap and body parts being worked at a precision of ±0.01% and the capsule being stable in dimension.

Capsules prepared by the present invention have the further advantage that they can be die-molded so as to be joined in a distinctive shape to provide an immediate visual identification of the capsule. It is also possible to prepare capsules using the present invention wherein the cap and/or the body have embossed printing of letters thereon.

A further embodiment of this invention is the complete liquid proof sealing of the cap and body parts by wetting the joining surfaces with water.

When in the description the term "gelatin" is used, other hydrophilic polymer compositions whose properties are acceptable as capsule materials are also included. Hydrophilic polymers are polymers with molecular masses ranging from approximately $10^3$ to $10^7$ Dalton carrying molecular groups in their backbone and/or in their side chains and capable of forming and/or participating in hydrogen bridges. Such hydrophilic polymers exhibit in their water adsorption isotherm (in the temperature range between approximately 0° to 200° C.) an inflection point close to the water activity point at 0.5.

Hydrophilic polymers are distinguished from the group called hydrocolloids by their molecular dispersity. For the maintenance of the molecular dispersity of these hydrophilic polymers, a fraction of water, —determined according to the working range of the present invention 5 to 25% by weight of said hydrophilic polymers must be included provided that the temperature of said hydrophilic polymers in the working range between 50° and 190° C. of the present invention.

Gelatin as a preferred hydrophilic polymer is made from various types of gelatin, including acid or alkaline processed ossein, acid processed pigskin, or alkaline processed cattle hide. Said types of gelatin have a molecular preferably in the mass range of 10.000 to $2 \times 10^7$ Dalton or a molecular mass range of 10.000 to $2 \times 10^6$ and $10 \times 10^6$ to $20 \times 10^6$ Dalton. It has a water content of preferably 10-19% and especially 12-18% by weight calculated to the gelatin.

There are other hydrocolloids, not hydrophilic polymers in the sense of this definition, which contain more or less spherical or fibrous particles, whereby those particles are composed of several macromolecules of a hydrophilic polymer within the molecular mass range of $10^3$–$10^7$ Dalton giving rise to particle sizes between 0.01–10 microns. This is the typical range for colloidal particles.

Referring now to FIGS. 1 (A-K), there are illustrated eleven alternate embodiments for the external appearance of the capsule of the present invention. While one skilled in the art may be able to suggest a number of additional capsule shapes embodying applicants' invention, those depicted herein are illustrated as representative of several classes of such a distinctive outward appearance.

Figure 2:
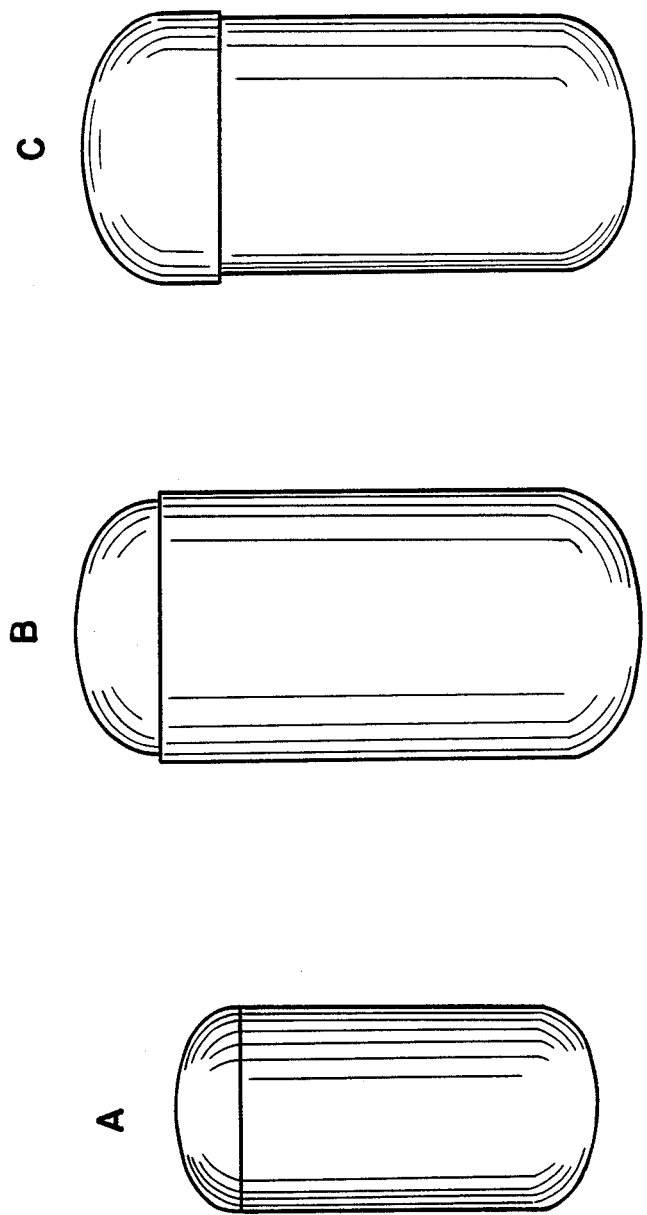
FIGS. 2(A-C) are top plan views of three embodiments for joining the cap and body members of these capsules.

FIGS. 2 (A-C) illustrate three basic embodiments into which the outward appearance of the capsule produced by applicants' invention may be classified. FIG. 2A depicts a capsule having a cap 1 and a body 2 of equivalent width. In FIG. 2B, the cap member 1 is narrower than body 2, while, in FIG. 2C, the cap 1 is wider than body 2.

In FIG. 3A there is shown an embodiment of a capsule which might be filled with a pharmaceutical product to be swallowed by the patient. In this embodiment the cap 1 is formed by die-molding, to provide a smooth outer surface when joined within the body portion 2., i.e. it has the same diameter as the capsule body 2 which is filled with the contents 30.

FIG. 3(B) shows another embodiment wherein body 2 is provided with groove 4 to maintain a tight seal with cap 1 when the parts are joined.

In FIG. 3(C) there is shown a further embodiment wherein a flat, circular plate or disc 40 is inserted into body 2, so as to completely cover filling material 30. In this embodiment cap 1 is formed by die-molding so as to provide a smooth outer surface when joined with body 2, i.e., it has the same outer diameter as capsule body 2 which is filled with the medicinal contents 30. The cover plate 4 will permit injection molding of the cap at a very high speed.

Due to manufacturing limitations imposed by current dip-molding processes, capsules produced thereby have a disadvantage in that they do not have secure locking means to prevent separation after filling and joining. There is a problem if such a capsule, especially one containing food or drugs, can be opened or tampered with.

The present invention provides for molding high precision locking articles, especially capsules which are liquid- and tamper-proof. In this application a "locking capsule" is defined to include a filled and joined capsule wherein the capsule parts are formed so as to impede their separation or tampering with the contents.

Figure 4:
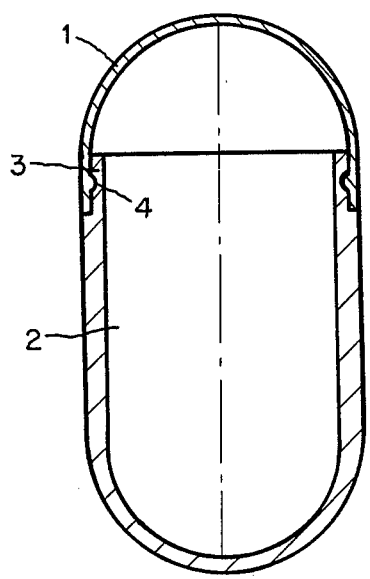
FIG. 4 is a cross-sectional view of another capsule of the invention.

The capsule shown in FIG. 4 has a cap 1 and a body 2. The cap 1 has an annular ridge 3 protruding from the inner surface of the side wall adjacent to the open end of the body 2. Ridge 3 mates with a recessed annular groove 4 of body 2. The ridge 3 and groove 4 are structurally and dimensionally adapted so that they are interlocked by snap-in action when the capsule parts are joined. It is to be understood that:

the ridge 3 may be a continuous ring or it may constitute a number of segments or cams cooperating with a continuous or discontinuous groove;

the locking means may comprise one or more ridge and groove structures; and/or the cross-sectional shape of the locking means may comprise not only semicircular forms but any other suitable form such as a triangle, a semi-oval or other fractions or circles, ovals, rectangles, squares, triangles or other polygonal shapes.

Figure 5:
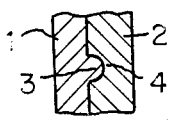
FIGS. 5 to 14 are partial cross-sectional views showing further embodiments of capsule locking mechanisms according to the invention.
Figure 6:
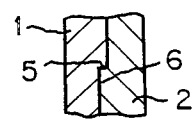
Figure 7:
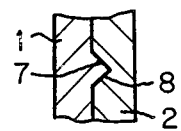

FIGS. 5 to 14 are alternate embodiments of the capsule shown in FIG. 4. In FIG. 5, the cap 1 has a semi-circular groove 3 which mates with a complimentary ridge 4 of body 2. In FIG. 6 the cap 1 has a right angle groove 5 which mates with a right angle ridge 6 of body 2. FIG. 7 shows a further embodiment wherein the cap 1 has an annular conical ridge 7 which mates and locks with an annular conical groove 8 on body 2.

Figure 8:
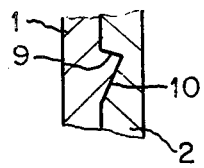

FIG. 8 shows another capsule wherein the cap 1 has an annular triangular ridge 9 which mates and locks with a corresponding annular triangular groove 10 on body 2. It has been found that the optimum locking force occurs when the short side of the triangular ridge 9 faces the open end of the other part. For better locking, therefore, the short side of the triangular ridge 9 faces the short side of the triangular groove 10. The joining of the capsule parts is facilitated when the shortest side of the triangular ridge facing the open end of the other capsule part forms, with the adjacent side wall, an angle of about 134 to 190 degrees.

Figure 9:

FIG. 9 shows another cap 1 having a triangular ridge 9 in mating and locking engagement with a triangular groove 10 on body 2.

Figure 10:
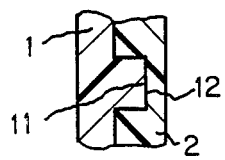

FIG. 10 shows a cap 1 having an annular rectangular ring 11 in mating and locking engagement with a corresponding annular rectangular groove 12 on body 2.

Figure 11:
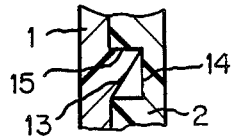

FIG. 11 shows a cap 1 having an annular ridge with a triangular cross section 13 wherein the shortest face of the triangle 15 mates and locks with the top surface of a rectangular groove 14 in body 2.

Figure 12:
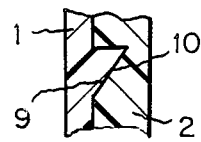

FIG. 12 shows another embodiment of a cap 1 having a triangular ridge 9 in mating configuration with a triangular groove 10 on body 2.

Figure 13:

FIG. 13 shows a cap 1 having a ridge 15 with a bead-like cross sectional area in mating and locking engagement with a corresponding annular groove 16 having a corresponding cross sectional area on body 2.

Figure 14:
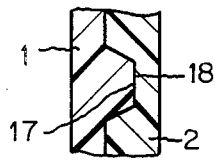

FIG. 14 is another embodiment showing a cap 1 having an annular ridge 17 with a generally parallel-epipedonal cross sectional area which mates and locks with an annular groove 18 having a corresponding parallel-epipedonal cross sectional area on body 2.

FIG. 15 is another embodiment of the invention showing a cap 1 having one or more windows 20 arranged on its cylindrical side walls near the open end on a circular path which is coaxial with the axis of the capsule. The body 2 has a corresponding number of locking cams 19 which are protuberances located on its cylindrical side walls near its open end. These cams 19 mate with the windows 20 in locking engagement when the capsule parts are joined.

FIGS. 16 to 20 show alternate embodiments of the locking window 20 and cam 19 of FIG. 15: in FIG. 16, the cross sectional area is rectangular; in FIG. 17, circular; in FIGS. 18 and 19, triangular; and in FIG. 20, oval.

FIG. 21 shows an alternate embodiment of the present invention wherein the cap 1 has a male thread 21 on the outside surface of its cylindrical side walls at its open end. The male thread 21 engages with a female thread 22 on the inside surface of the body 2 at its open end. It is another feature of this embodiment that the body 2 and the cap 1 can be joined with an smooth outside surface, as at J, so as to make separation more difficult, thereby enhancing the locking feature of the capsule.

FIG. 22 is a partial enlargement of FIG. 21 showing the mating engagement of the male thread 21 with the female thread 22 in the vicinity of the smooth surface at the joining area, J.

Figure 23:
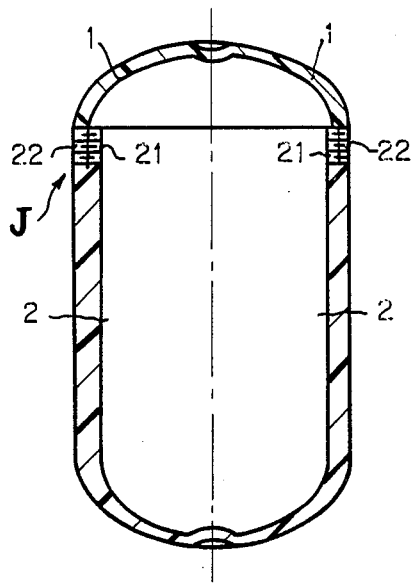
FIG. 23 is a cross-sectional view of another capsule.

FIG. 23 is an alternate embodiment of FIG. 21 wherein the body 2 has a male thread at the outside surface of its open end. The male thread 21 mates and engages with a female thread 22 on the inside surface at the open end of cap 1.

Figure 24:
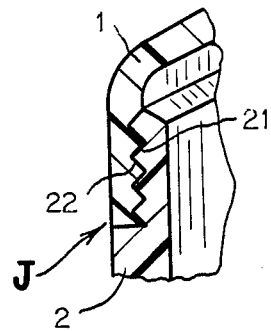
FIG. 24 is a partial cross-sectional enlargement of FIG. 23.

FIG. 24 is a partial enlargement of FIG. 23 showing the smooth surface at the joining area, J.

Figure 25:
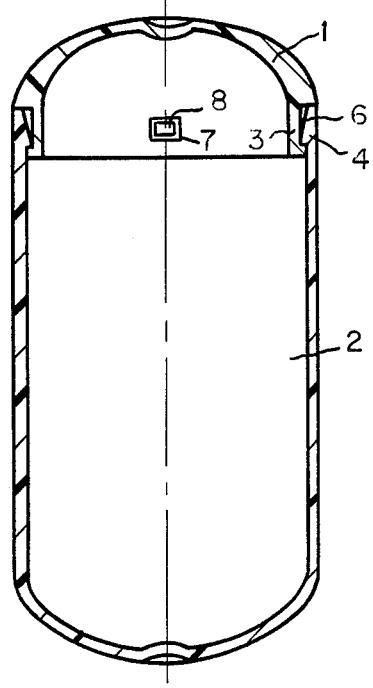

FIG. 25 shows a further embodiment of the invention having a bayonet-type locking arrangement wherein the cap 1 has an annular rectangular groove 3 adjacent to the open end of the cap 1 in a direction generally parallel to the capsule axis. The body 2 has a triangular ridge 4 on the inside surface at the open end of body 2. The triangular ridge 4 has a conical taper 6 at its leading edge in order that the open end of body 2 can enter more easily within cap 1. In addition, cap 1 has a window 7 for mating with a protruding cam 8 on body 2. The combination of the groove 3 in engagement with ridge 4 plus the engagement of window 7 with cam 8 provides a secure bayonet-type lock.

Figure 26:
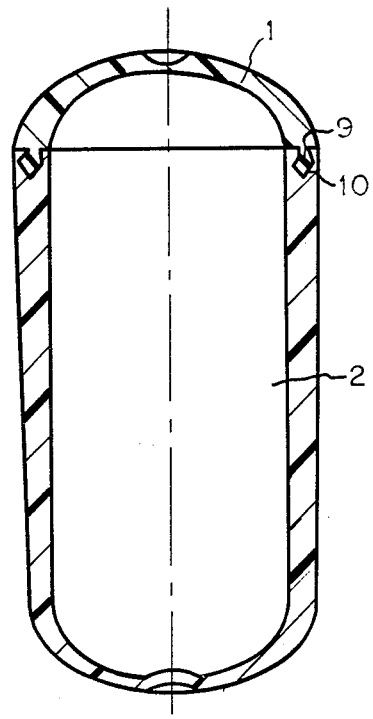

FIG. 26 depicts an alternate embodiment of the invention wherein the cap 1 has an annular dove-tail ring 9 on its cylindrical side wall at its open end for mating engagement with a dove-tailed groove 10 on the cylindrical side wall at the open end of the body 2.

Figure 27:
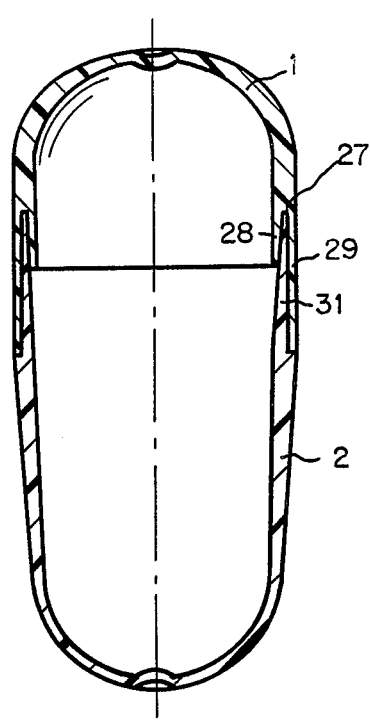

FIG. 27 shows an alternate embodiment of the invention wherein the cap 1 is provided, on its cylindrical side wall at its open end, with an annular slit 27 which is symmetrically arranged with respect to the main axis of the capsule. The slit 27 is defined by two annular wall parts 28, 29 of different lengths. The body 2 has an upright side wall 31 of reduced thickness which tapers towards its open end. In the joined position, as shown in FIG. 27, the side wall 31 of the body 2 is held by flexible pressure in the annular slit 27 which preferably has a correspondingly tapered configuration.

Figure 28:
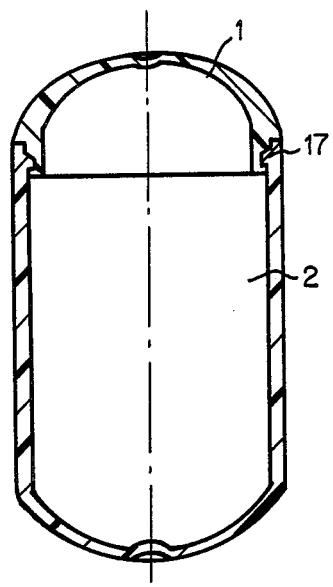
Figure 29:
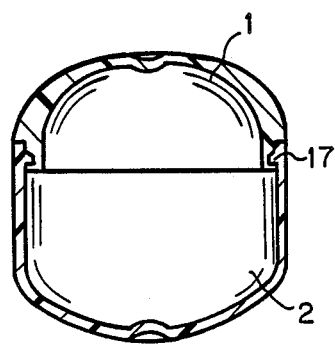
Figure 30:
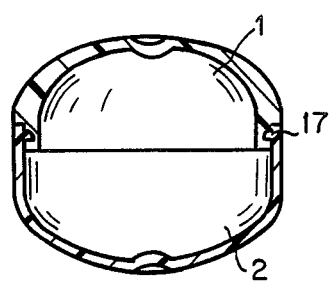

According to FIGS. 28, 29 and 30, a capsule is shown having a cap 1 joined with a body 2. At the joining area a locking means, as at 17, is provided in accordance with the embodiments previously disclosed. It is a feature of the present invention that the ratio can be variable between the outside diameter of the cylindrical side walls (D) and the overall length of the joined capsule (L). FIG. 28 shows the capsule wherein the ratio of D to L is less than one. In FIG. 29, the capsule has a ratio of equal to one, while in FIG. 30, the ratio is greater than one. The advantages of a variable D to L ratio are that:

The volumetric contents of the capsule can be changed to meet particular requirements, especially for pharmaceutical and food use; and the configuration can be varied to enable easier swallowing of the capsule, especially for pharmaceutical and food use, with children, adults and geriatric patients, who differ markedly in their ability to swallow capsules.

It is most advantageous, however, to utilize a capsule having a D to L ratio of equal to or greater than one.

FIGS. 31, 32 and 33 show different embodiments of the invention having a cap 1 and a body 2 with a locking means, 17, in accordance with the embodiments previously disclosed. Each of these embodiments is constructed with a longitudinal partition 31 oriented parallel to the length of the capsule in order to divide body 2 into a plurality of compartments. If desired, each compartment may then be filled with a different medicament in various therapeutic dosages. Across the top of body 2 may be fitted a cover plate 40 in the form of a disc for preventing the interaction of entrapped air with the medicaments contained therein, certain of which may be deleteriously affected by contact with air.

FIG. 31 shows, as a feature of the present invention, that the locking means 17 can also be utilized with a capsule having a smooth outside surface at the joinder, J. FIG. 32 shows a capsule as described above having a body 2 with a protruding edge at the joinder, J, while FIG. 33 shows a capsule as described above having a cap 1 with another protruding edge at J.

Figure 34:
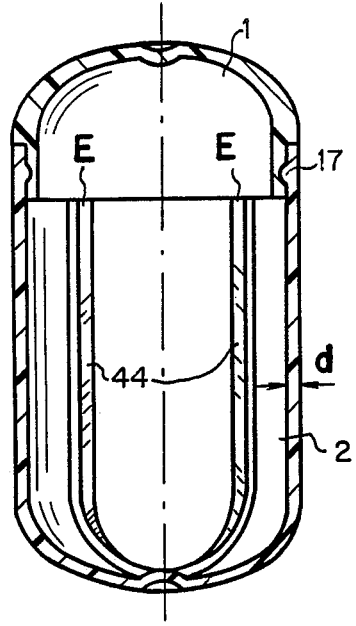

FIG. 34 shows a further embodiment of the present invention. The cap 1 and the body 2 have locking means 17, as previously disclosed. In addition, the body 2 has on its side wall inner surface, a number of reinforcing ribs 44 which are molded so as to protrude from the inner side wall surface. The ribs 44 preferably extend over the whole length of the body 2 and join each other in the center of the closed end of the body 2. In the construction of ribs 44, which may have triangular, rectangular or other cross sections, the bending strength or rigidity of the body 2 is increased to such an extent that the wall thickness D may be substantially reduced. In addition, the end faces E of the ribs 44 form a stop and support means for the cap 1. The body 2 may be manufactured by injection molding, and the ribs 44 constitute a flow path for the injected materials so that the quick and regular distribution of the material is facilitated within the injection mold.

Alternatively, the ribs 44 in the above figure could be undercut into the side of one or both parts so as to improve the disintegration of the capsule in the gastrointestinal tract of the patient. Also, the ribs 44 could be molded with and protruded from the side wall outer surface of the body 2.

Figure 35:
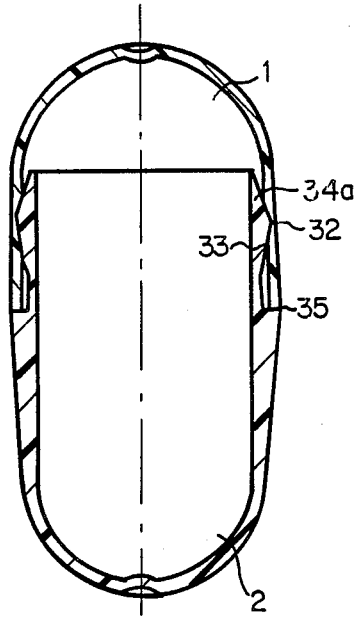

In the embodiment of FIG. 35, cap 1 has, on the inner surface of its cylindrical side wall, an annular groove 32 for receiving a conically shaped portion 33 of the cylindrical side wall of body 2. The open end of cap 1 rests upon the annular surface 35 of a shoulder formed in side wall of the body 2. Joining of the cap 1 and body 2 is facilitated by tapered closed end 34 of body 2.

Figure 36:
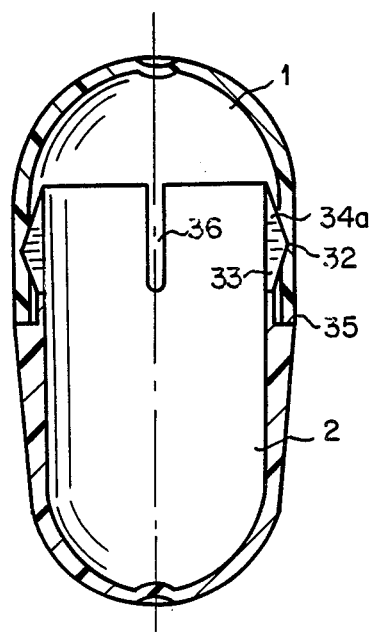

In FIG. 36 the reference numerals of FIG. 35 are used for all parts which have remained unchanged. The cap 1 is identical to that shown in FIG. 35. However, the body 2 is additionally provided with a slit 36 (one or more circumferentially arranged slits may be provided) which confers upon the open end of the body a greater flexibility thereby assisting and simplifying the joining of cap 1 and body 2.

Figure 37:
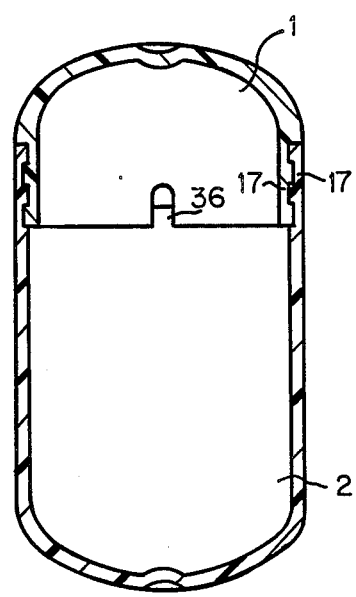

FIG. 37 illustrates an alternate embodiment of the present invention wherein cap 1 and body 2 are provided with two or more locking means 17. In addition, the cap 1 is provided with slit means 36 for greater flexibility which assists and simplifies the joining operation of cap 1 and body 2.

Figure 38:
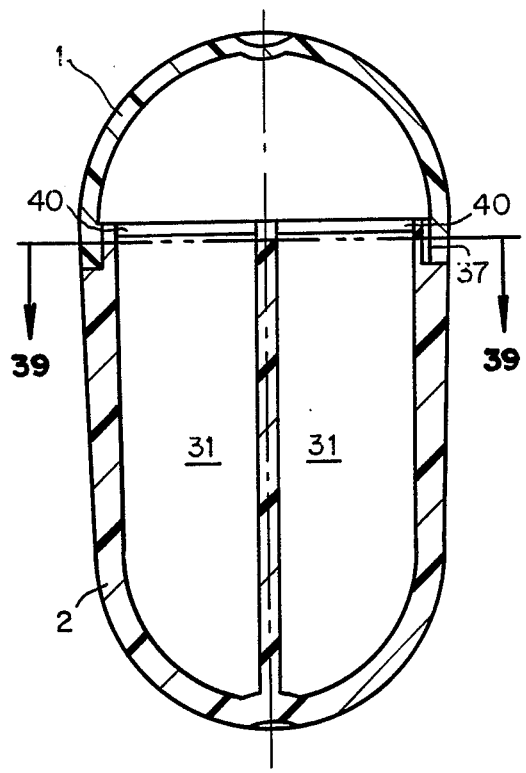

FIG. 38 shows an alternative embodiment of the capsule depicted in FIGS. 31-33 wherein body 2 is divided into at least four separate compartments by the presence of at least two longitudinal partitions 31, positioned perpendicularly to one another along the longitudinal axis of the capsule. These compartments may be filled with the same or complimentary medicaments 30 which are protected from mixing with one another and also from interacting with air entrapped within the capsule by the provision of a disc-like cover plate 40. In addition, as an alternate method for securing a locking engagement, cap 1 and body 2 are each provided with one or more ratchet teeth 37 on their surfaces facing each other, as shown in FIG. 39.

Figure 39:
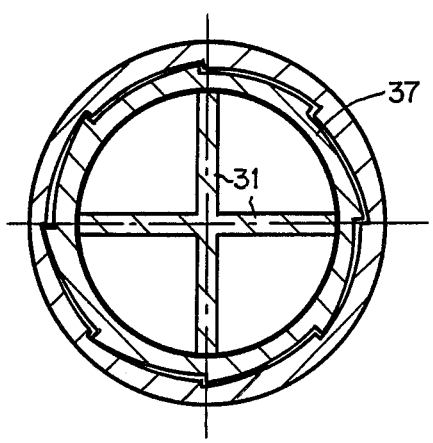
FIG. 39 is a cross-sectional view along line 39—39 of FIG. 38.

FIG. 39 is a sectional view of FIG. 38 showing the teeth 37 in mating engagement.

Figure 40:
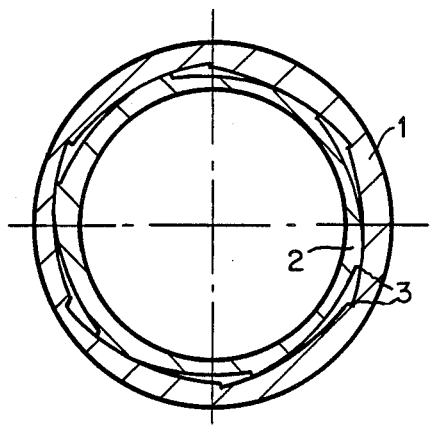
FIG. 40 is a view of FIG. 39 wherein one capsule part is axially rotated with respect to the other capsule part.

FIG. 40 is an alternate sectional view of FIG. 38 showing teeth 37 when not in mating engagement with each other. The application of torque by coaxial rotation of one of the capsule parts around the other causes a frictional locking engagement of the teeth 37 of one capsule part upon the mating surface of the other capsule part.

Figure 41:
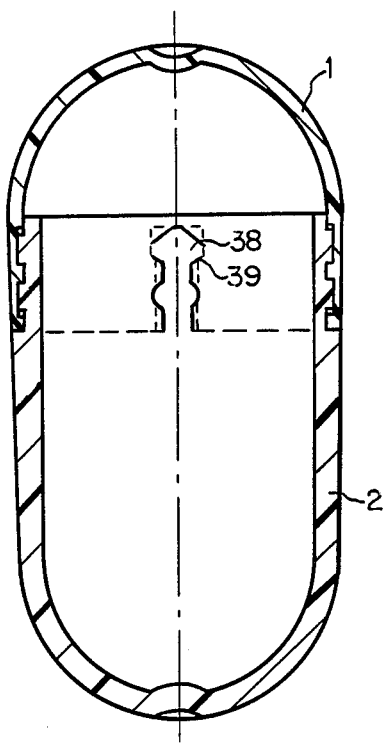
FIG. 41 is a side view of another capsule.

FIG. 41 is a side view of a further embodiment of the present invention wherein the body 2 is provided with one or more protrusions 38 on the outside surface of its side wall adjacent the open end which snap into locking engagement with one or more corresponding recesses 39 in the side wall of the cap 1.

Figure 42:
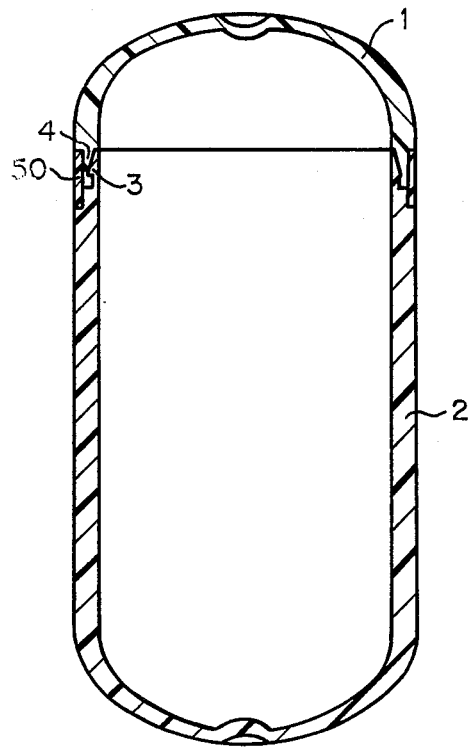
FIGS. 42 and 43 are cross-sectional views of additional capsules.
Figure 43:
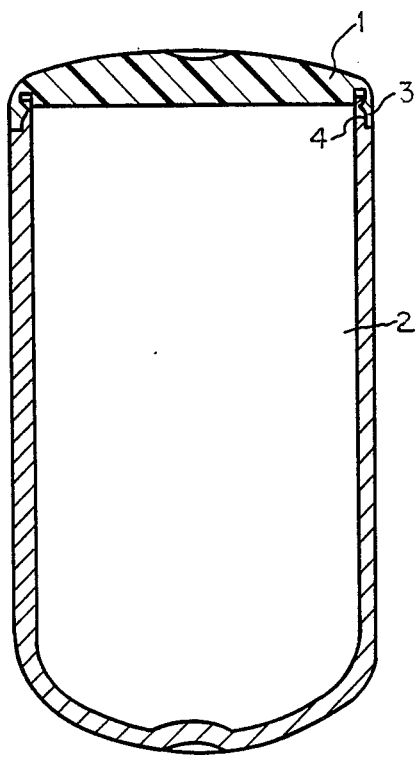
Figure 42A:
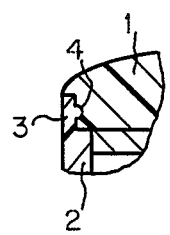
FIGS. 42(A) and 43(A) are partial cross-sectional views of the capsules of FIGS. 42 and 43, respectively.
Figure 43A:
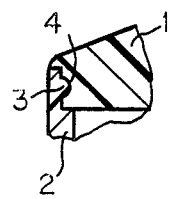

FIG. 42 is a still further embodiment of the capsule of the invention showing cap 1 and body 2 in locking engagement; both the cap 1 and the body 2 have a recessed groove 4 in the joining area which is filled by a band 50 of sealing or bonding material.

In any of the above embodiments, the body 2 may have a reduced diameter at the open end to facilitate entry during joining with cap 1.

FIGS. 4-31 and 34-44 show that the outside surface of the injection molded capsule is smooth in the joining area of cap 1 and body 2.

Capsules manufactured by prior-art dip-molding processes, have the following disadvantages:

the air trapped in the spherical closed end of the cap of a filled and closed capsule results in a moving bubble of air when the content is a liquid;

numerous capsule contents, especially those which are creamy or liquid, deteriorate after exposure to the oxygen in the trapped air;

such capsules are neither liquid-nor gas-tight;

the capsules are neither tamper-proof nor separation-resistant. There is a disadvantage if such a capsule, especially one containing food or drugs, can be opened or tampered with; and when used for pharmaceutical purposes, the protruding edge located on the periphery of the open end of the capsule is relatively sharp. The removal of that protruding edge would make the capsule more attractive to swallow.

numerous capsule contents, especially those which are creamy or liquid, deteriorate after exposure to the oxygen in the trapped air;

such capsules are neither liquid nor gas-tight;

the capsules are neither tamper-proof nor separation-resistant. There is a disadvantage if such a capsule, especially one containing food or drugs, can be opened or tampered with; and when used for pharmaceutical purposes, the protruding edge located on the periphery of the open end of the capsule is relatively sharp. The removal of that protruding edge would make the capsule more attractive to swallow.

In comparison thereto, the present invention provides a capsule having a structrual configuration which avoids the aforementioned disadvantages. The capsules of the present invention, in addition to being separation resistant, avoid the entrapment of air during filling.

FIGS. 42, 42A, 43 and 43A show additional views of alternate locking devices. Any of the disclosed locking devices may be used on any of the capsule shapes depicted in this specification.

The present invention also permits the preparation of distinctive capsule shapes by die-pressure molding of the above described materials.

Prior art pharmaceutical capsules have axially joinable cylindrical cap and body parts which require that the inner diameter of the cap side wall frictionally engages the outer diameter of the body side wall. When the cap and body are joined, the open end of the cap forms a relatively sharp protruding edge. The prior art capsules have the following principal disadvantages:

due to limitations of manufacture by conventional dip-molding processes, the prior art capsules cannot differ much in shape and are, therefore, not very adaptable;

identification of the capsule contents must be indicated by means of different colors and imprinting, i.e. only by visual means, and not be a combination of visual means and palpable characteristics; and confusion of prior art capsules with different contents may occur because of the limited number of distinctive shapes available.

These principal disadvantages are becoming more serious because the number of oral medications is increasing and there are only a limited number of visual means available for identification.

In addition, prior art capsules have the following further limitations:

they cannot be provided with a smooth outer surface which would render them easy-to-swallow; and they have a relatively large empty space which leads to a waste of material and of package volume.

It is therefore an object of the present invention to provide a capsule which has an adapted shape so as to avoid the aforementioned disadvantages and limitations. In view of the above, it is convenient to group several of the embodiments of the present invention into the categories:

1. Capsules with a shape which is distinctive

The distinctively shaped capsules of this group help to avoid confusion and to support the visual identification of the capsule. For convenience, all of the figures in this application use the same reference numerals.

Figure 46:
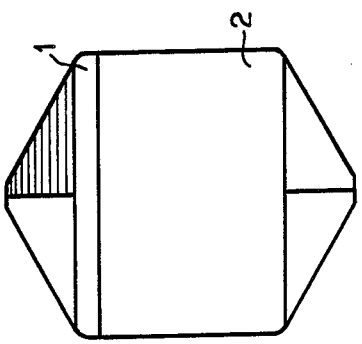
Figure 47:
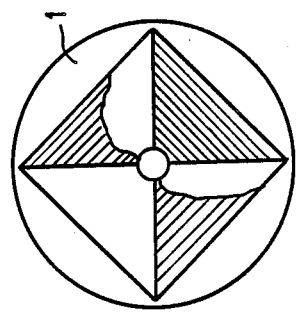
Figure 44:
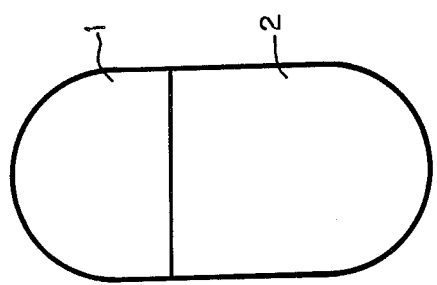
Figure 45:
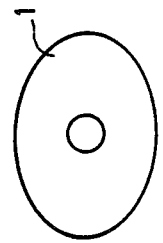

FIGS. 44 and 45 illustrate a distinctive oval-shaped capsule of the present invention having a cap 1 and a body 2. FIGS. 46 and 47 illustrate a pyramidical end-shaped capsule.

Figure 49:
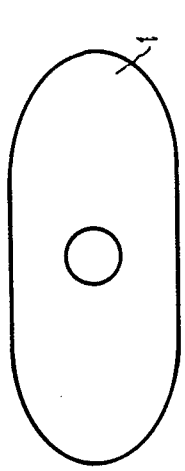
FIGS. 45, 47 and 49 are top plan views of the capsules of FIGS. 44, 46 and 48, respectively.
Figure 48:
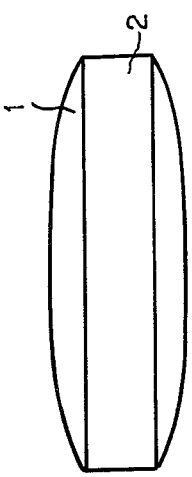
FIGS. 44, 46 and 48 are side views of capsules which have a distinctive shape.
Figure 52:
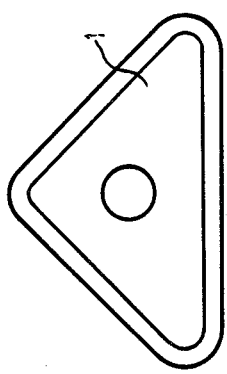
Figure 50:
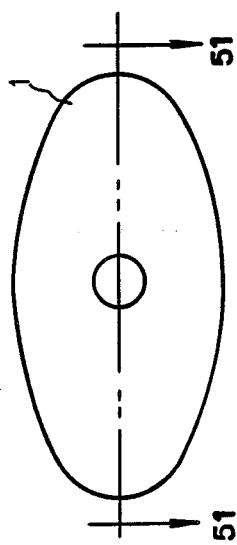
FIG. 50 is a top plan view of another capsule.
Figure 53:
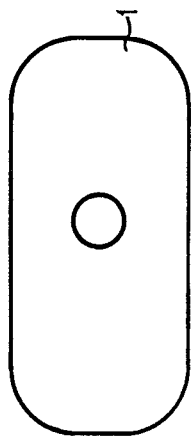
Figure 51:
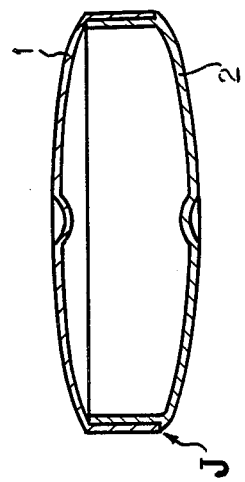
FIG. 51 is a cross-sectional side view of the capsule of FIG. 50.

FIG. 48 is a side view of an alternate embodiment showing a flat capsule. FIG. 49 is a top plan view of FIG. 48 showing the elongated oval-shaped capsule. FIG. 50 is a refinement of the embodiment of FIGS. 48 and 49 showing a modified oval shaped capsule. FIG. 51 is a sectional side view of FIG. 50 showing the side walls of cap 2 completely overlapping the side walls of body 1 when joined. Also shown is the smooth outer surface of side walls at the joining area J. The use of completely overlapping side walls and a smooth outer surface at the joining area make it difficult for potential tamperers to grip and separate the capsule parts. FIGS. 52 and 53 are views of another refinement of the embodiments of FIGS. 48, 49, 50 and 51 showing a rectangular oval-shaped capsule.

Figure 54:
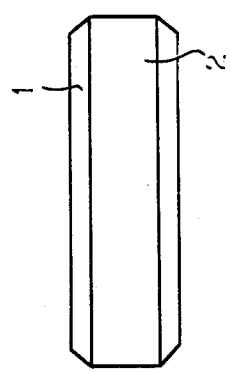
FIGS. 52, 54 and 56 are top plan views of additional capsules, each of which have a distinctive shape.
Figure 55:
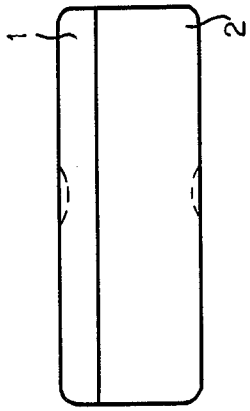
FIGS. 53, 55 and 57 are side views of the capsules of FIGS. 52, 54 and 56, respectively.
Figure 56:
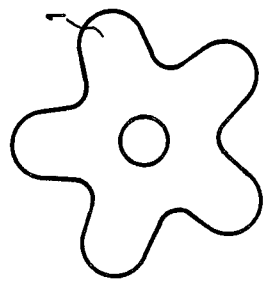
Figure 57:
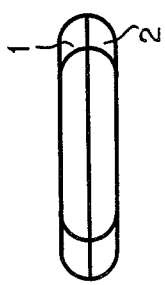

FIGS. 54 and 55 are views of a triangular-shaped capsule, while FIGS. 56 and 57 illustrate a star-shaped capsule. FIG. 57 is a side view of FIG. 56.

2. Capsules with a shape which corresponds to a vendor's logo

The logo-shaped capsules of this group help to identify the vendor. The logo of imaginary companies have been utilized in FIGS. 58-61.

Figure 61:
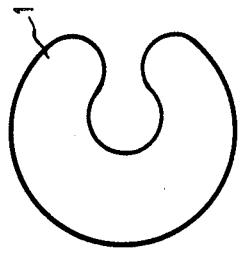
FIGS. 59 and 61 are side views of the capsules of FIGS. 58 and 60, respectively.
Figure 60:
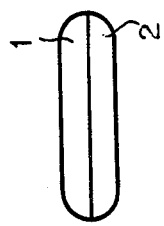
FIGS. 58 and 60 are top plan views of capsules manufactured in a shape corresponding to a vendor's logo.
Figure 59:
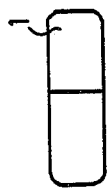
Figure 58:
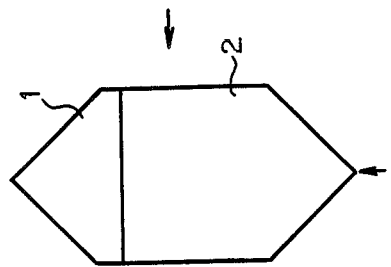

FIGS. 58 and 59 are views of a parallelolipodonal-shaped capsule logogram. FIGS. 60 and 61 are views showing a C-shaped capsule logo. With the use of the new die-molding processes to produce capsules, a great variety of shapes of capsules, including all the letters of the alphabet, in various forms, is now obtainable. This is in marked contrast to the severe limitations of prior art hard shell capsule shapes made with the prior art dip-molding method.

3. Capsules with a shape which indicates their purpose

Figure 62:
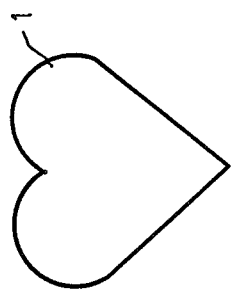
FIG. 62 is a top plan view of a capsule which is shaped to indicate its purpose.
Figure 63:
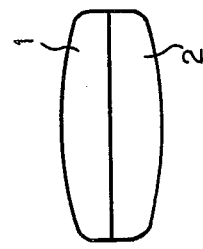
FIG. 63 is a side view of the capsule of FIG. 62.

The purpose-shaped capsules of this group help to indicate their field of application. As shown in FIGS. 62 and 63, the heart shape indicates the field of coronary applications.

4. Capsules with a shape indicating their dosage form

Figure 64:
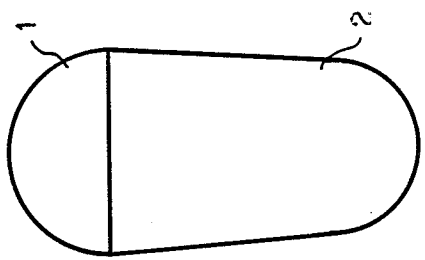
FIG. 64 is a side view of a capsule having a shape representing its dosage form.
Figure 65:
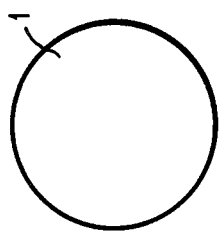
FIG. 65 is a top plan view of the capsule of FIG. 64.

The dosage-shaped capsules of this group indicate their use for other than oral medications. FIGS. 64 and 65 show a suppository-shaped capsule suitable for rectal medication. It will be understood by those skilled in the art that the embodiments above can enable the production of two-piece hard shell capsules with palpable shapes that can be recognized by visually impaired patients.

5. Capsules with a shape which provides a varying volume of contents

Figure 66:
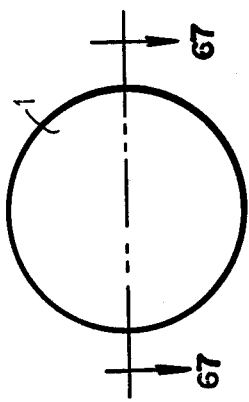
Figure 67:
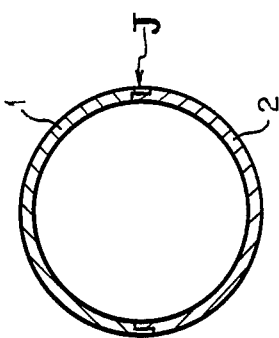

The embodiments of this group provide varying volumes of contents for the same size capsule. FIGS. 66 and 67 show a spherical shape providing the smallest possible package for the largest volume of contents.

These figures also showing separation-resistant locking means at the side walls of body part 1 and cap part 2 at the joining area J.

FIGS. 68 and 69 show a disc-shaped configuration which provides one of the largest possible packages for the smallest volume of contents. The great variety of capsule shapes produced by the injection-molding process provides great flexibility in the manufacture of hard shell capsules with varying package to volume ratios.

6. Capsules with a shape which enables a precise positioning on a joining machine There are various capsules which need an exact positioning of the cap and body parts before joining, e.g. a threaded or bayonet-type lock engagement. This precise positioning can be achieved by means of a locator on the outer surface of the capsule. FIGS. 70 and 71 are views showing 4 possible locating positions with respect to the rotary angle around the capsule axis. This is a significant advantage over a conventional dip-molded capsule which has a circular cross-sectional area. In FIG. 70, a capsule with four, possible positions is shown having a bayonet-type locking arrangement illustrated as, e.g., four protruding cams 53 on one part which mate with four corresponding ridges 54 on the other part. In FIG. 71 another bayonet-type closure system is shown as having an axial and a rotational movement of the body 2, with cap 1. (Axial and rotational movement is shown by dotted lines.)

It will be understood by those skilled in the art that there are capsule shapes of the present invention which meet the characteristics of more than one of the above mentioned groups.

In a further embodiment of the invention, the injection molded capsules are manufactured so as to provide bossed imprinting of letters or designs thereon.

Prior art capsules were imprinted using an ink composition. This process is very complicated and requires an additional step. Furthermore, it is difficult to imprint the closed ends of the capsule. With the bossed imprinting of the present invention, it is possible to obtain an imprinted capsule without the use of chemical inks. Thus, the imprinted capsule may be fully natural.

The capsule of the present invention may also be achieved by injection-molding the capsule parts with a mold which is provided with the desired imprinting (debossed or embossed) of letters or designs therein. The manufacturing and imprinting of the capsules may therefore be achieved in a single step. Furthermore, during debossing by injection molding, the capsule material is not adversely affected as in the prior art when the imprinting is made by a hot stamp. When a hot stamp is used there is also the disadvantage that a second processing step is necessary. Also, when using a hot stamp, embossing is not possible.

Figure 72:
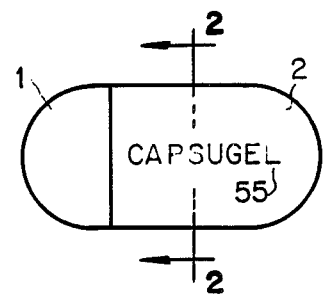
FIG. 72 is a side elevated view of a capsule embodiment having the name of the vendor embossed thereon.
Figure 73:
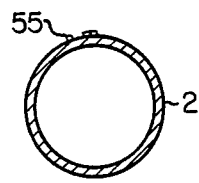
FIG. 73 is a sectional view of FIG. 72 taken along line 73—73.

FIGS. 72 and 73 are views of an embodiment of the present invention showing a joined capsule having cap 1 and body 2. Imprinted on the outside surface of the side wall of the cap is the embossing 55 of the letters in the name of the vendor CAPSUGEL. Such imprinting is not possible with the prior art dip-molding process, but embossing can be achieved with the new injection-molding process.

The present invention may also include a method for sealing or bonding the joined capsule parts which provides additional securing. This connection further impedes separation and tampering. Such sealing or bonding also makes the capsule liquid, moisture, vapor and gas-tight.

For sealing gelatin capsules, it is appropriate to wet the joining surfaces of the cap and body parts, either with water alone or a mixture of water with a water miscible organic solvent, such as an alcohol with 1-4 carbon atoms, e.g., ethanol. Optionally the capsule may also be initially heated to about 40°-75° C. Due to the high precision and the special locking means achieved by this die-pressure molding, heating is not absolutely necessary although it considerably improves the quality of the seal.

It is convenient to group several of the embodiments of the present invention into the following three categories:

1. Divisible Capsules

Figure 74:
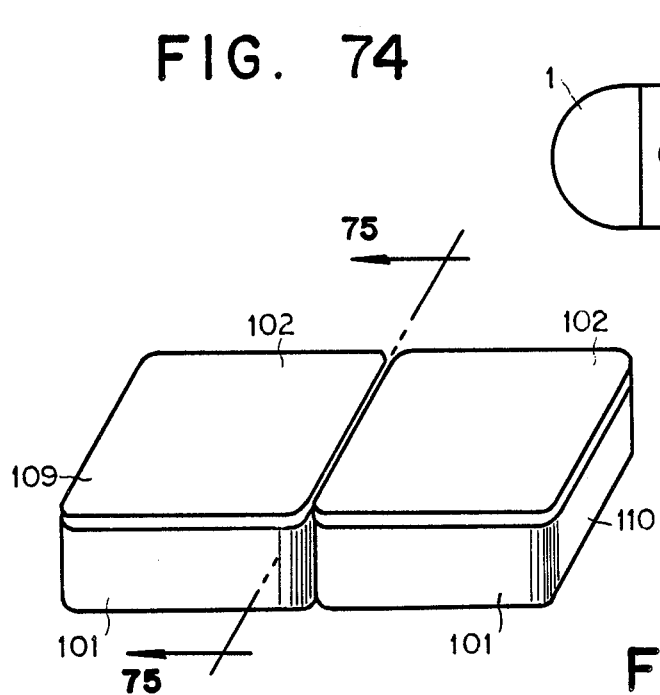
FIG. 74 is a perspective view of a divisible capsule consisting of two subunits.
Figure 75:
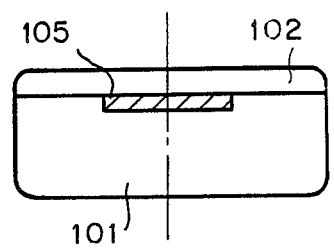
FIG. 75 is a cross-sectional view of FIG. 74 taken along line 75—75.
Figure 76:
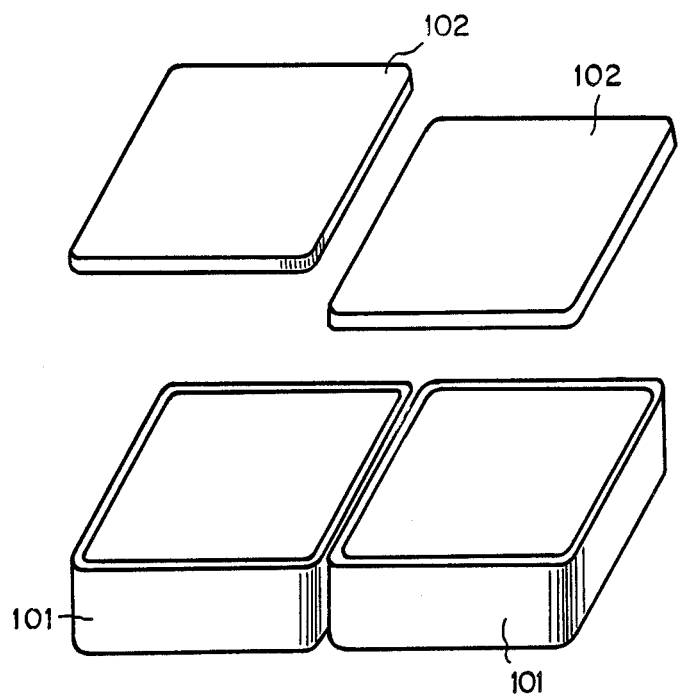
FIG. 76 is an exploded view of the capsule of FIG. 74.
Figure 77:
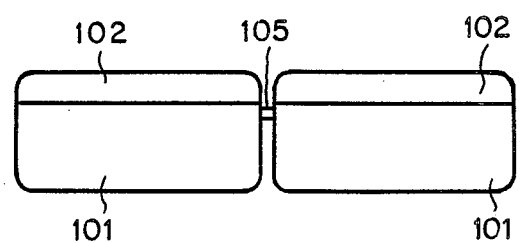
FIG. 77 is a side view of the capsule of FIG. 76.
Figure 80:
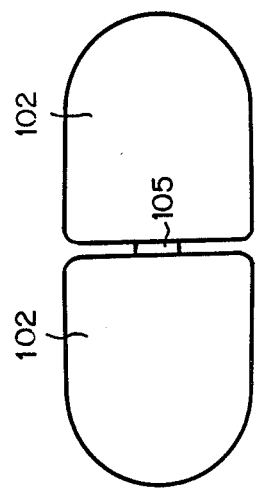
Figure 81:
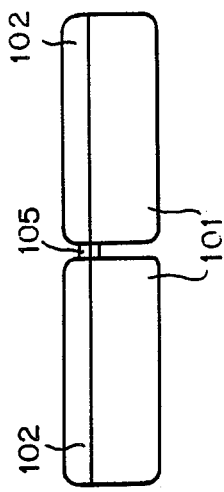

The divisible capsule form can be swallowed as a whole, or it can be separated into pieces which can be swallowed individually. Embodiments of this group are shown in FIGS. 74, 75, 76, and 77. FIG. 74 is a perspective view of a divisible capsule consisting of two subunits 109, 110 comprising two bodies 101 and two caps 102. As shown in FIG. 75, the two bodies 101 are connected by a weak joining lamella 105. The two caps 102 are not connected. In FIG. 76, the dosage form is shown after filling but before the caps 102 are put onto the bodies 101. FIG. 77 is a side view of FIG. 76 after the caps 102 have been put onto the bodies 101. The embodiment shown in FIGS. 74 to 77 may, as noted above, be swallowed as a whole capsule in the initial state but this dosage form can also be swallowed individually after it has been separated into two subunits along the lamella 105.

The two subunits of the divisible capsule shown in FIGS. 74 to 77 may be filled with different or with the same medicaments. In cases where both subunits are filled with the same medicament, the amount of the dosage can be divided by breaking the form into two pieces. In cases where the capsule is filled with two different medicaments—one in each subunit—the desired medicament can be swallowed by breaking the capsule at the lamella. In order to identify the content of each subunit, the colors of the subunit may be different or the subunits may be differently imprinted.

The capsule parts 101, 102 and the connecting lamella 105 can be manufactured simultaneously by die-molding and preferably by injection-molding. The lamella 105 consists of the same material as the capsule parts 101 and 102.

Figure 78:
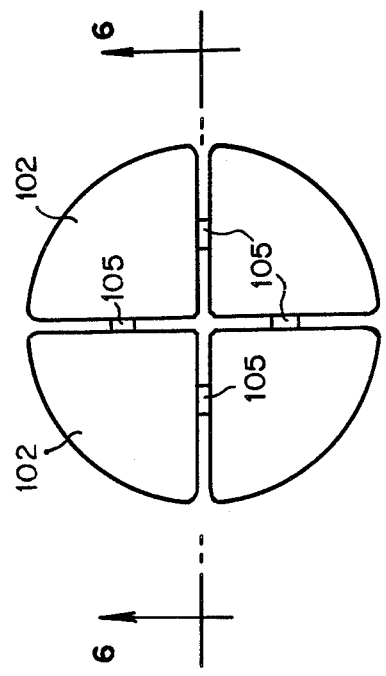
FIG. 78 is a top plan view of a divisible capsule consisting of four subunits.
Figure 79:
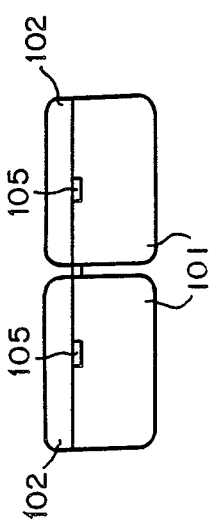
FIG. 79 is a side view of the capsule of FIG. 78.

FIGS. 78 and 79 show yet another embodiment of a capsule having four subunits. FIGS. 78 and 79 show four caps 102 and four bodies 101 connected by weak lamellas 105, so as to provide breaking possibilities. This embodiment may be swallowed as a whole or as three, two or only one subunit. Additionally, the different subunits of the capsule may be filled with different or the same medicaments.

Alternate embodiments are shown in FIGS. 80 to 85, using the same reference numerals as those used in FIGS. 74 to 79. In these embodiments, the bodies 101 and caps 102 are connected by weak lamellas 105. As shown in FIGS. 84 and 85, the caps 102 may overlap the bodies 101. Also, the cap parts 102 may have a recess 106 at the place where the connecting lamella 105 is located so that the lamella 105 is not seen from the top of the capsule and is hardly visible after the capsule has been broken into its subunits.

Figure 86:
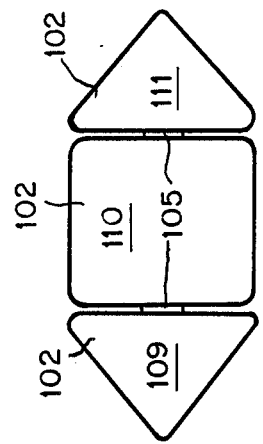
FIGS. 86–89 depict further alternate embodiments of a divisible capsule wherein only the body parts are joined by connecting lamella.
Figure 87:
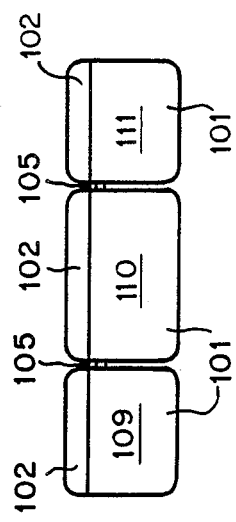
Figure 88:
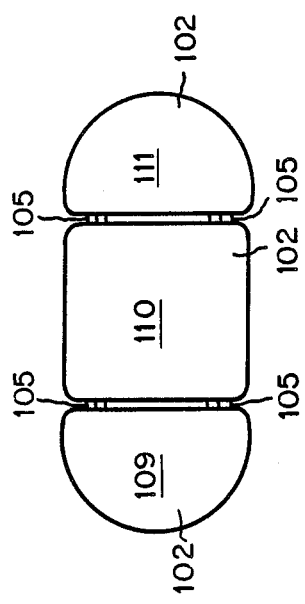
Figure 89:
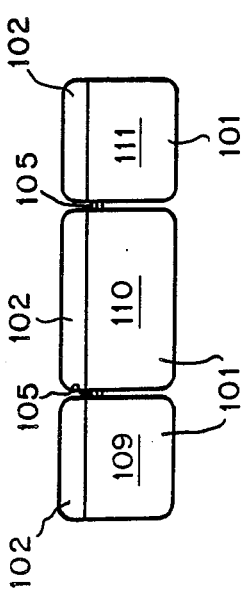

Another embodiment is shown in FIGS. 86 and 87, wherein the capsule has three subunits 109, 110, 111 having an inner and two outer parts, each of which again consists of a body 101 and a cap 102. In FIGS. 86 and 87 the outer parts are formed as triangles. Alternately, the outer parts in FIGS. 88 and 89 have the shape of semicircles. In the embodiments of FIGS. 86 to 89 only the bodies 101 are connected by the lamellas 105 whereas the caps 102 are separate pieces.

2. Compartmented Capsule

The compartmented capsule has two or more compartments for medicaments. It cannot be broken into subunits but it can be filled with two or more different medicaments to be swallowed simultaneously. It is an advantage of the die-molding technique that the number of the compartments is not limited to two but can be varied as required by the application.

Figure 90:
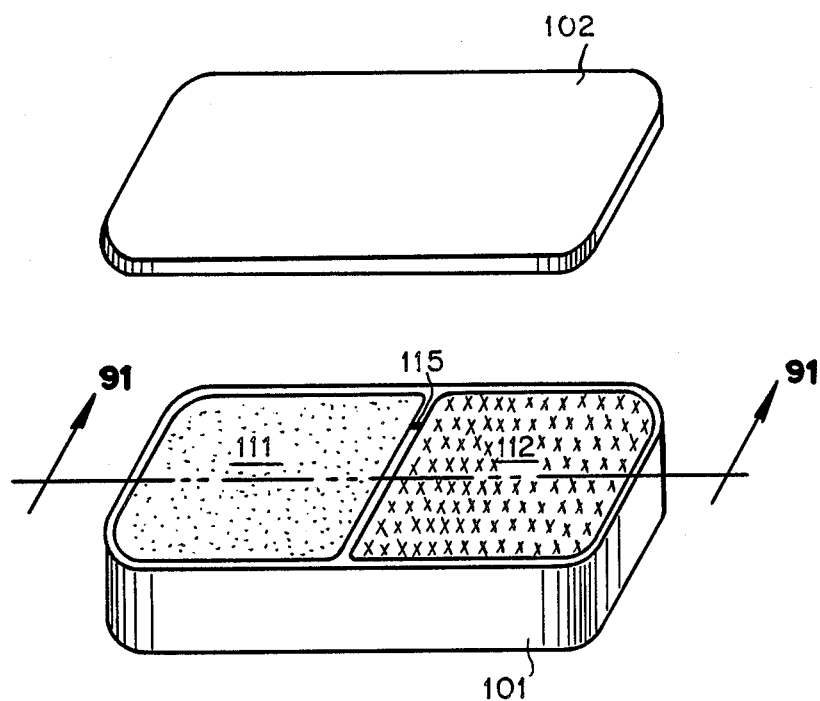
FIG. 90 is an exploded perspective view of a compartmented capsule.
Figure 91:
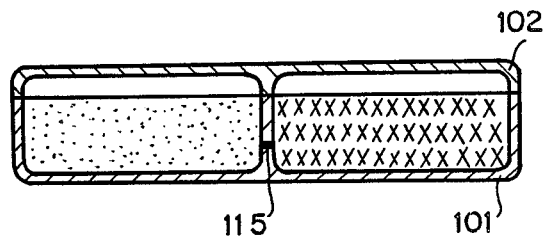
FIG. 91 is a cross-sectional view of the capsule of FIG. 90 taken along line 91—91.

An embodiment of this group is shown in FIGS. 90 and 91. FIG. 90 is an exploded perspective view of a compartmented capsule having a cap 102 and a body 101 with two compartments 111, 112 therein, separated by a partition 115. Each of the compartments 111, 112 contain different medicaments. FIG. 91 shows the complete separation of the different medicaments in compartments 111 and 112 when the capsule is closed.

Figure 92:
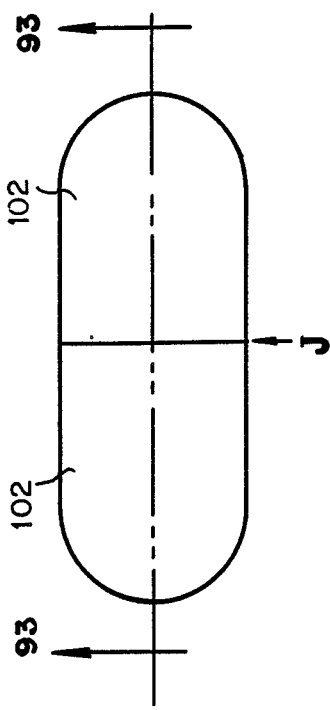
FIG. 92 is a top plan view of another compartmented capsule.
Figure 93:
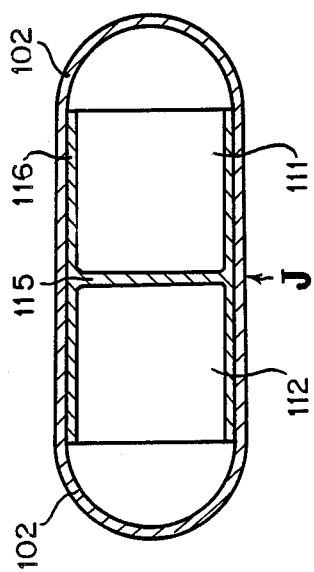
FIG. 93 is a sectional view of the capsule of FIG. 92 taken along line 93—93.

FIGS. 92 and 93 are views of a compartmented capsule showing two caps 102 axially abutting together at their open ends. FIG. 93 also shows the two caps 102 abutting together at their open ends, but included within the caps 102 is a cylindrical body 116 which is divided by an integrally molded disc or partition 115 into two compartments 111, 112 for containing different medicaments. After filling the different medicaments into the compartments 111, 112, each of the two caps 102 are telescopically joined over the body 101 from each open end so as to confine the different medicaments therein. For different therapeutic requirements, one of the caps 111 could be made of a material soluble in the acid secretions of the stomach. The other cap 101 and the body 102 could be made of enteric materials. In this way, one of the medicaments in a compartment could be distintegrated within the stomach of the patient while a different medicament in the other compartment could be disintegrated in the intestinal tract of the patient. By varying the materials and/or the thicknesses of the caps 101 and the body 102, the disintegration rates of each compartment 111, 112 may be controlled.

It is another feature of this invention that cap 101 and body 102 can be joined so as to provide a smooth surface at the joining area, J, as shown in FIGS. 91, 92 and 93.

3. Capsule Package

A capsule package consists of two or more capsules which are connected in a manner so that each subunit can be broken off as needed for use. Capsule packages are not intended to be swallowed as a whole but rather to provide a convenient storage form, e.g., when each subunit has to be taken periodically. Therefore, the number of connected subunits is not limited because of an easy-to-swallow requirement. These capsule packages may also be used to package the divisible capsule of group 1 and the compartmented capsule of group 2.

Figure 94:
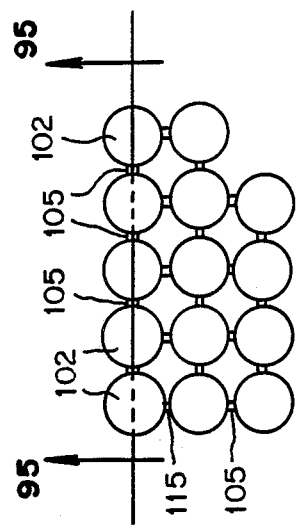
FIG. 94 is a top plan view of a capsule package showing the capsules aligned along their axes.
Figure 95:
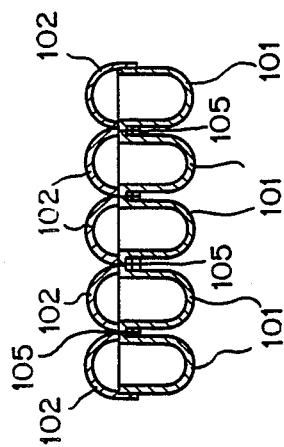
FIG. 95 is a sectional view of the capsule package of FIG. 94 taken along line 95—95.

An embodiment of this group is shown in FIGS. 94 and 95, which show the capsule bodies 101 connected by the lamellas 105 made of the same material as the capsule bodies 101 and which are manufactured simultaneously. The caps 102 of the dosage package are not connected to each other. Both the bodies 101 and the caps 102 may be provided with locking means so as to yield a separation-resistant arrangement.

Another embodiment of the capsule package is shown in FIGS. 96 and 97 which show the capsule bodies 101 connected by the lamella 105, which may be of the same material as the capsule bodies 101. These lamella 105 are manufactured simultaneously with the bodies 101. Also, both the bodies 101 and the caps 102 may be provided with any of the previously described locking means.

Another embodiment of the capsule package for the combination of two different medicaments is shown in FIGS. 98 and 99, which show a plurality of capsule bodies 101 and caps 102 which are formed simultaneously by die-molding. The bodies 101 are connected while the caps 102 are not. The capsules are shown as arranged in two rows so that the two medicaments can be filled in adjoining bodies.

Blister packages are a known form of packaging for pharmaceutical dosages and other high-security products. It is another feature of the present invention that hard shell capsules can be formed from the blister package components of a blister sheet and a cover sheet which are sealed together by heat and pressure. Subsequently, the blisters are filled with medicaments. In this invention the blister package components are manufactured from water soluble and edible gelatin or hydrophilic polymers.

Figure 100:
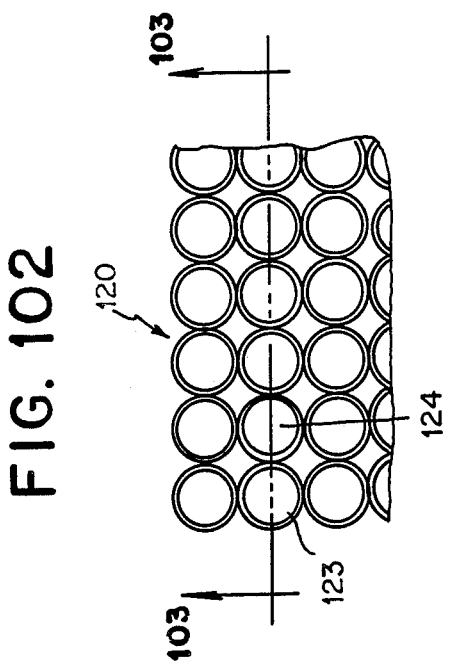
FIGS. 100 and 102 are top plan views of capsule blister packages.
Figure 101:
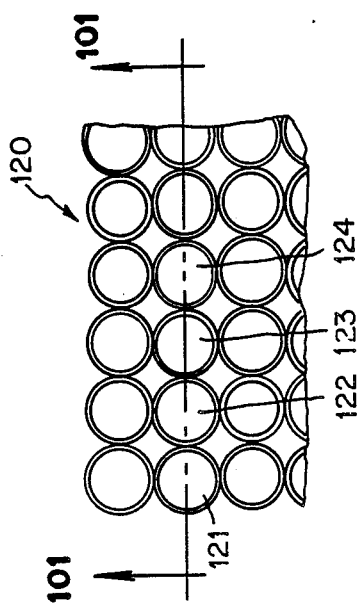
FIGS. 101 and 103 are cross-sectional views of the blister packages of FIGS. 100 and 102, taken along lines 101—101 and 103—103, respectively.

FIGS. 100 and 101 are views of an embodiment of a capsule blister package, showing the blister sheet 120 having separate blister compartments 121, 122, 123, 124 ... therein. A cover sheet 125 is sealed by pressure and heated to the blister sheet 120 so as to seal the blister compartments 121, 122, 123, 124 ... containing medicaments. At the juncture of the blister sheet 120 with the cover sheet 125 there may be perforations 126 so as to close the separations of the blister compartments 123, 124 . . . FIGS. 102, 103, 104 and 105 show alternative embodiments of capsule blister packages using the same reference numerals as FIGS. 99 and 100.

Figure 102:
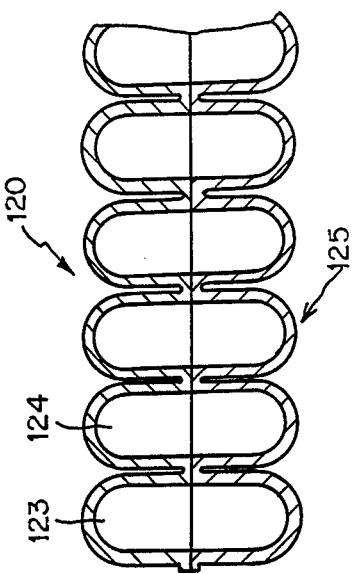
Figure 103:
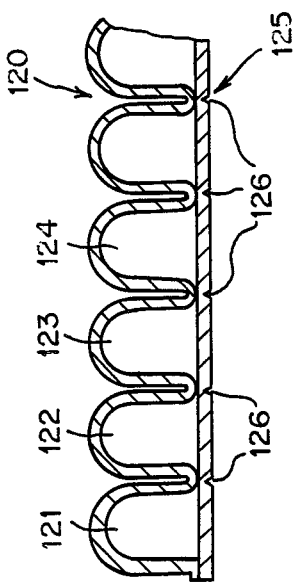

In FIGS. 102 and 103 the capsule blister package is shown having an elongated cross section of a conventional capsule form wherein the blister sheet 120 and the cover sheet 125 have symmetrical compartments 123, 124 therein.

Figure 104:
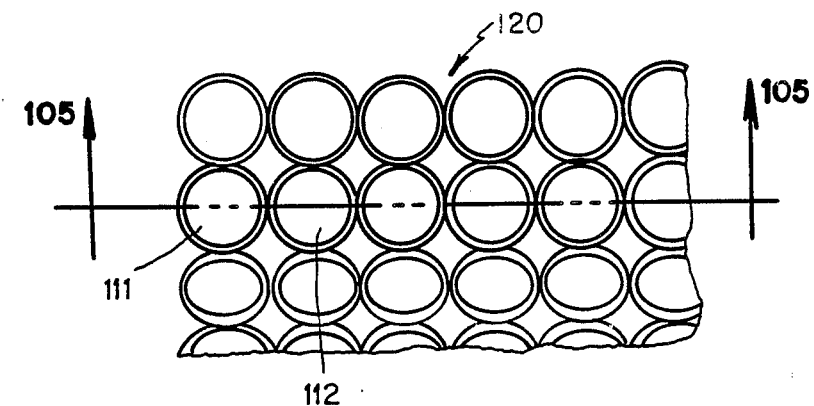
FIG. 104 is a top plan view of another blister package.
Figure 105:
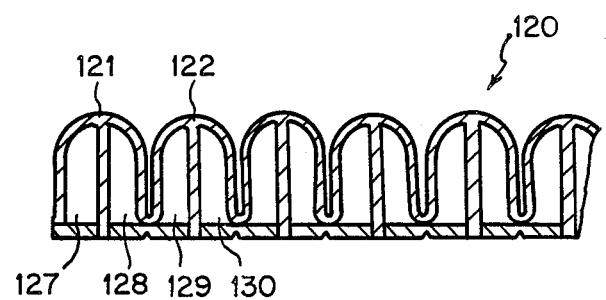
FIG. 105 is a sectional view of the embodiment of FIG. 104 taken along line 105—105.
Figure 108:
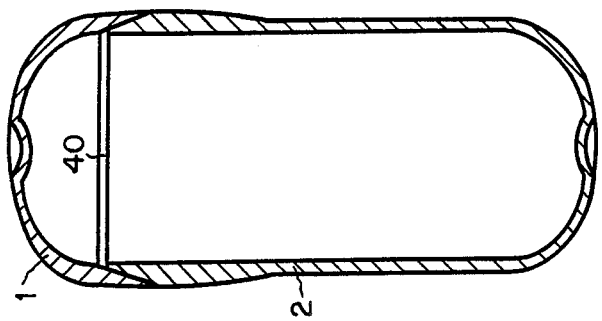
Figure 107:
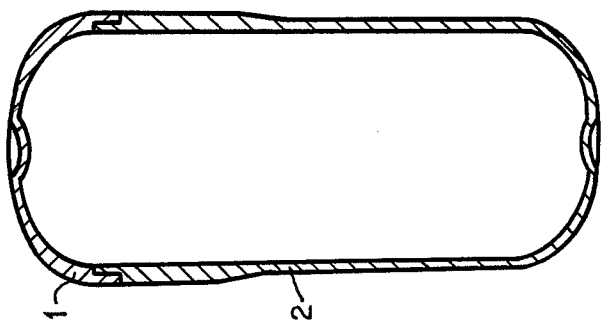
Figure 106:
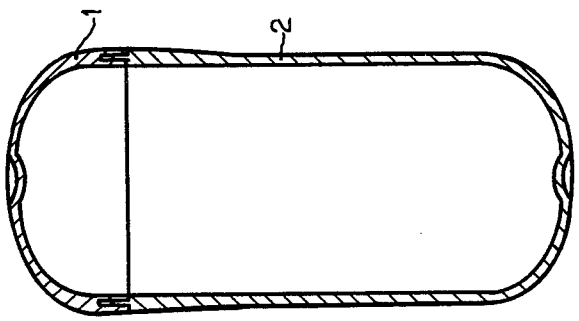

In FIGS. 104 and 105, the capsule blister package is shown with each compartment 121, 122 subdivided into subunits 127, 128, 129, 130, respectively, for containing different medicaments therein.

FIGS. 106-109 are sectional views of an embodiment of a pharmaceutical capsule similar to that depicted in FIG. 1C. While all four embodiments illustrated therein possess alternate arrangements for locking the cap 1 and body 2 of each capsule together in a tamper resistant configuration, FIG. 108 additionally illustrates the provision of a cover plate 40 placed across the upper portion of the body 2 to prevent the interaction of the medicaments stored therein with air entrapped beneath the inner surface of cap 1, and optionally, to provide an additional compartment.

FIG. 110 illustrates a capsule embodiment similar in many respects to the capsule depicted in FIG. 1D. This embodiment is provided with a window for receiving the locking tabs of the other capsule part. It is possible to provide a plurality of such windows on one capsule part with the same number of locking tabs on the other part.

FIGS. 111 and 112 illustrate a ridge and groove locking arrangement utilized to maintain the cap portion and the body portion in locking engagement. This embodiment is also provided with a cover plate 40 for insertion above the medicament 30 located in the body 2 of the capsule.

FIG. 113 is a sectional view of an embodiment similar in many respects to the capsule depicted in FIG. 1A. This embodiment utilizes an alternate embodiment of the ridge and groove locking arrangement wherein a cover plate 40 is placed perpendicular to the opening of the body of the capsule to prevent the interaction of entrapped air with the medicament 30 located below.

FIGS. 114 and 115 depict an alternate embodiment of the capsule of FIG. 110 having two windows instead of one, and wherein the body 2 of the capsule has a smaller diameter than the cap 1. This dual ridge and groove locking assembly includes cover plate 40.

FIGS. 116A and B are sectional views of a capsule embodiment similar to that depicted in FIG. 1B. FIG. 116A has one locking window in the cap portion, the purpose of said window having been described earlier. Further, in FIG. 116A, there is an edge portion present on the outer surface of the capsule where the cap and body portions are joined. The embodiment depicted in FIG. 116B shows a smooth outer surface in the same area. In addition, both embodiments are provided with a cover plate 40 for protecting the medicaments 30 enclosed therein from the effects of entrapped air.

In FIGS. 117A, B and C, there are shown embodiments of capsules of the present invention similar to those depicted in FIGS. 28-30, but having no locking windows. These capsules have a cap 301 and a body 302 which may be filled with a pharmaceutical product to be swallowed by a patient. FIGS. 117B and C show the preferred embodiments of the invention wherein the ratio of D to L is equal to or greater than one, while FIG. 117A shows a typical capsule having a ratio of less than one.

It is understood by those skilled in the capsule arts that there is an advantage with a variable D to L ratio in that the volumetric contents of the same diameter capsule can be changed to meet particular pharmaceutical dosage requirements. In addition, the most preferred capsule configuration has a D to L ratio of 1 or more so as to make the capsule more nearly in the squat configuration of a tablet. Also, the squat shape is psychologically easier to swallow by children, adults and geriatric patients who differ markedly in their ability to swallow capsules.

The present invention may also include a process for sealing or bonding of the cap andd body parts where they are joined. Sealing or bonding provides additional security by further impeding separation of the capsule and subsequent tampering with its contents. This also makes the capsule, liquid, moisture vapor and gas-tight.

The capsules produced in conformity with the present invention may be used for pharmaceutical purposes, and to provide an exact quantitative dosage of dyestuffs, chemicals, spices, fertilizing combinations for plants, fertilizers with protective substances, seeds, cosmetics, agricultural products, etc. The capsules of the present invention may also be used to deliver an exact quantitative dosage of vitamins, foods, etc. All of the embodiments of the present invention can be produced on injection-molding machines wherein the capsule material is melted in a plasticizing unit and then injected into a mold. When the mold is opened, the capsule parts are ejected. As dosage form materials one may use: gelatin, or other polymer materials including mixtures and foams of such materials, which are water-soluble, edible and suitable for casting or molding. Film casting, injection molding, compression molding, blow molding, deep drawing methods and other die-molding techniques may also be used for the production of the capsules of the present invention.

In addition to capsules, the injection molding of gelatin can be utilized to provide many useful products requiring high form stability and a minimum of dimensional deviations. These products include candies, packaging containers for food-stuffs, pharmaceuticals, chemicals, dyestuffs, spices, fertilizing combinations, seeds, cosmetics, agricultural products and matrices of various shapes and sizes of gelatin compositions whose contents include food stuffs, pharmaceuticals, chemicals, dyestuffs, spices, fertilizing combinations, seeds, cosmetics and agricultural products, which are microdispersed within the matrix and released from it through disintegration and/or dissolution and/or bioerrosion and/or diffusion depending on the solubility characteristics of the gelatin composition used. Some of these products may also result in a controlled release delivery system for the enclosed substance.

Furthermore, medical and surgical products can be prepared by injection molding gelatin compositions. The biodegradable nature of gelatin makes it environmentally desirable over certain materials presently being used. In addition, the non-toxic nature of the materials further enhances their desirability as a material to be used in the injection molding industry.

Figure 118:
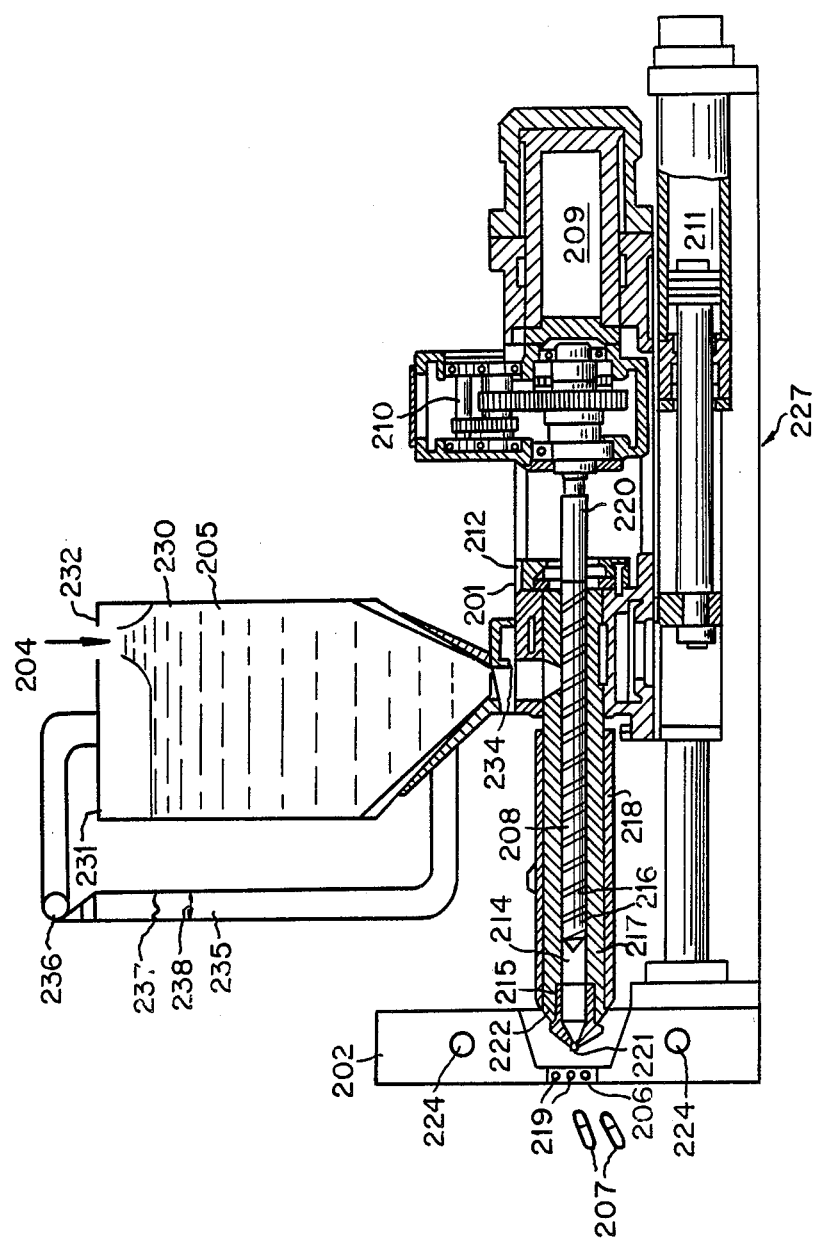
FIG. 118 is a schematic of a reciprocating screw injection molding device for making capsule parts.
Figure 118:
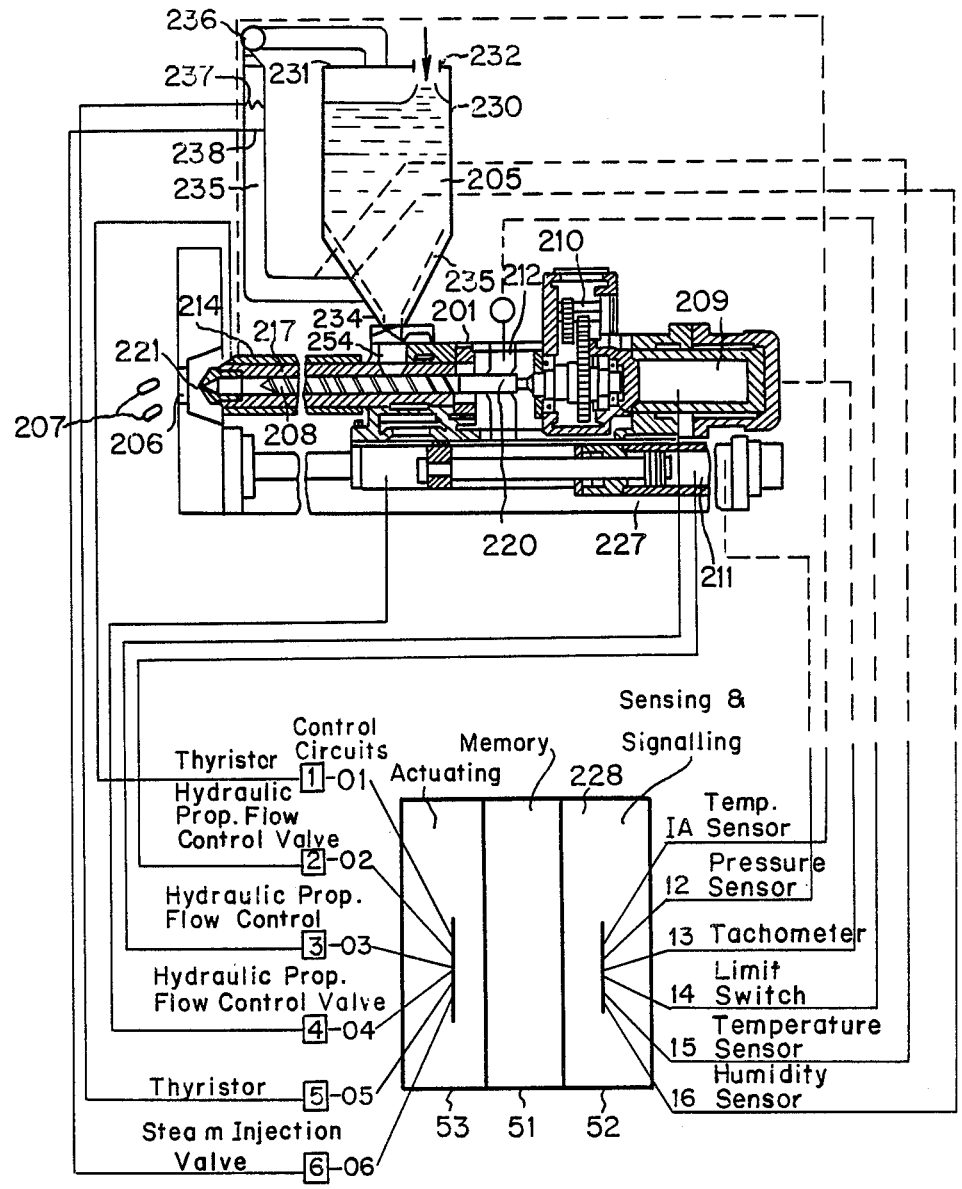

Referring now to FIG. 118, the injection molding device 227 for manufacturing capsules of the type described above consists of three units: a hopper unit 205, an injection unit 201 and a molding unit 202.

The function of the hopper unit 205 is receiving, storing, maintaining and feeding gelatin 204 at a constant temperature and at a constant water content. The hopper unit 205 comprises a vertical cylinder 230 having a closed top 231 with an inlet 232 therein to receive gelatin 204. At the bottom of the vertical cylinder 230 is a closed conical funnel 233 and a discharge outlet 234 to feed gelatin 204 into an inlet 234 of the injection unit 201. There is an air duct 235 communicating between the closed top 231 and the conical funnel 233 wherein air is circulated by a blower 236, the air temperature is maintained by a thyristor 237 and the relative humidity of the air is maintained by a steam injector 238.

The function of the injection unit 201 is melting, dissolving in water, and plasticizing in the extruder barrel 217 the gelatin 204 fed from the hopper unit 205 into the extruder inlet 254 and injecting the plasticized gelatin 214 into the molding unit 202.

The function of the molding unit 202 is automatically holding, opening and closing the mold 206 having capsule shaped cavities 219 therein, and ejecting the capsule parts 207 therefrom.

Within the injection unit 201 the screw 208 both rotates and undergoes axial reciprocal motion. When the screw 208 rotates, it performs the functions of melting, dissolving in water, and plasticizing the gelatin 204. When the screw 208 moves axially, it performs its injection function by transporting and ramming the plasticized gelatin 214 into the mold 206. The screw 208 is rotated by a variable-speed hydraulic motor 209 and drive 210, and its axial motion is reciprocated by a duplex hydraulic cylinder 211.

Compression of the plasticized gelatin 214 in front of the rotating screw 208 forces back the screw assembly 220 containing the screw 208, the drive 210 and the motor 209. When the screw assembly 220 reaches a pre-setback position a limit switch 212 is contacted. When a defined time has elapsed, during which the gelatin 204 becomes fully plasticized gelatin 214, the hydraulic cylinder 211 brings the screw assembly 220 forward and uses the screw 208 as a ram which causes the plasticized gelatin 214 to be injected through a valve body assembly 250 including a one-way valve 215, a needle valve 223, nozzle 222 and an outlet port 221 into the molding unit 202.

The one-way valve 215 prevents the plasticized gelatin 214 from going back over the helical flutes 216 of the screw 208. The extruder barrel 217 has steam heating coils 218 to heat the gelatin 204 while it is being compressed by the screw 208 into plasticized gelatin 214. It is desirable for the plasticized gelatin 214 to be heated at the lowest possible temperature and to be transported with the lowest possible speed of the screw 208.

The speed of the screw 208 and the heating of the plasticized gelatin 214 within the extruder barrel 217 by the steam heating coils 218 controls the quality and the output rate of the plasticized gelatin 214 injected into the molding unit 202. The molding unit 202 holds the mold 206 having capsule shaped cavities 219 into which the plasticized gelatin 214 is injected and maintained under pressure. Refrigerant cooling conduits 224 encircle the mold 206 so that when the plasticized gelatin 214 in the mold 206 has cooled and sufficiently solidified, the molding unit 202 opens, the mold 206 separates and the capsule parts 207 are ejected.

Figure 119:
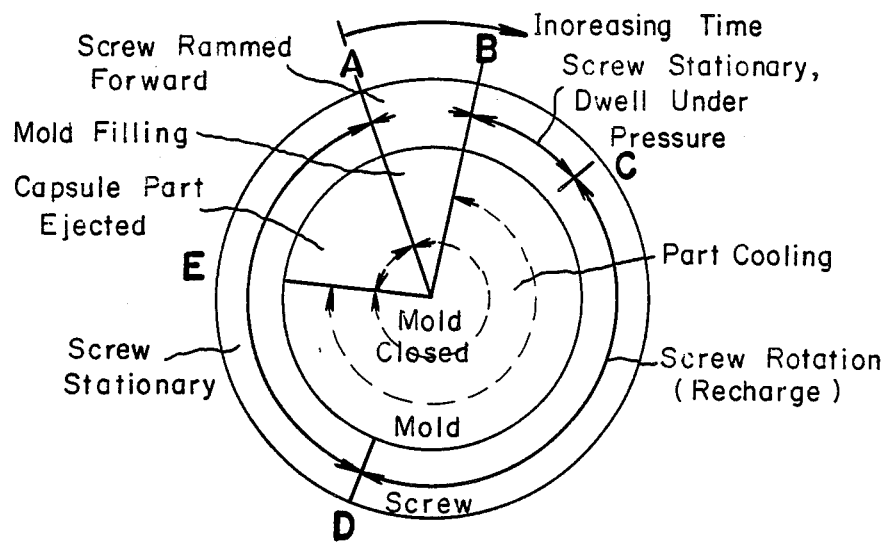
FIG. 119 is a schematic of an injection molding work cycle.

Referring now to FIG. 119, which depicts the injection molding work cycle for gelatin 204 (containing approximately 17% water by weight) plotted against time, the work cycle of gelatin 204 in the injection molding device 227 of the present invention is generally as follows:

a. gelatin 208 is fed into the hopper unit 205 where it is received, stored and maintained under conditions of temperature ranging from ambient to 100° C., pressure ranging from $1-5 \times 10^5$ Newtons per square meter ($N \times m^{-2}$) and water content ranging from 5 to 25% by weight of gelatin, b. the stored gelatin 204 is melted under controlled conditions of temperature ranging from 50° to 190° C., water content ranging from 5 to 25% by weight of gelatin and pressure ranging from 600 to $3000 \times 10^5$ $N \times m^{-2}$, c. the molten gelatin 204 is dissolved in water under controlled conditions of temperature ranging from 50° to 190° C., pressures ranging from 600 to $3000 \times 10^5$ $N \times m^{-2}$, and water content ranging from 5 to 25% by weight of gelatin.

d. the dissolved gelatin is plasticized under controlled conditions of temperature ranging from 50° to 190° C., pressure ranging 600 to $3000 \times 10^5$ $N \times m^{-2}$, and water content ranging from 5 to 25% by weight of gelatin.

e. The plasticized gelatin 214 is injected into the mold 206 under controlled conditions of temperature below 50° C., injection pressure ranging from 600 to $3000 \times 10^5$ $N \times m^{-2}$ and a clamping force of the mold 206 below approximately 600,000 Newtons, and f. the capsule-shaped parts 207 are ejected from the molded gelatin within the mold 206.

Beginning at point A of FIG. 119 the screw 208 moves forward and fills the mold 206 with plasticized gelatin 214 until Point B and maintains the injected plasticized gelatin 214 under high pressure, during what is called the hold time, i.e. from point B until Point C of FIG. 119. At Point A, the one-way valve 215 at the end of the screw 208 prevents the plasticized gelatin 214 from flowing back from the nozzle 222 onto the screw 208. During the hold time, additional plasticized gelatin 214 is injected, offsetting contraction due to cooling and solidification of the plasticized gelatin 214. Later, the outlet port 221, which is a narrow entrance to the molding unit 202 closes, thus isolating the molding unit 202 from the injection unit 201. The plasticized gelatin 214 within the mold 206 is still at high pressure.

As the plasticized gelatin 214 cools and solidifies, the pressure drops to a level that is high enough to ensure the absence of sinkmarks, but not so low that it becomes difficult to remove the capsule parts 207 from the capsule-shaped cavities 219 within the mold 206. After the outlet port 221 closes, at Point C. screw 208 rotation commences. The plasticized gelatin 214 is accommodated in the increased cylindrical space in front of the screw 208 created by its backward axial motion until Point D. The flow rate of the plasticized gelatin 214 is controlled by the speed of the screw 208 and the pressure is controlled by the back pressure (i.e., the hydraulic pressure exerted on the screw assembly 220) which, in turn, determines the pressure of the plasticized gelatin 214 at the nozzle 222 in front of the screw 208.

After plasticized gelatin 214 is generated for the next shot into the mold 206, the screw 208 rotation ceases at Point D. The gelatin 204 on the stationary screw 208 continues to melt from Points D to E by heat conducted from the steam heating coils 218 on the extruder barrel 217. This period is called the soak time. Meanwhile, the solidified capsule parts 207 are ejected from the mold 206. Thereafter, the mold 206 closes to accept the next shot of plasticized gelatin 214. All of these operations are automated and controlled by a microprocessor as hereinafter described.

Again referring to FIGS. 118A and 119, the injection molding work cycle of FIG. 119 is accomplished on the injection molding device 227 of FIG. 118 by hydraulic and electrical components and the corresponding circuits controlled by the microprocessor 228 of FIG. 118A.

Through the use of solid-state circuitry and of speed, temperature and pressure limit switches for the electrical and hydraulic systems, the microprocessor 228 of the present invention utilizes command signals in its memory 251 for the parameters of time, temperature and pressure. These ranges are shown in Table 1 below for the injection molding work cycle of FIG. 119 to be accomplished by the injection molding device 227 of FIG. 118 in producing gelatin capsule parts 207.

TABLE 1

Ranges of Time, Temperature and Pressure at the Top of the Screw for the Injection Molding Work Cycle of FIG. 119:

| | POINTS | | | | |
|---|---|---|---|---|---|
| | A | B | C | D | E |
| Time (seconds) | $10^{-2}-1$ | $10^{-2}-1$ | $10^{-2}-1$ | $10^{-2}-1$ | $10^{-2}-1$ |
| Temperature (°C.) | Ambient-100 | 50-190 | 50-190 | 50-190 | 50-190 |
| Pressure ($10^6$ N/m$^2$) | A-B 60-300 | B-C 60-300 | C-D 1-300 | D-E 60-300 | |

(Newtons per square meter)

Referring now to FIG. 118A illustrating the combined injection molding device 227 and microprocessor 228 for practicing the method of the present invention:

The combined injection molding device 227 and microprocessor 228 comprises six control circuits of which five are closed-loop, fully analog, and one is on-off. Starting at molding cycle Point A in FIG. 119, the injection molding work cycle operates as follows:

When sufficient plasticized gelatin 214 has accumulated in front of the screw 208 (microprocessor time controlled) and also when the screw assembly 220 carrying the screw 208, drive 210 and hydraulic motor 209 has been pushed far enough backwards against a constant back-pressure as controlled by control circuit 203, limit switch 212 will be actuated by position sensing circuit 214. Upon the occurrence of these two conditions, control circuit 204 is actuated, causing the hydraulic fluid to flow into the forward portion of the hydraulic cylinder 211. This rams the screw assembly 220 forward, thus injecting the plasticized gelatin 214 into the mold 206 as molding cycle Point B of FIG. 119 is reached, and, as controlled by the microprocessor 228, the screw 208 remains stationary in this forward position under high pressure for a certain period of time until Point C.

From molding cycle Point B of FIG. 119 onwards, the plasticized gelatin 214 cools down in the mold 206 and the port 221 closes at molding cycle Point C of FIG. 119.

At molding cycle Point C of FIG. 119, the screw 208 starts to rotate again and the hydraulic pressure is reduced from that at the forward portion of the hydraulic cylinder 211 to a pressure slightly less than the pressure set for the backward portion of the hydraulic cylinder 211.

The screw 208 is kept under constant pressure towards the mold 206 by the pressure in the back position of the hydraulic cylinder 211. This is achieved by means of the control circuit 202 where a proportional hydraulic valve is controlled by a pressure sensor circuit $I_2$.

As the screw 208 rotates, a recharge of gelatin 204 is made from the hopper 205. During a certain time period and at a defined rotating speed for the screw 208, controlled by control circuit 203, a precise amount of gelatin 204 is fed into the extruder barrel 217. Control circuit 203 is actuated by speed sensor circuit $I_3$ measuring the rotating speed of the screw 208 and sensing back to a hydraulic proportional flow control valve $O_3$ controlled by control circuit 203, thus assuring a constant rotating speed of the hydraulic motor 210, irrespective of the changing torque resulting from introduction of the gelatin 204 recharge.

When the load time is completed, the screw 208 rotation is stopped and molding cycle Point D of FIG. 119 is reached. The soak time molding cycle, Points D to A of FIG. 119, allows for the gelatin 214 to plasticize completely under controlled temperature conditions as controlled by control circuit 1.

A temperature sensor circuit $I_1$ senses a thyristor heat regulator $O_1$ heating the extruder 217 as directed by control circuit 1.

During the time interval from molding cycle Points B to E on FIG. 119, the mold 206 has cooled down sufficiently so that the finished capsule parts 207 can be ejected from the mold 206.

After ejection of the capsule parts 207, the work cycle returns to point A of FIG. 119, where a certain volume of plasticized gelatin 214 has accumulated in front of the screw 208 (sensing circuit $I_4$ is actuated and time has elapsed), so that the work cycle of FIG. 119 can be repeated.

It is important to note the temperature and humidity control loops 205 and 206 for the maintenance of a precise water content in the gelatin in the hopper 205, which is essential for proper operation at the desired speeds.

The microprocessor 228 includes a memory section 251 to store the desired operating parameters; a sensing and signaling section 252 to receive the sensing signals of actual operating conditions, to detect the deviation between the desired and actual operating conditions, and to send signals for adjustment through the actuating section 253 to the thyristors and valves.

Figure 120:
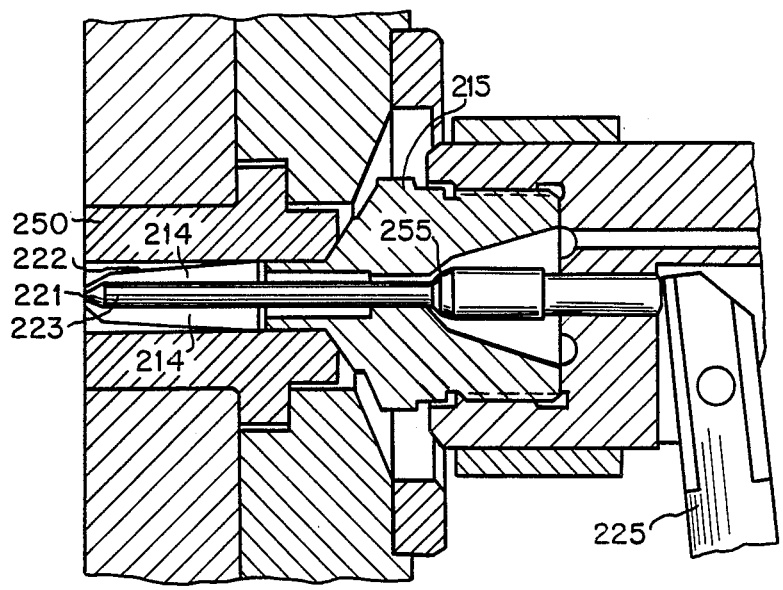
FIG. 120 is an expanded cross-sectional view of the exit end of the injection molding device.

Referring now to FIG. 120 there is shown the valve assembly 250 including the outlet port 221, the nozzle 222, the needle valve 223, and the one-way valve 215. These elements operate as follows:

At Point A in FIG. 119 the needle valve 223 is retracted from the outlet port 221 and the one-way valve 215 is retracted from the valve body 250 so as to form an inlet opening 255 for plasticized gelatin 214 into the nozzle 222 which defines a charging chamber for plasticized gelatin 214. The plasticized gelatin 214 is injected through nozzle 222 and into the mold 206 during the mold-filling time between Points A and B in FIG. 119. At Point C in FIG. 119 the needle valve 223 is pushed forward so as to close the outlet port 221 during which time between point C and E in FIG. 119, the mold 226 is closed and the capsule part 207 in the mold 206 is cooling. The needle valve 223 remains closed between Points E and A in FIG. 119 during which time the capsule part 207 is ejected from the mold 206. The total time period between Points B and A in FIG. 119 must be less than 5 seconds so that the plasticized gelatin 214 does not solidify in the nozzle 222. This is an important aspect of the present invention because:

a. faster production times are therefore made possible in order to achieve greater output;

b. there is no loss of plasticized gelatin 214 in the production cycle due to solidification in the nozzle 222 and the mold 206; and c. there is a minimum risk of degradation of the plasticized gelatin 214 because it remains in the production cycle for short time and is only utilized once in each production cycle because the plasticized gelatin 214 is solidified in the capsule-shaped cavities 219 and not in the nozzle 222.

The one-way valve 215 and the needle valve 223 are actuated by a spring-tensioned lever 225 which normally closes both the outlet port 221 and the nozzle 222 until the lever 225 is cam-actuated pursuant to signals from the microprocessor 228.

The thermomechanical properties of gelatin, i.e. storage and loss shear modules at different temperatures, are strongly dependent on its water content. The capsule molding process of the present invention can be used for gelatin with a water content preferably within a range of 5 to 25%. The lower limit is defined by the maximum processing temperature of 190° C., which in turn cannot be exceeded in order to avoid degradation. The upper limit is determined by the stickiness of the finished capsules. The abbreviations in Table 2 below will be used hereinafter in this application:

TABLE 2

| Abbreviations for Physical Parameters | | |
|---|---|---|
| ABBREVIATION | UNIT | DESCRIPTION |
| $T_a, P_a$ | °C., N/m² | Ambient temperature and pressure. |
| $H(T,P)$ | KJoule/Kg² | Enthalpy of hydrophilic polymer-water system at a given pressure and temperature. |
| $\beta(T,P)$ | m²/N | Compressibility of the hydrophilic polymer at a given temperature and pressure. Its numerical value is the relative volume change due to change of pressure by a unit amount. |
| $\alpha(T,P)$ | (°C.)⁻¹ | Volumetric thermal expansion coefficient of the hydrophilic polymer at a given temperature and pressure. Its numerical value is the relative volume change due to change of temperature by a unit amount. |
| $V(g,T,P)$ | Kg/sec¹ | Is the flow rate of the hydrophilic polymer at a given temperature and shear deformation rate [sec.⁻¹] and pressure. Its numerical value is the volume of a melt leaving the exit cross-sectional area of an injection molding device in unit time due to the applied shear deformation rate. |
| $T_{G1}; T_{G2}(X)$ | °C. | The temperature range of the glass transition of the hydrophilic polymer. |
| $T_{M1}; T_{M2}(X)$ | °C. | The temperature range for melting the partially crystalline hydrophilic polymer. |
| $T_E(t)$ | °C. | The temperature of the hydrophilic polymer in the nozzle area of the injection unit. |
| $T_M(t)$ | °C. | The temperature of the hydrophilic polymer in the mold. |
| $P_M$ | N/m² | The pressure of the hydrophilic polymer in the mold. |
| $P_E$ | N/m² | The pressure of the hydrophilic polymer in the nozzle area of the mold, expressed as the weight fraction of the water - hydrophilic polymer system. |
| X | | The water content of the hydrophilic polymer. |

For the control and regulation of the injection molding process (IMP) we need to know the (1) heat consumption of the melting process:

$$H(T_E, P_E) - H(T_a, P_a)$$

(2) the heating rates of the hydrophilic polymers in the injection molding device. To calculate this we need the heat conduction number of the hydrophilic polymer and the heat transfer number of the hydrophilic polymer and the specific material of construction of the barrel which is in contact with the hydrophilic polymer. The heating rate and the heat consumption of the hydrophilic polymer give the minimum time interval necessary to make the hydrophilic polymer ready to inject and the necessary heating power of the injection molding device.

(3) the $T_E$ depends on X of the hydrophilic polymers. If the water content of the hydrophilic polymer in the mold is too low, the resulting $T_E$ will be too high and cause degradation. A minimum water content of 5% by weight is required to keep $T_E$ below 190° C.

(4) the flow rate $V(g,T,P)$ is also strongly dependent on the water content of the hydrophilic polymer. To speed up the IMP, a high flow rate $V(g,T,P)$ is needed. This can be achieved by a higher water content.

The upper limit of the permissible water content is defined by the stickiness and mechanical failure of the capsules; a water content of 25% (0.25) by weight cannot be generally exceeded. The range within which capsules can be molded by the method of the present invention is therefore within 0.05 to 0.25 of water content. Better capsules are made with a water content in the range between 0.10 and 0.20; the best capsules were made with the water content in the range between 0.12 and 0.18.

The hydrophilic polymer in the mold will reduce its volume due to the temperature change $T_M - T_a$. This would result in voids and a diminution in the size of the capsule, which therefore would be unacceptable quality. It is an absolute requirement in capsule making that the dimensional deviations are less than 1%. To compensate for shrinking by the temperature change the mold must be filled at a distinct pressure $P_M$. This filling pressure is determined by the quantities $\alpha(T,P)$ and $\beta(T,P)$. The injection pressure ($P_E$) depends again on $T_E$, which as was shown already is in turn strongly dependent on X.

Figure 121:
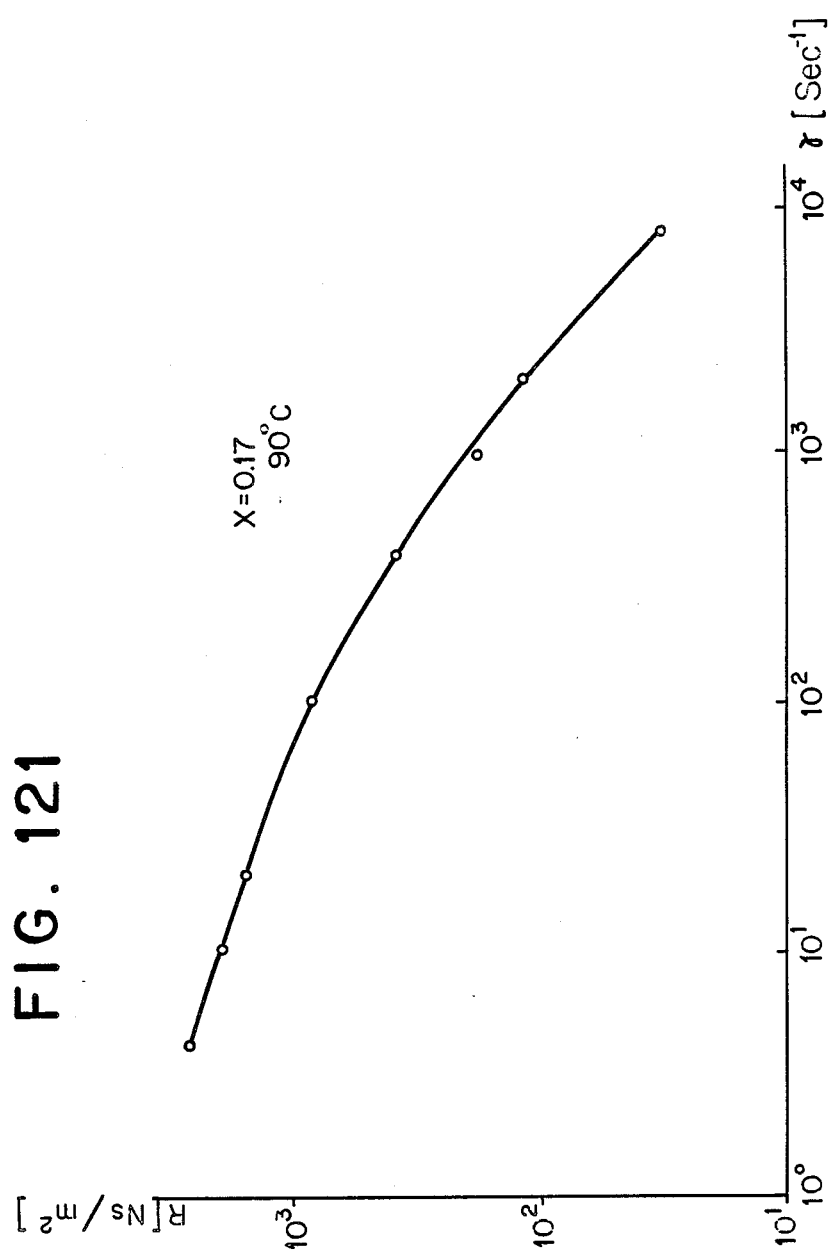
FIG. 121 is a graph illustrating the dependence of sheer viscosity of gelatin within the pertinent ranges of the sheer rate in the present invention.

Referring now to FIG. 121, the shear rate dependent shear viscosity of gelatin at 90° C. is shown for gelatin with a water content X of 0.17. The capillary has a diameter of 1.05 mm, and a length of 5.0 mm; the ratio of length to diameter is therefore L/D=4.75.

Figure 122:
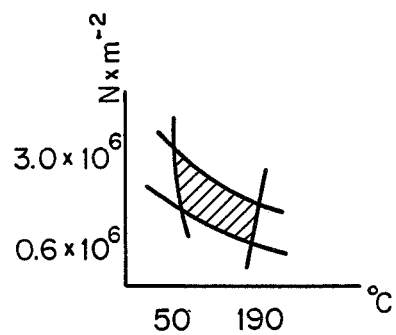
FIG. 122 is a graph illustrating the molding area for gelatin within the ranges of time, temperature, pressure and water content of gelatin for the present invention.

Referring now to FIG. 122, the molding area diagram for gelatin with a water content of 0.17, during injection molding the plasticized gelatin is discontinuously extruded and immediately cooled in a mold having the desired shape of the capsule part. Moldability depends on the gelatin properties and the process conditions, of which the thermomechanical properties of the gelatin as well as the geometry and the temperature and pressure conditions of the mold are the most important. In the molding area diagram of FIG. 122 the limits of pressure and temperature are indicated for the processing of gelatin in the combined injection molder-microprocessor of the present invention. The maximum temperature of 190° C. is determined by visible degradation of the gelatin above that limit. The lower temperature limit of 50° C. was determined by the development of too high viscosity and melt elasticity in the recommended water content range X: 0.05 to 0.25. The higher pressure limits of $3 \times 10^8$ N/m² are given by the start of flashing when the melted gelatin flows in a gap between the various metal dies which make up the molds, thus creating thin webs attached to the molded gelatin capsule parts at the separating lines. The lower pressure limits of about $6 \times 10^7$ N/m² are determined by short shots, when the mold cannot be completely filled by the gelatin.

The hydrophilic polymers, which are preferably various types of gelatin, are extruded and injected under the following conditions:

TABLE 3

WORKING PARAMETERS FOR INJECTION MOLDING PROCESS

| | |
|---|---|
| Density | $0.3-1.2 \times 10^3$ kg/m³ |
| Crystallinity | 25% |
| $H(T_n,P_n) - H(T_a,P_a)$ | 0.32 KJoule/kg[1] |
| Net heating performance for 10 kgs. melt/h (corresponding to $10^6$ capsules/h) | 3.2 KJoule |
| Heat conduction number | 1.0 KJoule/m × h × °C. |
| Compressibility ($T_E,P_E$) | $5 \times 10^{-10}$ N $- 1 \times$ m² |
| ($T_a,P_a$) | $8 \times 10^{-3}$/°C. |
| Contraction due to crystallization | negligible |
| Critical shear deformation rate | $10^4$–$10^5$/sec[1] |

Figure 123:
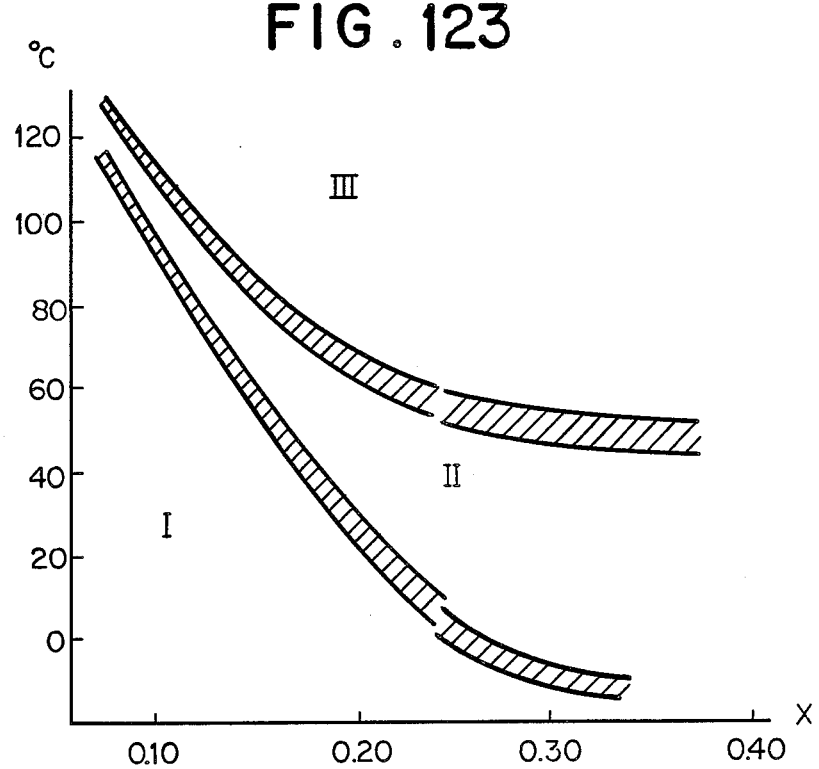
FIG. 123 is a graph illustrating the glass transition temperature range and melting temperature range for the pertinent water content ranges of the gelatin.

Referring now to FIG. 123 the glass transition range and the melting temperature range as a function of the composition of the gelatin-water system is shown. At temperatures below the glass transition range, ordinary gelatin, as available commercially, is a partially crystalline hydrophilic polymer containing approximately 70% amorphous and approximately 30% crystalline parts by volume (Area I in FIG. 123). Such gelatin preparations are commonly called cold dried gelatins. By raising the temperature of said gelatin preparation at a distinct water content, the gelatin passes through the glass transition range. Referring to FIG. 118, the heating process of the gelatin will take place within the extruder barrel 217.

Referring to FIG. 119, the heating process of the gelatin will take place during the entire injection molding work cycle. The area in FIG. 123 between the glass transition range and the melting range is called Area II. In Area II, crystalline gelatin and a gelatin melt are encountered. The glass-transition is not a thermodynamic transition range of any order, but it is characterized by a change in the molecular movement of the gelatin molecules and by a change of the bulk storage module of the amorphous gelatin by several orders of magnitude. By passing from Area II to Area I in FIG. 123, the translational movements of the gelatin molecules or those of large parts of the molecules will be frozen in the glass transition temperature range. This is reflected by a change in the specific heat ($c_p$) and the volumetric thermal expansion coefficient (a) in said temperature range. Upon passing from Area II to Area III, the helically ordered part of the gelatin will melt due to this crossing in the melting range of the crystalline gelatin. Referring to FIG. 118, the heating process of the gelatin will take place during the entire injection molding work cycle. This helix-coil transition is therefore a true thermodynamic transition of the first order.

Figure 124:
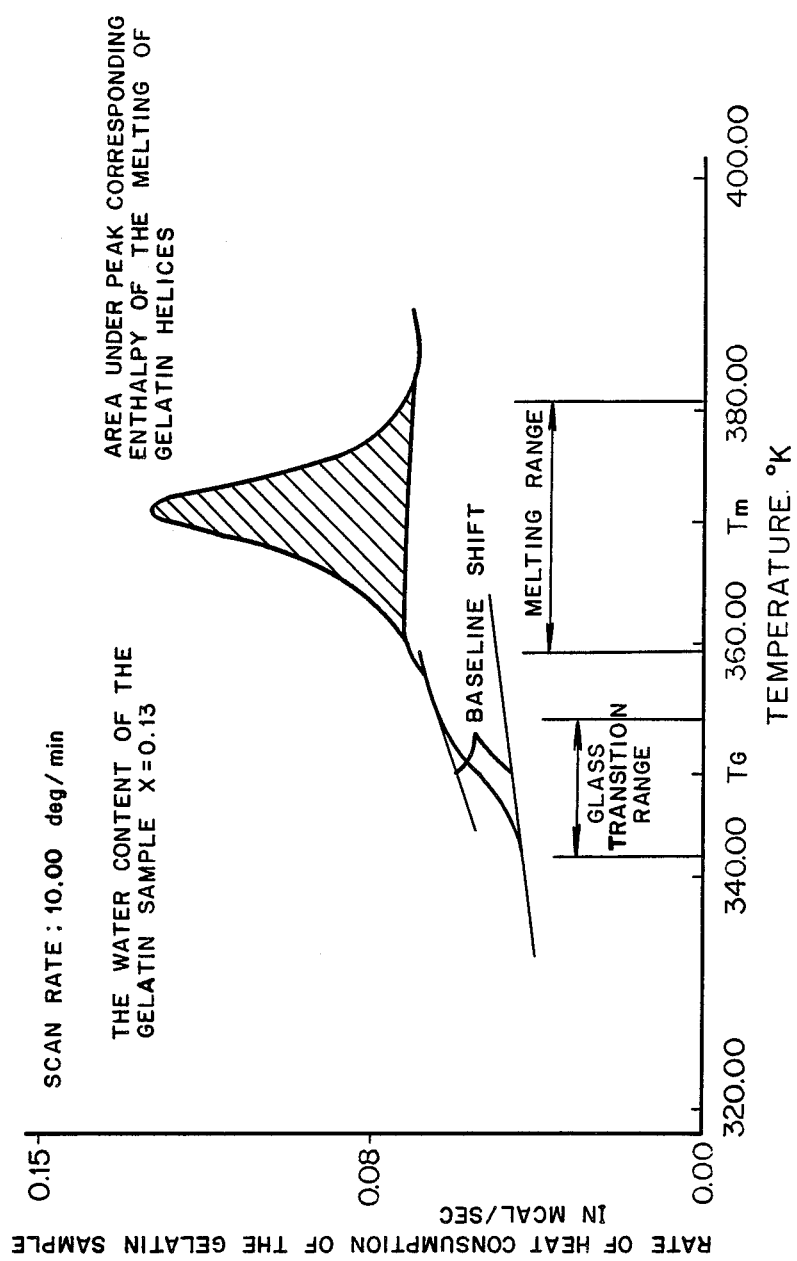
FIG. 124 is a graph illustrating the differential calorimeter scan in which the heat consumption rate of the gelatin is plotted for the pertinent temperature range of the present invention.
Figure 125:
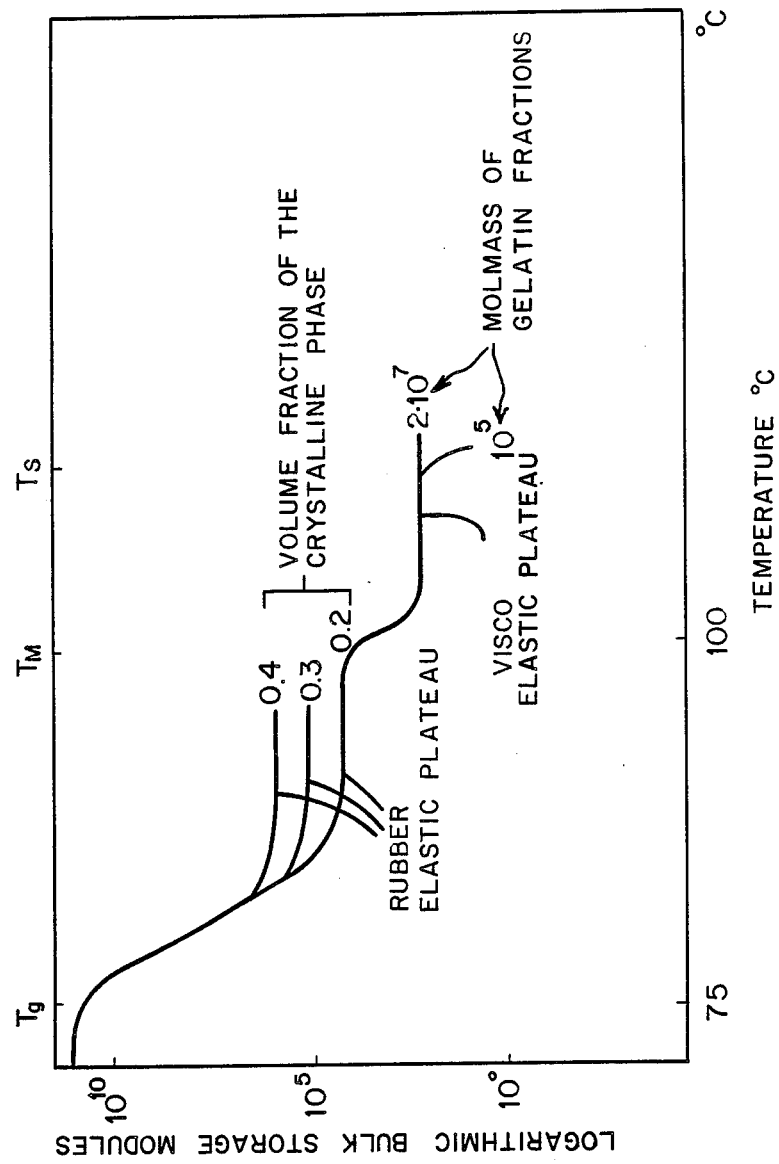
FIG. 125 is a graph illustrating the logarithmic bulk elastic storage module of the gelatin for the pertinent temperature range of the present invention.
Figure 127:
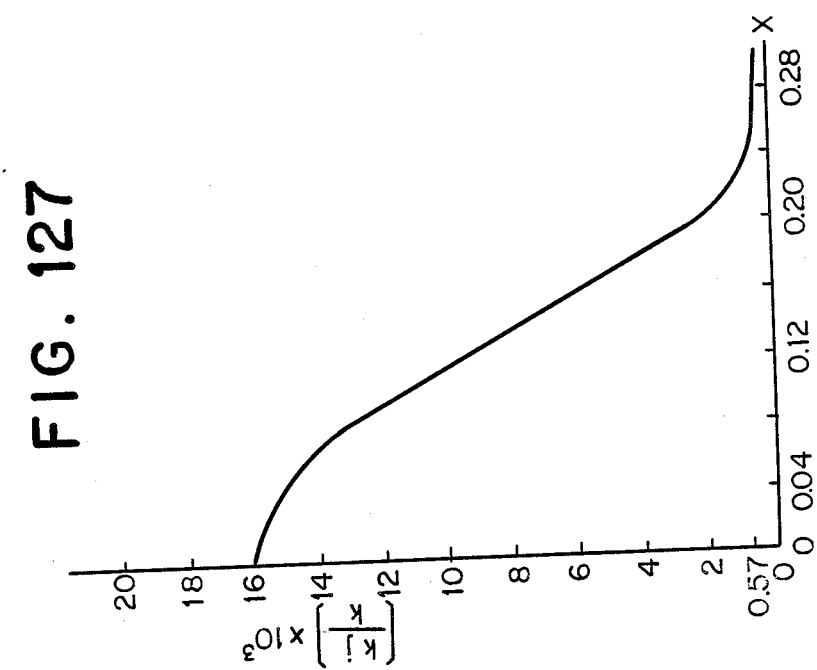
FIG. 127 is a graph illustrating the differential heat of water adsorption in the pertinent range of water content of the gelatin of the present invention.

Such transitions can be detected by scanning calorimetry or by measurement of the change in the linear viscoelastic bulk storage modulus due to changes in temperature. A typical plot of a temperature scan using a differential calorimeter is shown in FIG. 124. On the ordinate is plotted the velocity of the heat consumed by the sample relative to a reference (empty sample holder). The velocity of heat consumption of the sample is due to the change in the temperature of the gelatin sample, and said temperature is plotted on the abscissa as degrees Kelvin. The base line shift on said plot corresponds to the glass transition and the peak to the melting or to the helix-coil transition. The linear viscoelastic bulk storage module E can measure, at low sinusoidal shear, a deformation of the gelatin sample. The changes of the modulus of a typical gelatin sample at water content X=0.13 is plotted as a function of the sample temperature in FIG. 125. At the glass transition temperature and at the melting or helix-coil transition temperature, this modulus changes several orders of magnitude. As is shown in FIG. 125 there exist a further transition temperature above the melting range, and said transition is characterized by a further drop in said modulus E. The temperature of said transition is known as the solution temperature. In the temperature range $T_g$ to $T_M$ the gelatin is in the rubber elastic state and the crystalline ranges or fibrils represent the elastically active elements of the network.

Similar networks exist in plasticized microcrystalline polyvinylchloride (PVC). The crystalline regions give rise to diffraction patterns of X-rays in the PVC but not in the gelatin. In the temperature range $T_M$ to $T_S$, the gelatin is in the viscoelastic rubber-elastic state. The elastically active network in the state of the gelatin is, as in most polymer melts, a temporary network. This temporary network is due to entanglements of the polymer molecules. Specifically, in the gelatin, the strong interactions between the macromolecules (e.g., hydrogen-bridges, dipoldipol interactions) make important contributions to the elastically active temporary network. At the solution temperature, this temporary network disrupts and the gelatin molecules dissolve specifically due to the presence of water. At a temperature higher than $T_S$, the storage modulus drops to extremely low values: less than $10 \times Nm^{-2}$, as shown in FIG. 125. In the present invention, it was found that the processing (injection molding, blow molding etc.) of the gelatin should proceed at a temperature higher than $T_S$.

Referring again to FIG. 118, the heating of the gelatin to a temperature higher than $T_S$ takes place in the forward part of the extruder barrel 217. This heating process will be maintained not only be the steam heating coils 218 but to large degree by the internal friction during the injection process due to the high deformational rates. Referring to FIG. 119, this dissolution process occurs between points A and B of the work cycle. It was found that the reversible elastic deformation of the injection molded gelatin, after the opening of mold 206, is negligible if the temperature of the gelatin during the injection process is higher than $T_2$, otherwise the molding sequence would drop by at least an order of magnitude.

Referring to FIG. 119 the necessary cooling period for the gelatin in the molds—to prevent any reversible elastic deformation of said gelatin—will take place between points B and E of the working cycle. Restriction of the molding sequence to a low speed, coupled with an extended period of residence for the gelatin in the mold (longer than 5 seconds) is undesirable for two reasons: low output of the product and loss of water content by the gelatin in the extruder. At the elevated injection temperature there is always a movement of water from the hot to the cold gelatin in the extruder barrel. This water transport can be compensated for due to the movement of the gelatin by the screw in the opposite direction.

Figure 126:
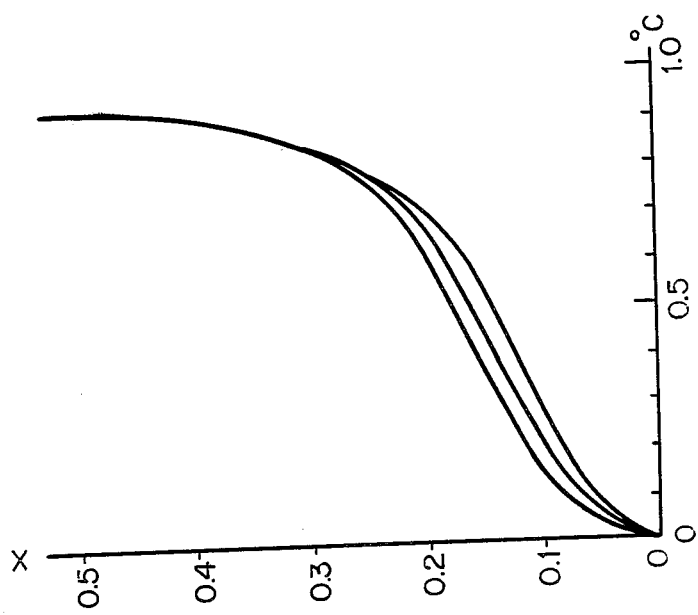
FIG. 126 is a graph illustrating the dependence of equilibrium water content of the gelatin in the entire water activity range.

Referring to FIG. 118 this movement of gelatin will be produced by screw 208. Referring now to FIG. 119 this transport of gelatin will take place between points A and B and further between points C and D of the working cycle. To build up the stationary water content in the gelatin in the melting area of the extruder barrel it is necessary to work at an injection sequence which is shorter than 5 seconds. To establish a constant and high enough water content of the gelatin in the extruder barrel it is further necessary to use gelatin or other hydrophilic polymers with the proper shape of both the sorption as a function of the water content (see FIG. 126). The constant water content of the gelatin in the extrude barrel is necessary due to the maintenance of constant production conditions. The water content of the gelatin during the injection must fulfill the condition: X higher than 0.05; otherwise $T_S$ is also higher than 190° C. and this is undesirable due to degradation of the gelatin. The sorption isotherm of the gelatin shows an S shape with an inflection point at about 0.5 water activity and the differential heat of sorption is a function which discusses with the water content. The condition to avoid is a phase separation of the gelatin-water phase into two liquid phases of gelatin-water and water. This phase separation may occur in the extruder barrel during injection and is avoided by providing that the water activity ($a_{W,M}$) of the gelatin (at the highest temperature in the extruder barrel and for the water content range of 0.05 to 0.25 of the gelatin) remain at a value less than one.

In utilizing the present invention, the processing temperature of a hydrophilic polymer may be reduced by at least 100° C., which means that the processing temperature $T_p$) may be shifted by incorporating sufficient water (X is more than 0.05 and less than 0.25) during the processing of said hydrophilic polymer leading to a temperature range of from 50° to 190° C. At this range, no degradation of the hydrophilic polymer takes place during processing. The melting range of a typical gelatin, with water content X, is less than 0.002 (which is a common water content during the processing of polyamides, whose chemical structure is similar to gelatin) between temperatures of 220° and 250° C. This melting range is again comparable with the melting range of aliphatic polyamides. Polyamides, for example, show a different behavior with respect to their compatibility with water during processing. The sorption isotherm of nylon 6, for example, has no inflection point. Its differential heat of sorption does not routinely decrease with the water content. At room temperature, the sorption isotherm shows an equilibrium water activity value equal to a water content for 0.05. If about 0.035 of water is incorporated into that polyamide at ambient temperature, a phase separation of the water and water-polyamide phases below 100° C. is noted. Because nylon 6 is not molten at the given water content and at temperatures below 100° C., the polyamide is not processable. At a water content of 0.035 and temperatures equal to or higher than 100° C., the polyamide is again not processable due to the syneresis of water in the extruder and the mold.

In the prior art procedures for branching and crosslinking hydrophilic polymers, preferably various types of gelatin, it is important to add the crosslinking agents, especially the covalent crosslinking agents, shortly before the injection of the molten hydrophilic polymers. Referring now to FIG. 125 it may be concluded that such an increase in the molecular weight of the hydrophilic polymers would raise the solution temperature of these polymers. Due to possible degradation at such elevated processing temperatures, it is not desirable to branch or crosslink these hydrophilic polymers before injection.

Referring to FIG. 118, an aqueous solution of crosslinking agents is injected in front of a mixing system which is placed between the melting and plasticizing unit 204 and the injection unit 201. The crosslinking reaction occurs mainly during the injection cycle and after the ejection of the capsule. There is therefore no disadvantage to changing the thermomechanical properties of the hydrophilic polymers during the melting and solution process.

The hydrophilic polymers useful for the invention, preferably various types of gelatin, are extruded and injected under the following conditions given in Table 3 below:

TABLE 4
INJECTION AND MOLDING CONDITIONS FOR HYDROPHILIC POLYMERS

| Injection Unit | | | | |
|---|---|---|---|---|
| Screw diameter mm | | 24 | 28 | 32 |
| Injection pressure N/m$^2$ | | 2.2 × 10$^8$ | 1.6 × 10$^8$ | 1.2 × 10$^8$ |
| Calculated injection cm$^3$ | | 38 | 51.7 | 67.5 |
| Effective screw length L:D | | 18.8 | 16.1 | 13.5 |
| Plasticising capacity (PS) | (1a) | 13.5 | 21.2 | 21.5 |
| kg/h(max.) | (11a) | 9.2 | 14.5 | 15 |
| | (1b) | 23.6 | 34 | 36 |
| | (11b) | 17.5 | 27 | 27 |
| Screw Stroke mm(max.) | | 84 | 84 | 84 |
| Injection capacity kW | | 30 | 30 | 30 |
| Injection velocity mm/s(max.) | | 460 | 460 | 460 |
| Nozzle contact force kN | | 41.2 | 41.2 | 41.2 |
| Screw rotating speed min$^{-1}$ | | Var. | | |
| | (1a) | | 20 | −280 |
| | (11a) | | 20 | −170 |
| | Var. | | | |
| | (1b) | | 20 | −600 |
| | (11b) | | 20 | −400 |
| Number of heating zones | | 5 | 5 | 5 |
| Installed heating capacity kW | | 6.1 | 6.1 | 6.1 |
| Molding Unit | | | | |
| Clamping force kN | | | | 600 |
| Opening stroke mm | | | 100 | −250 |

While the preferred embodiment of the injection molding-microprocessor apparatus in FIG. 118A is used for the method of producing capsules from various gelatin compositions, it has been found that high quality capsules may also be manufactured utilizing the present invention with gelatin, preferably of a lower quality, modified just before injection by covalent and/or non-covalent crosslinking agents such as: multi-valent metal salts such as aluminum and calcium salts, boric acid, potassium alum, ammonium alum and the like; metal salts of chromium, aluminum or zirconium (chromium acetate, chromium alum); aldehydes and ketones, as well as their halogenated derivatives such as formaldehyde, paraformaldehyde, 2,4,6,trinitro-benzaldehyde, quinones (benzoquinone), 1,2 and 1,3 dicarbonyl compounds such as glyoxal, cyclohexandon-1,2; 1,5 dialdehydes (glutaraldehyde); acids and acid anhydrides such as mucochloric acid, chlorides of 2-basic organic acids, anhydrides of tetracarboxylic acids; compounds with more than 2 easy-breaking heterocyclic 3-membered rings such as ethylene oxide and ethyleneimine; polyfunctional methene-sulfonic acid esters; non nitrogen polyfunctional compounds including ethylene glycoldimethacrylate, diepoxy butane, epichlorohydrin, dichloropropanol, diethylene glycoldimethacrylate, dichloromethyl and dichlorooctyl ethers and the like; nitrogen containing polyfunctional compounds as e.g. hexamethylene diisocyanate, dimethyl adipimate, bisdiazobenzidine, Woodward's reagent K, N,N'-(1,3-phenylene) bismaleimide, N,N'-ethylene-bis-(iodoacetamide), urea, trichloro-isocyanuric acid, ethylene-bismethacrylamide, tetrachloropyrimidine, dimethylol urea, dimethylol ethylene urea, methylol and dimethylol acrylamide as well as the following group of crosslinking agents:
carbodiimides;
sulfobetain carbodiimides;
carbamoyl oxypyridinium salts;
carbamoylonium salts;
1-N-ethoxy-carboxy-2-ethoxy-dihydrochinoline;
isoxazolium salts;
bis-isoxazolium salts; and
diisocyanates.

For the manufacture of capsules with the above described hydrophilic polymers, the addition of plasticizers, lubricants and coloring agents specifically of pharmaceutical grades leads to optimal product qualities.

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2 propyleneglycol, mono-, di-, tri-acetates of glycerol etc. may be utilized at various concentrations of about 0.5–40%, preferably at 0.5–10%, based upon the weight of the hydrophilic polymer.

Pharmacologically acceptable lubricants, such as the stearates of aluminum, calcium, magnesium and tin; as well as talc, silicones, etc. are to be used at concentrations of about 0.1–10% preferably at 0.1–5% based upon the weight of the hydrophilic polymer.

Pharmaceutically acceptable coloring agents, such as azo-dyes and other dyestuffs and pigments such as iron oxides, titanium dioxides, natural dyes, etc., are used at concentrations of about 0.001–10%, preferably at 0.001–5% based upon the weight of the hydrophilic polymer.

In addition, it has been found that the injection molding-microprocessor apparatus of the present invention can produce quality capsules with various grades of gelatin combined with 5–95% extenders by weight, such as: sunflower proteins, soybean proteins, cotton seed proteins, peanut proteins, rape seed proteins, lactose, gum arabic (a polysaccharaide of partially substituted 1,3 D-galactopyranose units), acrylates and methacrylates (eudragit), water soluble derivatives of cellulose, such as cellulose acetyl phthalate (CAP), hydroxypropyl cellulose, hydroxypropyl methycellulose, hydroxypropyl methylcellulosephthalate (HPMCP), hydroxymethylcellulose, polyvinyl pyrrolidone, shellac, bentonite, polyvinylacetatephthalate, phthalated gelatin, succinated gelatin, polysaccharides like agar-agar (an alternating co-polymer—D-galactopyranosyl and 3,6-anhydro- -L-galactopyranosyl residue linked in the 1,3 position).

For the manufacture of the capsules with the above described polymers, the utilization of plasticizers, lubricants and coloring agents, preferably of pharmaceutical grades, leads to optimal product qualities.

Pharmacologically acceptable plasticizers, such as polyethylene glycol or preferably low-molecular-weight organic plasticizers, like glycerol, sorbitol, dioctylsodium solfosuccinate, triethyl citrate, tributyl citrate, 1,2 propyleneglycol, mono-, di-, tri-acetates of glycerol, etc., are utilized at various concentrations of about 0.5–40% preferably at 0.5–10%, based upon the weight of the hydrophilic polymer.

Pharmacologically acceptable lubricants, such as the stearates of calcium, magnesium, tin, as well as talc, silicones, etc, are to be used at concentrations of about 0.1–10% preferably at 0.1–5% based upon the weight of the hydrophilic polymer.

Pharmacologically acceptable coloring agents, such as azo-dyes and other dyestuffs and pigments such as iron oxides, titanium dioxides, natural dyes etc. are used at concentrations of about 0.001–10%, preferably at 0.001–5% based upon the weight of the hydrophilic polymer.

In addition it has been found that improved capsules can be made with the injection molding-microprocessor apparatus utilizing the method of the present invention with other polymers having enteric properties (2 hours resistance in gastric juice, soluble within 30 min. in intestinal juice according to USP XX) such as: hydroxypropyl methylcellulosephthalate (HPMCP), polyvinylacetatephthalate (PVAP), celluloseacetylphthalate (CAP), acrylates and methacrylates (eudragit), phthalated gelatin, succinated gelatin, crotonic acid, and shellac. Such polymers having enteric properties may be combined with various grades of gelating and/or gelatin modified by covalent and non-covalent crosslinking agents or combinations of more than one covalent crosslinking agent or combinations of more than one covalent and non-covalent crosslinking agents, vegetable proteins such as sunflower proteins, soybean proteins, cottonseed proteins, peanut proteins, rape seed proteins, blood proteins egg proteins, and acetylated derivatives thereof, alginates (linear multiblock copolymers of blocks of -(1,4)-D-mannuronic acid and -(1,4)-L-gluronic acid as well as alternating copolymers of both these principal constituents, lactose, gum arabic, water soluble derivatives of cellulose hydroxypropylcellulose, hydroxypropymethylcellulose, hydroxymethylcellulose, polyvinyl pyrrolidone, and water soluble polysaccharides such as agar-agar.

For the manufacture of capsules with the above described polymers, the utilization of plasticizers, lubricants and coloring agents specifically of pharmaceutical grades leads to optimal product qualities.

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2 propyleneglecol, mono-, di-, tri-acetates of glycerol etc. are utilized at various concentrations of about 0.5–40% preferably at 0.5–10% based upon the weight of the hydrophilic polymer.

Pharmacologically acceptable lubricants, such as the stearates of aluminum, calcium, magnesium, tin, as well as talc, silicones, etc. are used at a concentration of about 0.1–10%, preferably at 0.–5% based upon the weight of the hydrophilic polymer.

In addition it has been found that high quality capsules can be made with the injection molding-microprocessor apparatus utilizing the method of the present invention with other polymers as gelatin substitutes such as: vegetable proteins, sunflower proteins, soybean proteins, cotton seed proteins, peanut proteins, rape seed proteins, blood proteins, egg proteins, and acetylated derivatives thereof and the like, alginates, lactose, gum arabic, water soluble derivatives of cellulose like hydroxyethylcellulose, hydroxypropylcellulose, hydroxypropylmethylcellulose, hydroxypropylcellulose, hydroxypropylmethylcellulose, other water soluble carbohydrates like agar-agar, other water soluble polymers like acrylic acid polymers, polyvinyl pyrrolidone and the like, and vinylacetate.

For the manufacture of capsules with the above described polymers, the utilization of plasticizers, lubricants and coloring agents, preferably of pharmaceutical grades, optimizes the product's qualities.

EXAMPLES

The scope of the invention is further described in connection with the following examples which are set out for the sole purpose of illustrating the preferred embodiments of the invention and which are not to be construed as limiting in any way the scope of the invention.

1. Series with bone gelatin No. 1 having various water contents

To test the method and apparatus of the present invention, batches of gelatin with different water contents were prepared, conditioned and then tested in an injection molding machine at different working conditions. The bone gelatin No. 1 had the following molecular mass mean values:

| | |
|---|---|
| Number (average): | 57000 Dalton |
| Viscosity (average): | 155000 Dalton |
| Weight (average): | 258000 Dalton |
| Centrifuge (average): | 5130000 Dalton |
| molecular mass of largest molecules; | $10^7$ Dalton |

A batch of this gelatin in granulated form, having granules of a mean diameter of 2 mm, was conditioned as follows: The gelatin, whose original water content was 0.105 was filled into a drum and sprayed with a fine spray of water to the calculated water content as desired for each experiment. Then, 1% by weight of calcium stearate was added as a lubricant. The batch was then thoroughly mixed and stored in the closed drum for three days at ambient temperature. Several different series of experiments were performed, each with a batch of gelatin having a different water content. The temperatures at different points in the molding characteristics and quality of the capsules are given below.

Referring to FIG. 119 the cycle times of the injection molding-microprocessor apparatus are as follows:

| Cycle Points | Times |
|---|---|
| A–B | variable, depending on temperature, see Table 3 |
| B–C (soak time) | 1 minute |
| C–D filling time | 1 sec |
| D–E | 5 sec |
| E–A | 1 sec |

Pressure in the nozzle: $1.94 \times 10^6 \, N \times m^{-2}$

Temperatures at different points of screw: variable, see Tables 4–12 below

Temperature at the nozzle: variable, See Tables 4–12 below.

In Table 4 below and the following tables for series A to I the abbreviations mean:
X water content of gelatin
$T_M$ melting temperature of the gelatin determined by differential scanning calorimetry
$T_b$ temperature at beginning of screw
$T_m$ temperature at middle of screw
$T_e$ temperature at end of screw
$T_g$ temperature at nozzle
LFV Linear flow velocity
L flow length
D film thickness.

EXAMPLE 1

Gelatin capsules containing 1% by weight of calcium stearate were prepared and processed according to the working conditions tabulated in Table 4 below:
Sample parameters: $T_M = 92.8°$ C.; $X = 0.136$.

TABLE 4

| | $T_b$ | $T_m$ | $T_e$ | $T_g$ | $\frac{L}{D}$ | LFV |
|---|---|---|---|---|---|---|
| A-1 | 105 | 110 | 110 | 100 | 114.73 | 72.4 |
| A-2 | 125 | 130 | 130 | 100 | 142.9 | 44.1 |

TABLE 4-continued

|     | $T_b$ | $T_m$ | $T_e$ | $T_g$ | $\frac{L}{D}$ | LFV |
| --- | --- | --- | --- | --- | --- | --- |
| A-3 | 135 | 150 | 150 | 100 | 171.4 | 40.0 |
| A-4 | 145 | 170 | 170 | 100 | 164.3 | 80.0 |

EXAMPLE 2

Gelatin capsules containing 1% by weight of calcium stearate were prepared and processed according to the working conditions tabulated in Table 5 below:
Sample parameters: $T_M = 86.8°$ C.; $X = 0.146$.

TABLE 5

|     | $T_b$ | $T_m$ | $T_e$ | $T_g$ | $\frac{L}{D}$ | LFV |
| --- | --- | --- | --- | --- | --- | --- |
| B-1 | 105 | 110 | 100 | 100 | 45.7 | 75.0 |
| B-2 | 125 | 130 | 130 | 100 | 135.7 | 28.2 |
| B-3 | 135 | 150 | 150 | 100 | 157.1 | 61.3 |
| B-4 | 145 | 170 | 170 | 100 | 92.8 | 88.9 |

EXAMPLE 3

Gelatin capsules containing 1% by weight of calcium stearate were prepared and processed according to the working conditions tabulated in Table 6 below:
Sample parameters: $T_M = 85.8°$ C.; $X = 0.166$.

TABLE 6

|     | $T_b$ | $T_m$ | $T_e$ | $T_g$ | $\frac{L}{D}$ | LFV |
| --- | --- | --- | --- | --- | --- | --- |
| C-1 | 105 | 110 | 110 | 100 | 92.9 | 66.7 |
| C-2 | 125 | 130 | 130 | 100 | 171.4 | 45.2 |
| C-3 | 135 | 150 | 150 | 100 | 157.1 | 24.7 |
| C-4 | 145 | 170 | 170 | 100 | 168.5 | 60.0 |

EXAMPLE 4

Gelatin capsules containing 1% by weight of calcium stearate were prepared and processed according to the working conditions tabulated in Table 7 below:
Sample parameters: $T_M = 80°$ C.; $X = 0.174$.

TABLE 7

|     | $T_b$ | $T_m$ | $T_e$ | $T_g$ | $\frac{L}{D}$ | LFV |
| --- | --- | --- | --- | --- | --- | --- |
| D-1 | 95 | 85 | 85 | 100 | 64.3 | 25.0 |
| D-2 | 100 | 90 | 90 | 100 | 78.6 | 26.3 |
| D-3 | 105 | 95 | 95 | 100 | 92.9 | 30.3 |

EXAMPLE 5

Gelatin capsules containing 1% by weight of calcium stearate were prepared and processed according to the working conditions tabulated in Table 8 below:
Sample parameters: $T_M = 75°$ C.; $X = 0.193$.

TABLE 8

|     | $T_b$ | $T_m$ | $T_e$ | $T_g$ | $\frac{L}{D}$ | LFV |
| --- | --- | --- | --- | --- | --- | --- |
| E-1 | 75 | 90 | 95 | 100 | 85.7 | 55.6 |
| E-2 | 85 | 95 | 100 | 100 | 100.0 | 71.4 |
| E-3 | 100 | 100 | 110 | 100 | 142.9 | 41.7 |
| E-4 | 100 | 130 | 120 | 100 | 135.7 | 60.7 |
| E-5 | 130 | 150 | 130 | 100 | 157.1 | 51.9 |
| E-6 | 145 | 170 | 170 | 100 | 159.2 | 66.7 |

EXAMPLE 6

Gelatin capsules containing 1% by weight of calcium stearate were prepared and processed according to the working conditions tabulated in Table 9 below:
Sample parameters: $T_M = 70°$ C.; $X = 0.208$.

TABLE 9

|     | $T_b$ | $T_m$ | $T_e$ | $T_g$ | $\frac{L}{D}$ | LFV |
| --- | --- | --- | --- | --- | --- | --- |
| F-1 | 70 | 85 | 90 | 95 | 57.1 | 35.6 |
| F-2 | 75 | 90 | 95 | 100 | 52.9 | 30.8 |
| F-3 | 85 | 95 | 100 | 105 | 64.3 | 29.6 |
| F-4 | 100 | 100 | 110 | 110 | 100.0 | 25.8 |
| F-5 | 100 | 140 | 120 | 100 | 114.3 | 27.1 |

EXAMPLE 7

A further batch of gelatin in combination with water and a plasticizer was prepared and conditioned and then tested in an injection molding device at different working conditions. A batch of bone gelatin No. 1 in granulated form, with granules having a mean diameter of 2 mm, was conditioned as follows: The gelatin, whose water content was 10.54%, was filled into a drum and sprayed with a fine spray of a mixture consisting of water and glycerol as a plasticizer to the calculated content as desired. Then 1% by weight of calcium stearate was added as a lubricant. The gelatin was then processed according to the working conditions tabulated in Table 10 below.
Sample parameters: $T_M = 9°$ C. $X = 0.15$.
Glycol content 3.5% by weight.

TABLE 10

|     | $T_b$ | $T_m$ | $T_e$ | $T_g$ | $\frac{L}{D}$ | LFV |
| --- | --- | --- | --- | --- | --- | --- |
| G-1 | 105 | 110 | 110 | 100 | 151.4 | 50.0 |
| G-2 | 125 | 130 | 130 | 100 | 171.4 | 40.0 |
| G-3 | 135 | 150 | 150 | 100 | 178.5 | 53.8 |
| G-4 | 145 | 170 | 170 | 100 | 170.0 | 57.1 |

Pigskin gelatin No. 2 having the following molecular mass mean values was used in Examples 8 and 9:

| Number (average): | 34000 Dalton |
| --- | --- |
| Viscosity (average): | 65000 Dalton |
| Weight (average): | 80000 Dalton |
| Centrifuge (average): | 1450000 Dalton |
| Molecular mass of largest molecules: | $2 \times 10^6$ Dalton |

EXAMPLE 8

Gelatin capsules containing 1% by weight of calcium stearate were prepared and processed according to the working conditions tabulated in Table 11 below:
Sample parameters $T_M = 80°$ C. $X = 0.167$.
Glycol content 3.5% by weight.

TABLE 11

|     | $T_b$ | $T_m$ | $T_e$ | $T_g$ | $\frac{L}{D}$ | LFV |
| --- | --- | --- | --- | --- | --- | --- |
| H-1 | 105 | 110 | 110 | 100 | 164.3 | 52.9 |

EXAMPLE 9

Gelatin capsules containing 1% by weight of calcium stearate were prepared and processed according to the working conditions tabulated in Table 12 below:

Sample parameters $T_M = 70°$ C.; $X = 0.202$.

TABLE 12

|     | $T_b$ | $T_m$ | $T_e$ | $T_g$ | $\frac{L}{D}$ | LFV |
|-----|-----|-----|-----|-----|-----|-----|
| I-1 | 80  | 90  | 90  | 100 | 117.1 | 59.1 |
| I 2 | 105 | 110 | 110 | 100 | 135.7 | 90.0 |

EXAMPLE 10

A batch of bone gelatin 80 bloom, grade A, in granulated form was conditioned as follows:

The gelatin, having a water content of 13%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 13 below:

Material Composition: gelatin 80A: 85.3%; water: 14.7%.

TABLE 13

| $T_b$ | $T_m$ | $T_e$ | $T_g$ | $\frac{L}{D}$ | LFV |
|-----|-----|-----|-----|-----|-----|
| 110 | 125 | 135 | 135 | 66 | 840 |

EXAMPLE 11

A batch of bone gelatin 150 bloom, grade A, in granulated form was conditioned as follows:

The gelatin, having a water content of 12%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 14 below:

Material Composition: gelatin 150A: 84.5%; water: 15.5%.

TABLE 14

| $T_b$ | $T_m$ | $T_e$ | $T_g$ | $\frac{L}{D}$ | LFV |
|-----|-----|-----|-----|-----|-----|
| 110 | 120 | 140 | 140 | 66 | 820 |

EXAMPLE 12

A batch of bone gelatin 150 bloom, grade A, in granulated form was conditioned as follows:

The gelatin, with a water content of 12%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 15 below:

Material Composition: gelatin 150A: 80.3%; water: 19.7%.

TABLE 15

| $T_b$ | $T_m$ | $T_e$ | $T_g$ | $\frac{L}{D}$ | LFV |
|-----|-----|-----|-----|-----|-----|
| 110 | 120 | 140 | 140 | 66 | 810 |

EXAMPLE 13

A batch of bone gelatin 240 bloom, grade A, in granulated form was conditioned as follows:

The gelatin, having a water content of 10%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed on Table 16 below:

Material Composition: gelatin 150A: 85%; water: 15%.

TABLE 16

| $T_b$ | $T_m$ | $T_e$ | $T_g$ | $\frac{L}{D}$ | LFV |
|-----|-----|-----|-----|-----|-----|
| 125 | 135 | 140 | 140 | 66 | 824 |

EXAMPLE 14

A batch of bone gelatin 240 bloom, grade A, in granulated form was conditioned as follows:

The gelatin, having a water content of 10%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 17 below:

Material Composition: gelatin 150A: 85%; water: 15%.

TABLE 17

| $T_b$ | $T_m$ | $T_e$ | $T_g$ | $\frac{L}{D}$ | LFV |
|-----|-----|-----|-----|-----|-----|
| 125 | 135 | 140 | 140 | 66 | 806 |

EXAMPLE 15

A batch of bone gelatin 150 bloom, grade B, in granulated form was conditioned as follows:

The gelatin, having a water content of 12%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 18 below:

Material Composition: gelatin 150A: 85%; water: 15%.

TABLE 18

| $T_b$ | $T_m$ | $T_e$ | $T_g$ | $\frac{L}{D}$ | LFV |
|-----|-----|-----|-----|-----|-----|
| 125 | 135 | 140 | 140 | 66 | 840 |

Example 16

A batch of bone gelatin 150 bloom, grade B, in granulated form was conditioned as follows:

The gelatin, having a water content of 12%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 19 below:

Material Composition: gelatin 150B: 81.7%; water: 18.3%.

TABLE 19

| $T_b$ | $T_m$ | $T_e$ | $T_g$ | $\frac{L}{D}$ | LFV |
|---|---|---|---|---|---|
| 110 | 130 | 130 | 130 | 66 | 835 |

EXAMPLE 17

A batch of bone gelatin 200 bloom, grade B, in granulated form was conditioned as follows:

The gelatin, having a water content of 10% was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 20 below:

Material Composition: gelatin 150B: 81.7%; water: 18.3%.

TABLE 20

| $T_b$ | $T_m$ | $T_e$ | $T_g$ | $\frac{L}{D}$ | LFV |
|---|---|---|---|---|---|
| 125 | 135 | 140 | 140 | 66 | 820 |

EXAMPLE 18

A batch of bone gelatin 200 bloom, grade B, in granulated form was conditioned as follows:

The gelatin, having a water content of 10%, was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 21 below:

Material Composition: gelatin 150B: 81.7%; water: 18.3%.

TABLE 21

| $T_b$ | $T_m$ | $T_e$ | $T_g$ | $\frac{L}{D}$ | LFV |
|---|---|---|---|---|---|
| 115 | 125 | 130 | 130 | 66 | 830 |

EXAMPLE 19

A batch of bone gelatin 150 bloom, grade B, in granulated form was mixed with 8% by weight of microcrystalline cellulose and conditioned as follows:

The gelatin, having a water content of 11.7%, and the microcrystalline cellulose were combined in a drum and sprayed with a fine spray of water to obtain the calculated content as desired. The 8% by weight of microcrystalline cellulose was added as an extender. The batch was then thoroughly mixed and stored in the closed drum for half a day a ambient temperature. Acceptable gelatin capsules were then produced according to the working conditions listed in Table 22 below:

Material Composition: gelatin 150B: 81.7%; water: 18.3%.

TABLE 22

| $T_b$ | $T_m$ | $T_e$ | $T_g$ | $\frac{L}{D}$ | LFV |
|---|---|---|---|---|---|
| 125 | 130 | 140 | 140 | 66 | 1200 |

EXAMPLE 20

A batch of bone gelatin 150 bloom, grade B, in granulated form was mixed with 25% by weight of microfine cellulose and conditioned as follows:

The gelatin, having a water content of 11.7%, and the microfine cellulose were combined in a drum and sprayed with a fine spray of water to obtain the calculated content as desired. The micro fine cellulose was added as an extender. The batch was then thoroughly mixed and stored in the closed drum for half a day at ambient temperature. Acceptable gelatin capsules were then produced according to the working conditions listed in Table 23 below:

Material Composition: 150B: 81.7%; water: 18.3%.

TABLE 23

| $T_b$ | $T_m$ | $T_e$ | $T_g$ | $\frac{L}{D}$ | LFV |
|---|---|---|---|---|---|
| 115 | 125 | 130 | 130 | 66 | 840 |

EXAMPLE 21

A batch of bone gelatin 150 bloom, grade B, in granulated form was conditioned as follows:

The gelatin, having a water content of 11.7% and 8% by weight of microfine cellulose were combined in a drum and sprayed with a fine spray of water to obtain the calculated content as desired. The microfine cellulose was added as an extender.

The batch was then thoroughly mixed and stored in the closed drum for half a day at ambient temperature. Acceptable gelatin capsules were then produced according to the working conditions listed in Table 24 below:

Material Composition: gelatin 150B: 81.7%; water: 18.3%.

TABLE 24

| $T_b$ | $T_m$ | $T_e$ | $T_g$ | $\frac{L}{D}$ | LFV |
|---|---|---|---|---|---|
| 125 | 130 | 140 | 140 | 66 | 1000 |

EXAMPLE 22

A batch of bone gelatin 150 bloom, grade B, in granulated form was conditioned as follows:

The gelatin, having a water content of 11.7%, and 8% by weight of microfine cellulose were combined in a drum and sprayed with a fine spray of water to obtain the calculated content as desired. The microfine cellulose was added as an extender. The batch was then thoroughly mixed and stored in the closed drum for half a day at ambient temperature. Acceptable gelatin capsules were then produced according to the working conditions listed in Table 25 below:

Material Composition: microfine cellulose: 25%; gelatin 150B: 59%; water: 16%.

TABLE 25

| $T_b$ | $T_m$ | $T_e$ | $T_g$ | $\frac{L}{D}$ | LFV |
|---|---|---|---|---|---|
| 125 | 135 | 140 | 140 | 66 | 820 |

EXAMPLE 23

A batch of bone gelatin 150 bloom, grade B, in granulated form was conditioned as follows:

The gelatin, having a water content of 11.7%, and 9% by weight of microfine cellulose were combined in a drum and sprayed with a fine spray of water to obtain the calculated content as desired. The microfine cellulose was added as an extender. The batch was then thoroughly mixed and stored in the closed drum for half a day at ambient temperature. Acceptable gelatin capsules were then produced according to the working conditions listed in Table 26 below:

Material Composition: microfine cellulose: 9%; gelatin 150B; 76%; water: 15%.

TABLE 26

| $T_b$ | $T_m$ | $T_e$ | $T_g$ | $\frac{L}{D}$ | LFV |
|---|---|---|---|---|---|
| 125 | 135 | 140 | 140 | 66 | 920 |

EXAMPLE 24

A batch of bone gelatin 150 bloom, grade B, in granulated form was conditioned as follows:

The gelatin, having a water content of 11.7%, and the cellulose acetate phthalate were combined in a drum and sprayed with a fine spray of water to obtain the calculated content as desired. The batch was the then thoroughly mixed and stored in the closed drum for half a day at ambient temperature. Acceptable gelatin capsules were then produced according to the working conditions listed in Table 27 below:

Material Composition: cellulose acetate phthalate: 43%; gelatin 150B: 43%; water: 14%.

TABLE 27

| $T_b$ | $T_m$ | $T_e$ | $T_g$ | $\frac{L}{D}$ | LFV |
|---|---|---|---|---|---|
| 125 | 135 | 140 | 140 | 66 | 760 |

The 43% by weight of cellulose acetate phthalate was added as an enteric polymer.

The resulting capsules have enteric properties (2 hours resistance in gastric juice, soluble well within 30 minutes in intestinal juice, according to USP XX).

EXAMPLE 25

A batch of bone gelatin 150 bloom, grade B, in granulated form was conditioned as follows:

The gelatin, having a water content of 11.7%, and 8% by weight of cellulose acetate phthalate were combined in a drum and sprayed with a fine spray of water to obtain the calculated content as desired. The cellulose acetate phthalate was added as an enteric polymer. The batch was then thoroughly mixed and stored in the closed drum for half a day at ambient temperature. Acceptable gelatin capsules were then produced according to the working conditions listed in Table 28 below:

Material Composition: cellulose acetate phthalate: 8%; gelatin 150B: 72%; water: 20%.

TABLE 28

| $T_b$ | $T_m$ | $T_e$ | $T_g$ | $\frac{L}{D}$ | LFV |
|---|---|---|---|---|---|
| 125 | 135 | 140 | 140 | 66 | 800 |

EXAMPLE 26

A batch of HPMCP with water and glycerin, polyethylene glycol and calcium-stearate was prepared, conditioned and then tested in an injection molding machine. The batch of HPMCP in powdered form was conditioned as follows:

The HPMCP, having a water content of 2%, and the other additives were combined in a drum and sprayed with a fine spray of water to obtain the calculated content as desired. The batch was then thoroughly mixed and stored in a closed drum for half a day at ambient temperature.

Acceptable capsules were then produced according to the working conditions listed in Table 29 below:

Material Composition: MPMCP: 89%; glycerin: 6.4%; PE-glycol (10.000): 1.6%; Ca-stearate: 3%.

TABLE 25

| $T_b$ | $T_m$ | $T_e$ | $T_g$ | $\frac{L}{D}$ | LFV |
|---|---|---|---|---|---|
| 125 | 135 | 140 | 140 | 66 | 820 |

The 6.4% by weight of glycerin was added as a softener. The 1.6% by weight of polyethyleneglycol was added as plasticizer.

The 3% by weight of calcium-stearate was added as a lubricant.

The resulting capsules have enteric properties (2 hours resistance in gastric juice, soluble well within 30 minutes of intestinal juice according to USP XX).

EXAMPLE 27

A batch of gelatin with water and HPMCP, glycerin, polyethylene glycol and Ca-stearate was prepared, conditioned and then tested in an injection molding machine. The batch of bone gelatin 150 bloom, grade B, in granulated form was conditioned as follows:

The gelatin, having a water content of 11.7% and the other additives were combined in a drum and sprayed with a fine spray of water to obtain the calculated content as desired. The batch was then thoroughly mixed and stored in a closed drum for half a day at ambient temperature. Acceptable capsules were then produced according to the working conditions listed in Table 30 below:

Material Composition: MPMCP: 40%; glycerin: 3%; PE-glycol (10,000): 1%; Ca-stearate: 1%; gelatin 150B: 45%; water: 10%.

TABLE 25

| $T_b$ | $T_m$ | $T_e$ | $T_g$ | $\frac{L}{D}$ | LFV |
|---|---|---|---|---|---|
| 125 | 135 | 140 | 140 | 66 | 820 |

The 3% by weight of glycerin and the 1% by weight of polyethyleneglycol were added as a plasticizer.

The 1% by weight of Ca-stearate was added as a lubricant. The 40% by weight of HPMCP was added as an enteric polymer. The resulting capsules have enteric properties (2 hours resistance in gastric juice, soluble well within 30 minutes of intestinal juice according to USP XX).

EXAMPLE 28

A batch of gelatin with water and 8% by weight of HPMCP was prepared, conditioned and then tested in an injection molding machine. A batch of bone gelatin 150 bloom, grade B, in granulated form was conditioned as follows:

The gelatin, having a water content of 11.7%, and the HPMCP were combined in a drum and sprayed with a fine spray of water to obtain the calculated content as desired. The HPMCP was added as an enteric polymer. The batch was then thoroughly mixed and stored in the closed drum for half a day at ambient temperature. Acceptable gelatin capsules were then produced according to the working conditions listed in Table 31 below:

Material Composition: HPMCP: 8%; gelatin 150B: 72%, water: 20%.

TABLE 31

| $T_b$ | $T_m$ | $T_e$ | $T_g$ | $\frac{L}{D}$ | LFV |
|---|---|---|---|---|---|
| 118 | 125 | 130 | 130 | 66 | 1000 |

EXAMPLE 29

A batch of acrylate with water was prepared, conditioned and then tested in an injection molding machine. The batch was conditioned in powdered form as follows:

The acrylate, having a water content of 4%, was placed in a drum and sprayed with a fine spray of water to obtain the calculated content as desired. The batch was then thoroughly mixed and stored at ambient temperature. Acceptable capsules were then produced according to the working conditions listed in Table 32 below:

Material Composition: acrylate: 83%; water: 17%.

TABLE 32

| $T_b$ | $T_m$ | $T_e$ | $T_g$ | $\frac{L}{D}$ | LFV |
|---|---|---|---|---|---|
| 120 | 140 | 140 | 140 | 66 | 850 |

The resulting capsules have enteric properties (2 hours resistance in gastric juice, soluble well within 30 minutes in intestinal juice according to USP XX).

EXAMPLE 30

A batch of bone gelatin 150 bloom, grade B, in granulated form was conditioned as follows:

The gelatin, having a water content of 11.7%, was mixed with 25% by weight of acrylate in a drum and sprayed with a fine spray of water to obtain the calculated content as desired. The acrylate was added as an enteric polymer. The batch was then thoroughly mixed and stored in the closed drum for half a day at ambient temperature. Acceptable gelatin capsules were then produced according to the working conditions listed in Table 33 below:

Material Composition: acrylate: 25%; gelatin 150B: 59%; water: 16%.

TABLE 33

| $T_b$ | $T_m$ | $T_e$ | $T_g$ | $\frac{L}{D}$ | LFV |
|---|---|---|---|---|---|
| 105 | 115 | 120 | 120 | 66 | 860 |

EXAMPLE 31

A batch of bone gelatin 150 bloom, grade B, in granulated form was conditioned as follows:

The gelatin, having a water content of 11.7%, was mixed with 8% by weight of acrylate, combine in a drum and sprayed with a fine spray of water to obtain a content as desired. The batch was then thoroughly mixed and stored in the closed drum for half a day at ambient temperature. Acceptable gelatin capsules were then produced according to the working conditions listed in Table 34 below:

Material Composition: acrylate: 8%; gelatin 150B: 76%; water: 16%.

TABLE 34

| $T_b$ | $T_m$ | $T_e$ | $T_g$ | $\frac{L}{D}$ | LFV |
|---|---|---|---|---|---|
| 125 | 135 | 140 | 140 | 66 | 900 |

The acrylate was added as an enteric polymer.

EXAMPLE 32

A batch of bone gelatin 150 bloom, grade B, in granulated form was conditioned as follows:

The gelatin, having a water content of 11.7%, along with 39% by weight of soy protein was combined in a drum and sprayed with a fine spray of water to obtain a content as desired. The batch was then thoroughly mixed and stored in the closed drum for half a day at ambient temperature. Acceptable gelatin capsules were then produced according to the working conditions listed in Table 35 below:

Material Composition: soy protein: 39%; gelatin 150B: 39%; water: 22%.

TABLE 35

| $T_b$ | $T_m$ | $T_e$ | $T_g$ | $\frac{L}{D}$ | LFV |
|---|---|---|---|---|---|
| 125 | 135 | 140 | 140 | 66 | 780 |

The 39% weight of soy protein was added as an extender.

EXAMPLE 33

A batch of bone gelatin 150 bloom, grade B, in granulated form was mixed with 8% by weight of soy protein and conditioned as follows:

The gelatin, with a water content of 11.7% was mixed with the soy protein in a drum and sprayed with a fine spray of water to obtain the calculated content as desired. The soy protein was added as an extender. The batch was then thoroughly mixed and stored in the closed drum for half a day at ambient temperature. Acceptable gelatin capsules were then produced according to the working conditions listed in Table 36 below:

Material Composition: soy protein: 8%; gelatin 150B: 76% water: 16%.

TABLE 36

| $T_b$ | $T_m$ | $T_e$ | $T_g$ | $\frac{L}{D}$ | LFV |
|---|---|---|---|---|---|
| 125 | 135 | 140 | 140 | 66 | 840 |

EXAMPLE 34

A batch of bone gelatin 150 bloom, grade B, in granulated form was conditioned as follows:

The gelatin, having a water content of 11.7% was mixed with 44% by weight of HPMC additive in a drum and sprayed with a fine spray of water obtain to the calculated content as desired. The hydroxy-propyl-methyl-cellulose was added as an extender. The batch was then thoroughly mixed and stored in the closed drum for half a day at ambient temperature. Acceptable gelatin capsules were then produced according to the working conditions listed in Table 37 below:

Material Composition: HPMC: 44; gelatin 150B: 44; water: 12.

TABLE 37

| $T_b$ | $T_m$ | $T_e$ | $T_g$ | $\frac{L}{D}$ | LFV |
|---|---|---|---|---|---|
| 135 | 145 | 150 | 150 | 66 | 850 |

EXAMPLE 35

A batch of bone gelatin 150 bloom, grade B, in granulated form was conditioned as follows:

The gelatin, having a water content of 11.7% was mixed with 8% by weight of HPMC additive in a drum and sprayed with a fine spray of water to obtain the calculated content as desired. The hydroxy-propylmethyl-cellulose was added as an extender. The batch was then thoroughly mixed and stored in the closed drum for half a day at ambient temperature. Acceptable gelatin capsules were then produced according to the working conditions listed in Table 38 below:

Material Composition: HPMC: 8%; gelatin 150B: 75%; water: 17%.

TABLE 28

| $T_b$ | $T_m$ | $T_e$ | $T_g$ | $\frac{L}{D}$ | LFV |
|---|---|---|---|---|---|
| 125 | 135 | 140 | 140 | 66 | 800 |

EXAMPLE 36

A batch of bone gelatin 150 bloom, grade B, in granulated form was conditioned as follows:

The gelatin, having a water content of 11.7% was mixed with 40% by weight of a Na-CMC additive in a drum and sprayed with a fine spray of water to obtain the calculated content as desired. The Na-CMC was added as an extender. The batch was then thoroughly mixed and stored in the closed drum for half a day at ambient temperature. Acceptable gelatin capsules were then produced according to the working conditions listed in Table 39 below:

Material composition: NA-CMC: 40%; gelatin 150B: 40% water: 20%.

TABLE 36

| $T_b$ | $T_m$ | $T_e$ | $T_g$ | $\frac{L}{D}$ | LFV |
|---|---|---|---|---|---|
| 125 | 135 | 140 | 140 | 66 | 840 |

EXAMPLE 37

A batch of bone gelatin 150 bloom, grade B, in granulated form was conditioned as follows:

The gelatin, having a water content of 11.7% was mixed with 8% by weight of Na-CMC additive in a drum and sprayed with a fine spray of water to obtain the calculated content as desired. The Na-CMC was added as an extender. The batch was then thoroughly mixed and stored in the closed drum for half a day at ambient temperature. Acceptable gelatin capsules were then produced according to the working conditions listed on Table 40 below:

Material Composition: NA-CMC: 8%; gelatin 150B: 75% water: 17%.

TABLE 40

| $T_b$ | $T_m$ | $T_e$ | $T_g$ | $\frac{L}{D}$ | LFV |
|---|---|---|---|---|---|
| 125 | 135 | 140 | 140 | 66 | 825 |

EXAMPLE 38

A batch of bone gelatin 150 bloom, grade B, in granulated form was conditioned as follows:

The gelatin, having a water content of 11.7% was mixed with 25% by weight of polyvinylpyrrolidone additive in a drum and sprayed with a fine spray of water to obtain the calculated content as desired. The polyvinylpyrrolidone was added as an extender. The batch was then thoroughly mixed and stored in the closed drum for half a day at ambient temperature. Acceptable gelatin capsules were then produced according to the working conditions listed in Table 41 below:

Material Composition: polyvinylpyrrolindone: 25%; gelatin 150B: 60%; water: 15%.

TABLE 25

| $T_b$ | $T_m$ | $T_e$ | $T_g$ | $\frac{L}{D}$ | LFV |
|---|---|---|---|---|---|
| 125 | 135 | 140 | 140 | 66 | 820 |

EXAMPLE 39

A batch of bone gelatin 150 bloom, grade B, in granulated form was conditioned as follows:

The gelatin, having a water content of 11.7% was mixed with 9% by weight of polyvinylpyrrolidone additive in a drum and sprayed with a fine spray of water to obtain the calculated content as desired. The polyvinylpyrrolidone was added as an extender. The batch was then thoroughly mixed and stored in the closed drum for half a day at ambient temperature. Acceptable gelatin capsules were then produced according to the working conditions listed in Table 42 below:

Material Composition: polyvinylpyrrolindone: 9%; gelatin 150B: 77%; water: 14%.

TABLE 42

| $T_b$ | $T_m$ | $T_e$ | $T_g$ | $\frac{L}{D}$ | LFV |
|---|---|---|---|---|---|
| 125 | 135 | 140 | 140 | 66 | 860 |

EXAMPLE 40

A batch of bone agar in powdered form was conditioned as follows: The agar, having a water content of 16% was filled into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 43 below:

Material Composition: agar: 75%; water: 25%.

TABLE 43

| $T_b$ | $T_m$ | $T_e$ | $T_g$ | $\frac{L}{D}$ | LFV |
|---|---|---|---|---|---|
| 110 | 120 | 130 | 130 | 66 | 1240 |

EXAMPLE 41

A batch of bone gelatin 150 bloom, grade B, in granulated form was conditioned as follows:

The gelatin, having a water content of 11.7% was mixed with 38% by weight of agar additive in a drum and sprayed with a fine spray of water to obtain the calculated content as desired. The agar was added as extender. The batch was then thoroughly mixed and stored in the closed drum for half a day at ambient temperature. Acceptable gelatin capsules were then produced according to the working conditions listed in Table 44 below:

Material Composition: agar: 38%; gelatin 150B: 38%; water: 24%.

TABLE 44

| $T_b$ | $T_m$ | $T_e$ | $T_g$ | $\frac{L}{D}$ | LFV |
|---|---|---|---|---|---|
| 110 | 120 | 130 | 130 | 66 | 820 |

EXAMPLE 42

A batch of bone gelatin 150 bloom, grade B, in granulated form was conditioned as follows:

The gelatin, having a water content of 11.7% was mixed with 8% by weight of agar additive in a drum and sprayed with a fine spray of water to obtain the calculated content as desired. The agar was added as extender. The batch was then thoroughly mixed and stored in the closed drum for half a day at ambient temperature. Acceptable gelatin capsules were then produced according to the working conditions listed in Table 45 below:

Material Composition: agar: 8%; gelatin 150B: 73%; water: 19%.

TABLE 45

| $T_b$ | $T_m$ | $T_e$ | $T_g$ | $\frac{L}{D}$ | LFV |
|---|---|---|---|---|---|
| 110 | 120 | 130 | 130 | 66 | 820 |

EXAMPLE 42a

A batch of bone gelatin 150 bloom, grade B, in granulated form was conditioned as follows:

The gelatin, with a water content of 11.7% was mixed with 8% by weight of agar additive in a drum and sprayed with a fine spray of water to obtain the calculated content as desired. The agar was added as an extender. The batch was then thoroughly mixed and stored in the closed drum for half a day at ambient temperature. Acceptable gelatin capsules were then produced according to the working conditions listed on Table 45 below:

Material Composition: agar: 8%; gelatin 150B: 73%; water: 19%.

TABLE 45a

| $T_b$ | $T_m$ | $T_e$ | $T_g$ | $\frac{L}{D}$ | LFV |
|---|---|---|---|---|---|
| 110 | 120 | 130 | 130 | 66 | 850 |

EXAMPLE 43

A batch of bone gelatin 150 bloom, grade B, in granulated form was conditioned as follows:

The gelatin, having a water content of 11.7% was mixed with 24% by weight of dextran additive in a drum and sprayed with a fine spray of water to obtain the calculated content as desired. The dextran was added as an extender. The batch was then thoroughly mixed and stored in the closed drum for half a day at ambient temperature. Acceptable gelatin capsules were then produced according to the working conditions listed in Table 46 below:

Material Composition: dextran: 25%; gelatin 150B: 57%; water; 19%.

TABLE 46

| $T_b$ | $T_m$ | $T_e$ | $T_g$ | $\frac{L}{D}$ | LFV |
|---|---|---|---|---|---|
| 125 | 135 | 140 | 140 | 66 | 820 |

EXAMPLE 44

The batch of bone gelatin 150 bloom, grade B, in granulated form was conditioned as follows:

The gelatin, having a water content of 11.7% was mixed with 9% by weight of dextran additive in a drum and sprayed with a fine spray of water to obtain the calculated content as desired. The dextran was added as extender. The batch was then thoroughly mixed and stored in the closed drum for half a day at ambient temperature. Acceptable gelatin capsules were then produced according to the working conditions listed in Table 47 below:

Material Composition: dextran: 25%; gelatin 150B: 57%; water; 19%.

TABLE 47

| $T_b$ | $T_m$ | $T_e$ | $T_g$ | $\frac{L}{D}$ | LFV |
|---|---|---|---|---|---|
| 125 | 135 | 140 | 140 | 66 | 840 |

EXAMPLE 45

A batch of bone gelatin 150 bloom, grade B, in granulated form was conditioned as follows:

The gelatin, having a water content of 11.7% was mixed with 8% by weight of alginate additive in a drum and sprayed with a fine spray of water to obtain the calculated content as desired. The alginate was added as extender. The batch was then thoroughly mixed and stored in the closed drum for half a day at ambient temperature. Acceptable gelatin capsules were then produced according to the working conditions listed in Table 48 below:

Material Composition: alginate: 41%; gelatin 150B: 41% water: 18%.

TABLE 49

| $T_b$ | $T_m$ | $T_e$ | $T_g$ | $\frac{L}{D}$ | LFV |
|---|---|---|---|---|---|
| 110 | 1205 | 140 | 140 | 66 | 840 |

EXAMPLE 47

A batch of bone gelatin 150 bloom, grade B, in granulated form was conditioned as follows:

The gelatin, having a water content of 11.7% was mixed with 41% by weight of algin additive in a drum and sprayed with a fine spray of water to obtain the calculated content as desired. The 41% by weight of algin was added as extender. The batch was then thoroughly mixed and stored in the closed drum for half a day at ambient temperature. Acceptable gelatin capsules were then produced according to the working conditions listed in Table 50 below:

Material Composition: algin: 41%; gelatin 150B: 41% water: 18%.

TABLE 50

| $T_b$ | $T_m$ | $T_e$ | $T_g$ | $\frac{L}{D}$ | LFV |
|---|---|---|---|---|---|
| 100 | 120 | 120 | 120 | 66 | 850 |

EXAMPLE 48

A batch of bone gelatin, 150 bloom, grade B, in granulated form was conditioned as follows:

The gelatin, having a water content of 11.7% was mixed with 8% by weight of algin additive in a drum and sprayed with a fine spray of water to achieve the calculated content as desired. The algin was added as extender. The batch was then thoroughly mixed and stored in the closed drum for half a day at ambient temperature. Acceptable gelatin capsules were then produced according to the working conditions listed in Table 51 below:

Material Composition: algin: 8%; gelain 150B: 74% water: 18%.

TABLE 51

| $T_b$ | $T_m$ | $T_e$ | $T_g$ | $\frac{L}{D}$ | LFV |
|---|---|---|---|---|---|
| 100 | 120 | 120 | 120 | 66 | 834 |

EXAMPLE 49

A batch of HPMCP with water and glycerin, polyethleneglycol, calcium-stearate and microfine cellulose was prepared, conditioned and then tested in an injection molding machine. The batch of HPMCP in powdered form was conditioned as follows:

The HPMCP, having a water content of 2%, and the other additives were combined in a drum and sprayed with a fine spray of water to obtain the calculated content as desired. The batch was then thoroughly mixed and stored in the closed drum for half a day at ambient temperature. The resulting capsules have enteric properties (2 hours resistance in gastric juice, soluble well within 30 minutes in intestinal juice according to USP XX). Acceptable gelatin capsules were then produced according to the working conditions listed in Table 52 below:

Material Composition: HPMCP: 57.4%; glycerin: 4.1%; PE-glycol (10.000): 1%; Ca-stearate: 2%; micro fine cellulose: 27.6%; water: 7.9%.

TABLE 52

| $T_b$ | $T_m$ | $T_e$ | $T_g$ | $\frac{L}{D}$ | LFV |
|---|---|---|---|---|---|
| 110 | 120 | 140 | 140 | 66 | 835 |

The 4.1% by weight of glycerin was added as a softener. The 1% by weight of polyethyleneglycol was added as a plasticizer.

The 2% by weight of calcium-stearate was added as a lubricant.

The 27.6% by weight of micro fine cellulose was added as an extender.

EXAMPLE 50

A batch of HPMCP with water and glycerin, polyethleneglycol, calcium-stearate and microfine cellulose was prepared, conditioned and then tested in an injection molding machine. A batch of HPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. The resulting capsules have enteric properties (2 hours resistance in gastric juice, soluble well within 30 minutes in intestinal juice according to USP XX). Acceptable gelatin capsules were then produced according to the working conditions listed in Table 53 below:

Material Composition: HPMCP: 74.9%; glycerin: 5.4%; PE-glycol (10.000): 1.3%; Ca-stearate: 2.5%; micro fine cellulose: 9.4%; water: 6.5%

TABLE 53

| $T_b$ | $T_m$ | $T_e$ | $T_g$ | $\frac{L}{D}$ | LFV |
|---|---|---|---|---|---|
| 110 | 120 | 140 | 140 | 66 | 880 |

The 5.4% by weight of glycerin was added as a softener.

The 1.3% by weight of polyethyleneglycol was added as a plasticizer.

The 2.5% by weight of calcium-stearate was added as a lubricant.

The 9.4% by weight of microfine cellulose was added as an extender.

EXAMPLE 51

A batch of HPMCP with water and glycerin, polyethyleneglycol, calcium-stearate and Na-CMC was prepared, conditioned and tested in an injection molding machine. The batch of HPMCP in powdered form was conditioned as follows:

The HPMCP, having a water content of 2% and the other additives were combined in a drum and sprayed with a fine spray of water to obtain the calculated content as desired. The batch was then throughly mixed and stored in the closed drum for half a day at ambient temperature. Acceptable gelatin capsules were then produced according to the working conditions listed in Table 54 below:

Material Composition: HPMCP: 74.7%; glycerin: 5.4%; PE-glycol (10.000): 1.3%; Ca-stearate: 2.5%; Na-CMC: 9.4%; water: 6.7%.

TABLE 54

| $T_b$ | $T_m$ | $T_e$ | $T_g$ | $\frac{L}{D}$ | LFV |
|---|---|---|---|---|---|
| 110 | 120 | 140 | 140 | 66 | 850 |

The resulting capsules have enteric properties (2 hours resistance in gastric juice, soluble well within 30 minutes in intestinal juice according to USP XX).

The 5.4% by weight of glycerin was added as a softener.

The 1.3% by weight of polyethyleneglycol was added as a plasticizer.

The 2.5% by weight of calcium-stearate was added as a lubricant.

The 9.4% by weight of Na-CMC was added as an extender.

EXAMPLE 52

A batch of HPMCP with water and glycerin, polyethyleneglycol, calcium-stearate and agar was prepared, conditioned and then tested in an injection molding machine. The batch of HPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 55 below:

Material Composition: HPMCP: 34.4%; glycerin: 2.7%; PE-glycol (10.000): 0.7%; Ca-stearate: 1.3%; agar: 42%; water: 15.9%.

TABLE 55

| $T_b$ | $T_m$ | $T_e$ | $T_g$ | $\frac{L}{D}$ | LFV |
|---|---|---|---|---|---|
| 110 | 120 | 130 | 1340 | 66 | 830 |

The resulting capsules have enteric properties (2 hours resistance in gastric juice, soluble well within 30 minutes in intestinal juice according to USP XX).

The 2.7% by weight of glycerin was added as a softener.

The 0.7% by weight of polyethyleneglycol was added as a plasticizer.

The 1.3% by weight of calcium-stearate was added as a lubricant.

The 42% by weight of agar was added as an extender.

The 9.4% by weight of Na-CMC was added as an extender.

EXAMPLE 53

A batch of HPMCP with water and glycerin, polyethyleneglycol, calcium-stearate and agar was prepared, conditioned and tested in an injection molding machine. The batch of HPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 56 below:

Material Composition: HPMCP: 69%; glycerin: 5%; PE-glycol (10.000): 1.2%; Ca-stearate: 2.3%; agar: 8.7%; water: 13.8%.

TABLE 56

| $T_b$ | $T_m$ | $T_e$ | $T_g$ | $\frac{L}{D}$ | LFV |
|---|---|---|---|---|---|
| 110 | 125 | 135 | 135 | 66 | 830 |

The resulting capsules have enteric properties (2 hours resistance in gastric juice, soluble well within 30 minutes in intestinal juice according to USP XX).

The 5% by weight of glycerin was added as a softener.

The 1.2% by weight of polyethyleneglycol was added as a plasticizer.

The 2.3% by weight of calcium-stearate was added as a lubricant.

The 8.7% by weight of agar was added as an extender.

EXAMPLE 54

A batch of HPMCP with water and glycerin, polyethyleneglycol, calcium-stearate and hydroxypropylmethyl-cellulose was prepared, conditioned and tested in an injection molding machine. The batch of HPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 57 below:

Material Composition: HPMCP: 39.9%; glycerin: 2.9%; PE-glycol (10.000): 0.7%; Ca-stearate: 1.3%; HPMC: 44.9%; water: 13.8%.

TABLE 57

| $T_b$ | $T_m$ | $T_e$ | $T_g$ | $\frac{L}{D}$ | LFV |
|---|---|---|---|---|---|
| 110 | 120 | 140 | 140 | 66 | 835 |

The resulting capsules have enteric properties (2 hours resistance in gastric juice, soluble well within 30 minutes in intestinal juice according to USP XX).

The 2.9% by weight of glycerin was added as a softener.

The 0.7% by weight of polyethyleneglycol was added as a plasticizer.

The 1.3% by weight of calcium-stearate was added as a lubricant.

The 44.9% by weight of hydroxypropylmethyl-cellulose was added as an extender.

EXAMPLE 55

A batch for HPMCP with water and glycerin, polyethyleneglycol, calcium-stearate and hydroxypropylmethyl-cellulose was prepared, conditioned and tested in an injection molding machine. The batch of HPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 58 below:

Material Composition: HPMCP: 73.9%; glycerin: 5.3%; PE-glycol (10.000): 1.3%; Ca-stearate: 2.5%; HPMC: 9.2%; 7.8%.

TABLE 58

| $T_b$ | $T_m$ | $T_e$ | $T_g$ | $\frac{L}{D}$ | LFV |
|---|---|---|---|---|---|
| 110 | 125 | 135 | 135 | 66 | 860 |

The resulting capsules have enteric properties (2 hours resistance in gastric juice, soluble well within 30 minutes in intestinal juice according to USP XX).

The 5.3% by weight of glycerin was added as a softener.

The 1.3% by weight of polyethyleneglycol was added as a plasticizer.

The 2.5% by weight of calcium-stearate was added as a lubricant.

The 9.2% by weight of hydroxypropylmethyl-cellulose was added as an extender.

EXAMPLE 56

A batch of HPMCP with water and glycerin, polyethyleneglycol, calcium-stearate and soy protein was prepared, conditioned and then tested in an injection molding machine. The batch of MPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 59 below:

Material Composition: HPMCP: 40%; glycerin: 2.9%, PE-glycol (10.000): 0.7%; Ca-stearate: 1.3%; soy protein: 44.9%; water: 10.2%.

TABLE 59

| $T_b$ | $T_m$ | $T_e$ | $T_g$ | $\frac{L}{D}$ | LFV |
|---|---|---|---|---|---|
| 110 | 120 | 140 | 140 | 66 | 840 |

The resulting capsules have enteric properties (2 hours resistance in gastric juice, soluble well within 30 minutes in intestinal juice according to USP XX).

The 2.9% by weight of glycerin was added as a softener.

The 0.7% by weight of polyethyleneglycol was added as a plasticizer.

The 1.3% by weight of calcium-stearate was added as a lubricant.

44.9% by weight of soy protein were added as an extender.

EXAMPLE 57

A batch of HPMCP with water and glycerin, polyethyleneglycol, calcium-stearate and soy protein was prepared, conditioned and tested in an injection molding machine. The batch of HPMCP in powered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 60 below:

Material Composition: HPMCP: 40%; glycerin: 2.9%; PE-glycol (10.000): 0.7%: Ca-stearate: 1.3%; soy protein: 44.9%; water: 10.2%.

TABLE 60

| $T_b$ | $T_m$ | $T_e$ | $T_g$ | $\frac{L}{D}$ | LFV |
|---|---|---|---|---|---|
| 110 | 120 | 140 | 140 | 66 | 840 |

The resulting capsules have enteric properties (2 hours resistance in gastric juice, soluble well within 30 minutes in intestinal juice according to USP XX).

The 2.9% by weight of glycerin was added as a softener.

The 0.7% by weight of polyethyleneglycol was added as a plasticizer.

The 1.3% by weight of calcium-stearate was added as a lubricant.

The 44.9% by weight of soy protein was added as an extender.

EXAMPLE 57

A batch of HPMCP with water and glycerin, polyethyleneglycol, calcium-stearate and soy protein was prepared, conditioned and tested in an injection molding machine. The batch of HPMCP in powdered form was conditioned as follows:

The HPMCP, having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 60 below:

Material Composition: HPMCP: 74.3%; glycerin: 2.3%; PE-glycol (10.000): 1.3%; Ca-stearate: 2.5%; soy protein: 9.4%; water: 7.2%.

TABLE 60

| $T_b$ | $T_m$ | $T_e$ | $T_g$ | L/D | LFV |
|---|---|---|---|---|---|
| 110 | 125 | 135 | 135 | 66 | 1400 |

The resulting capsules have enteric properties (2 hours resistance in gastric juice, soluble well within 30 minutes in intestinal juice according to USP XX).

The 5.3% by weight of glycerin was added as a softener.

The 1.3% by weight of polyethyleneglycol was added as a plasticizer.

The 2.5% by weight of calcium-stearate was added as a lubricant.

The 9.4% by weight of soy protein was added as an extender.

EXAMPLE 58

A batch of HPMCP with water and glycerin, polyethyleneglycol, calcium-stearate and polyvinyl pyrrolidone was prepared, conditioned and tested in an injection molding machine. The batch of HPMCP in powdered form was conditioned as follows:

The HPMCP having a water content of 2% and the other additives were combined in a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 61 below:

Material Composition: HPMCP: 38.7%; glycerin: 2.8%; PE-glycol (10.000): 0.7%; Ca-stearate: 1.3%; polyvinylpyrrolidone: 43.5%; water: 13.0%.

TABLE 61

| $T_b$ | $T_m$ | $T_e$ | $T_g$ | L/D | LFV |
|---|---|---|---|---|---|
| 120 | 140 | 140 | 140 | 66 | 830 |

The resulting capsules have enteric properties (2 hours resistance in gastric juice, soluble well within 30 minutes in intestinal juice according to USP XX).

The 2.8% by weight of glycerin was added as a softener.

The 0.7% by weight of polyethyleneglycol was added as a plasticizer.

The 1.3% by weight of calcium-strearate was added as a lubricant.

The 43.5% by weight of polyvinyl pyrrolidone was added as an extender.

EXAMPLE 59

A batch of bone gelatin 150 bloom, grade B, in granulated form was conditioned as follows:

The mixture, having a water content of 11.7% was placed in a drum and sprayed with a fine spray of water to obtain the calculated content as desired. The batch was then thoroughly mixed and stored in the closed drum for half a day at ambient temperature. Acceptable gelatin capsules were then produced as follows:

Glutaraldehyde and formaldehyde have been used as crosslinking agents whereby they have been added to the molten gelatin in the sprue just at the gate. In order to get a homogeneous mixture of crosslinking agent and gelatin, the sprue has been equipped with a mixing device. The following material compositions were tested:

TABLE 62

| Material Composition in % by weight | Working Conditions | | | | | |
|---|---|---|---|---|---|---|
| | $T_b$ | $T_m$ | $T_e$ | $T_g$ | L/D | LFV |
| Gelatin 150B: 82.6; glutaraldehyde: 0.4; water: 17 | 110 | 120 | 140 | 140 | 66 | 860 |
| Gelatin 150B: 82.96; glutaraldehyde: 0.04; water: 17 | 110 | 120 | 140 | 140 | 66 | 860 |
| Gelatin 150B: 82.90; glutaraldeyhyde: 0.1; water: 17 | 110 | 120 | 140 | 140 | 66 | 860 |

These capsules were soluble in water at 37° C. for at least 2 hours.

EXAMPLE 60

A batch of bone gelatin 150 bloom, grade B, in granulated form was conditioned as follows:

The gelatin, having a water content of 17% was mixed with 17% by weight of hydroxypropyl cellulose additive in a drum and sprayed with a fine spray of water to obtain the calculated content as desired. The hydroxypropyl cellulose was added as a extender. The batch was then thoroughly mixed and stored in the closed drum for half a day at ambient temperature. Acceptable gelatin capsules were then produced according to the working conditions listed in table 63 below:

Material Composition: Hydroxypropyl cellulose: 17%; gelatin 150B: 68%; water: 17%.

TABLE 63

| $T_b$ | $T_m$ | $T_e$ | $T_g$ | L/D | LFV |
|---|---|---|---|---|---|
| 100 | 120 | 130 | 130 | 66 | 1000 |

EXAMPLE 61

A batch of gum arabic, inpowdered form, was conditioned as follows:

The gum arabic, having a water content of 10.8%, was poured into a drum and sprayed with a fine spray of water to obtain the calculated content as desired. The batch was then thoroughly mixed and stored in the closed drum for half a day at ambient temperature. Acceptable capsules were then produced according to the working conditions listed in Table 64 below:

Material Composition: gum arabic: 80.9%; water: 19.1%.

TABLE 64

| $T_b$ | $T_m$ | $T_e$ | $T_g$ | L/D | LFV |
|---|---|---|---|---|---|
| 75 | 105 | 112 | 130 | 66 | 800 |

EXAMPLE 62

A batch of methylcellulose in produced form, was conditioned as follows:

The methycellulose, having a water content of 6.6% was poured into a drum and sprayed with a fine spray of water to obtain the calculated content as desired. The batch was then thoroughly mixed and stored in the closed drum for half a day at ambient temperature. Acceptable gelatin capsules were then produced according to the working conditions listed in Table 65 below:

Material Composition: methylcellulose: 81.2%; water: 18.8%.

TABLE 65

| $T_b$ | $T_m$ | $T_e$ | $T_g$ | L/D | LFV |
|---|---|---|---|---|---|
| 84 | 129 | 149 | 161 | 66 | 800 |

EXAMPLE 63

A batch of polyvinyl pyrrolidone in powdered form, was conditioned as follows:

The polyvinyl pyrrolidone, having a water content of 16.8% was poured into a drum and sprayed with a fine spray of water to obtain the calculated content as desired. The batch was then thoroughly mixed and stored in the closed drum for half a day at ambient temperature. Acceptable capsules were then produced according to the working conditions listed in Table 66 below:

Material Composition: polyvinyl pyrrolidone: 81%; water: 19%.

TABLE 64

| $T_b$ | $T_m$ | $T_e$ | $T_g$ | L/D | LFV |
|---|---|---|---|---|---|
| 85 | 130 | 135 | 135 | 66 | 800 |

EXAMPLE 64

A batch of cellulose acetate phthalate in powdered form, was conditioned as follows:

The cellulose acetate phthalate, having a water content of 5.1% was poured into a drum and sprayed with a fine spray of water to obtain the calculated contented as desired. The batch was thoroughly mixed and stored in the closed drum for half a day at ambient temperature. Acceptable capsules were then produced according to the working conditions listed in Table 67 below:

Material Composition: cellulose acetate phthalate: 81% water 19%.

TABLE 67

| $T_b$ | $T_m$ | $T_e$ | $T_g$ | L/D | LFV |
|---|---|---|---|---|---|
| 90 | 130 | 140 | 145 | 66 | 800 |

As can be seen from the examples, the bone gelatins identified as 80A; 150A; 240A; 150B and 200B were used in connection with certain of the examples following Example 9. The identification "A" indicates that the gelatin was produced by acid processing of collagen raw materials, and the identification "B" indicates that the gelatin was obtained by alkaline processing of collagen raw materials. The numerical values are "bloom" values. A high bloom value indicates that the gelatin polymer has only been degraded slightly whereas low bloom values indicate that the polymer has been extensively degraded. There is a rough, but not absolute, correlation between bloom values and molecular weight, i.e., the higher bloom values indicate higher molecular weight and the lower bloom values indicate lower molecular weight gelatins.

The molecular weight values for the examples after Example 9 utilizing gelatins are as follows:

EXAMPLE 10, BONE GELATIN, 80 BLOOM, GRADE A

The following specifications of the molecular weight distribution have been measured:

| | |
|---|---|
| Weight (Average) | 81,000 Dalton |
| Viscosity (Average) | 64,000 Dalton |
| Molecular mass of smallest molecules | 10,000 Dalton |
| Molecular mass of largest molecules | 15,300,000 Dalton |

EXAMPLES 13-14, BONE GELATIN 240 BLOOM, GRADE A

The following specifications of the molecular weight distribution have been measured:

| | |
|---|---|
| Weight (Average) | 221,000 Dalton |
| Viscosity (Average) | 188,000 Dalton |
| Molecular mass of smallest molecules | 10,000 Dalton |
| Molecular mass of largest molecules | 15,300,000 Dalton |

EXAMPLES 15-16, 19-25, 27-28, 30-39, 41-48, 59, BONE GELATIN 150 BLOOM, GRADE B

The following specifications of the molecular weight distribution have been measured:

| | |
|---|---|
| Weight (Average) | 258,000 Dalton |
| Viscosity (Average) | 155,000 Dalton |
| Molecular mass of smallest molecules | 10,000 Dalton |
| Molecular mass of largest molecules | 15,300,000 Dalton |

EXAMPLES 17-18, BONE GELATIN 200 BLOOM, GRADE B

The following specifications of the molecular weight distribution have been measured:

| | |
|---|---|
| Weight (Average) | 299,000 Dalton |
| Viscosity (Average) | 187,000 Dalton |
| Molecular mass of smallest molecules | 10,000 Dalton |
| Molecular mass of largest molecules | 15,300,000 Dalton |

In addition to the foregoing compositions, injection moldable compositions in accordance with this invention have been made which included magnesium stearate at a concentration of 0.5% and at a concentration of 10% based on the weight of the entire composition. Injection moldable compositions made in accordance with this invention also may contain talc at 0.5% and at 10% concentrations based on the weight of the entire composition.

As can be further seen from the foregoing Examples, several additives compounds have been used. Descriptions for these compounds are as set forth below.

EXAMPLE 19, MICROCRYSTALLINE CELLULOSE

The microcrystalline cellulose used was AVICEL PH 102 obtainable from FMC corp., Marcus Hook, PA. Other types of microcrystalline cellulose could be used, such as AVICEL PH 105 or 101, both obtainable from the FMC Corp.

EXAMPLES 20-23, 49, 50 MICROFINE CELLULOSE

The microfine cellulose used was ELCEMA G250 by Degussa, Frankfurt and SOLKA FLOC Five granular, lot 1-4-20x. Other types and brands of microfine cellulose could be used such as ELCEMA P050, P100, or F150, also obtainable from Degussa.

EXAMPLES 24, 25, 64, CELLULOSE ACETATE PHTHALATE (CAP)

The cellulose acetate phthalate used contained 30-40% phthalate groups, 17-23% acetate groups, and about 6% free acid groups. A suitable commercial product for use in these examples is obtainable from Eastman Kodak Co., Rochester, N.Y.

EXAMPLES 26, 27, 49-58, POLYETHYLENE GLYCOL (PEG)

PEG having a molecular weight of 10,000 was used. However other PEG's can be used, preferably with a molecular weight greater than 1,000. Commercial brands of PEG suitable for use in these examples include, but are not limited to: CARBOWAX by Union Carbide, NY, PLUROCOL by Wyandotte, Mich., POLYGLYCOL by Dow Chemical, Mich., POLYGLYKOL E by Hoechst, Frankfurt, POLYWACHS by Huls, Marl, TETRONIC by Kuhlman, Paris, and LANOGEN by Joechst, Frankfurt.

EXAMPLES 26-28, 49-58, HYDROXYPROPYLMETHYL CELLULOSE PHTHALATE (HPMCP)

THe HPMCP used had a molecular weight of 20,000. A suitable commercial brand for use in these examples is HPMCP HP 50 obtained from Shinetsu Chemical Co., Tokyo.

EXAMPLE 29-31, ACRYLATE

Acrylate is a copolymer of acrylic acid and acid ethylester. The acrylate used had an acid number of 315 mg KOH/g and was obtained as EUDRAGIT L from Rohm Pharma, GmbH, Darmstadt.

EXAMPLES 32, 33, 56, 57, soy protein

The soy protein used was of normal food grade and is obtainable as PURINA PROTEINS from Ralston Purian, Mo.

EXAMPLES 34, 35, 54, 55 HYDROXYPROPYLMETHYL CELLULOSE (PHMC)

The HPMC used contained 19–30% methoxy, 3–12% hydroxypropyl groups and had a molecular weight of 6000. It is obtainable as VISCONTRAN from Henkel, Dusseldorf.

EXAMPLES 36, 37, 51, SODIUM CARBOXYMETHYL CELLULOSE (NA-CMC)

The Na-CMC used had an average molecular weight of 250,000 with a degree of substitution of 0.7. It was obtained as HERCULES CMC from Hercules Powder Co., Delaware.

EXAMPLES 38, 39, 58, 63, POLYVINYL PYRROLIDONE (PVP)

The PVP used had a pH of 3.5–5.0 in a 1% solution and had an average molecular weight of 10,000. It is obtainable as KOLLIDON from BASF AG, Ludwigshafen.

EXAMPLES 40–42a, 52, 53, AGAR

The macromolecule probably consists of the alternating copolymers β-D-galactopyranosyl-and 3,6-anhydro-α-L-galactopyranosyl-residue linked in the (1,3) position. The agar-agar used is of normal food grade, 60–80 mesh size.

EXAMPLES 43, 44, DEXTRAN

Dextran consists of poly (α-(,6)-D-glucose) with many α-1,4 branches. Average molecular weight is 110,000 Dalton.

EXAMPLES 45, 46, alginate

Alginate is produced from seaweed and is a sodium salt. The product used was obtained from Proton & Fagertum AS, Norway.

EXAMPLES 47, 48, ALGIN

Algin is the free acid counterpart of alginate (described above for examples 45 and 46).

EXAMPLE 40, HYDROXYPROPYL CELLULOSE (HPC)

The HPC used had an average molecular weight of 900,000 to 1,000,000, with a degree of substitution between 2 and 3. It is commercially available as KLUCEL HF from Hercules Inc., Wilmington. KLUCEL LF, also from Hercules, is suitable for use in these examples as well.

EXAMPLE 61, GUM ARABIC

The principal chain of the gum arabic polysaccharide consists essentially of 1,3 D-galactopyranose units. The gum arabic used had an average molecular weight of between 200,000 and 300,000.

EXAMPLE 62, METHYL CELLULOSE

The methyl cellulose used had a degree of substitution of approximately 2. It is obtained as VISCONTRAN MC 400 from Henkel, Dusseldorf.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

What is claimed is:

1. A method of making a molded capsule consisting essentially of a hydrophilic gelatin/water mixture wherein the water content is in the range of from about 5 to about 25% by weight of the hydrophyllic gelatin which comprises:
   (a) heating the hydrophyllic gelatin/water mixture to form a melt;
   (b) maintaining said water content during said heating;
   (c) further heating the hydrophyllic melt and water to a temperature to dissolve the melt in the water and achieve a homogeneous dispersion on a molecular level while maintaining said predetermined water content;
   (d) injecting the dissolved hydrophyllic melt into a mold cavity while maintaining a said water content;
   (e) cooling the hydrophyllic gelatin melt in said mold;
   (f) forming a multichambered molded product at a temperature below the glass transition temperature range of the hydrophyllic gelatin while maintaining said predetermined water content;
   (g) ejecting the molded product of said hydrophyllic gelatin from said mold.

2. A method for making pharmaceutical capsules consisting essentially of gelatin and water comprising a cap member and a body member each having at least one open end and sidewall means; and means located in each sidewall means for connecting said cap and body members together, said connecting means being configured and arranged to face each other to achieve, after connection of said cap and body members, a separation resistant connection; which method comprises:

mixing a gelatin/water composition with water in the predetermined amount between about 5 and 25% by weight of the gelatin/water composition;

heating the gelatin/water composition with said water at a temperature between about 50° and 190° C. while maintaining said predetermined water content to form a melt;

further heating the hydrophilic polymer melt and water to a temperature between about 110° and 180° C. to dissolve the melt in the water and achieve a homogeneous dispersion on a molecular level while maintaining said predetermined water content;

injecting the dissolved gelatin/water composition melt into a mold cavity while maintaining said predetermined water content;

cooling the gelatin/water composition melt in said mold; forming a multichambered molded product having an essentially amorphous polymer structure at a temperature below the glass transition temperature range of the gelatin/water composition while maintaining said predetermined water content; and ejecting the molded product of said gelatin/water composition from said mold, whereby said injection molded capsule exhibits a self sustaining shape and negligible reversible elastic deformation of the hydrophilic polymer.

3. A method for making molded mixture consisting essentially of hydrophilic gelatin and water pharmaceutical capsules comprising a cap member and a body member each having at least one open end and sidewall means; and means located in each sidewall means for connecting said cap and body members together, said connecting means being configured and arranged to face each other to achieve, after connection of said cap and body members, a separation resistant connection; and means for forming two or more compartments in the interior spaces defined by said body and cap members; which method comprises:

mixing the hydrophilic gelatin/water polymer with water in a predetermined amount between about 5 and 25% by weight of the hydrophilic polymer;

heating the hydrophilic polymer with said water at a temperature between about 110° and 180° C. while maintaining said predetermined water content to form a melt;

further heating the hydrophilic polymer melt and water to a temperature between about 50° and 190° C. to dissolve the melt in the water and achieve a homogeneous dispersion on a molecular level while maintaining said predetermined water content;

injecting the dissolved hydrophilic polymer melt into a mold cavity while maintaining said predetermined water content;

cooling the hydrophilic polymer melt in said mold; forming a multichamber molded product having an essentially amorphous polymer structure at a temperature below the glass transition temperature range of the hydrophilic polymer while maintaining said predetermined water content; and ejecting the molded product of said hydrophilic polymer from said mold, whereby said injection molded capsule exhibits a self sustaining shape and negligible reversable elastic deformation of the hydrophillic polymer.

* * * * *